US010906861B2

(12) United States Patent
Abraham et al.

(10) Patent No.: US 10,906,861 B2
(45) Date of Patent: Feb. 2, 2021

(54) METHODS OF MAKING ORGANIC COMPOUNDS BY METATHESIS

(71) Applicant: Wilmar Trading Pte Ltd, Singapore (SG)

(72) Inventors: Timothy W. Abraham, Minnetonka, MN (US); Hiroki Kaido, Eden Prairie, MN (US); Choon Woo Lee, La Canada, CA (US); Richard L. Pederson, San Gabriel, CA (US); Yann Schrodi, Agoura Hills, CA (US); Michael John Tupy, Crystal, MN (US)

(73) Assignee: Wilmar Trading Pte Ltd, Singapore (SG)

( * ) Notice: Subject to any disclaimer, the term of this patent is extended or adjusted under 35 U.S.C. 154(b) by 69 days.

(21) Appl. No.: 14/678,749

(22) Filed: Apr. 3, 2015

(65) Prior Publication Data
US 2015/0307438 A1 Oct. 29, 2015

Related U.S. Application Data

(63) Continuation of application No. 12/422,096, filed on Apr. 10, 2009, now Pat. No. 9,120,742, which is a continuation-in-part of application No. PCT/US2007/021933, filed on Oct. 15, 2007.

(60) Provisional application No. 60/851,632, filed on Oct. 13, 2006.

(51) Int. Cl.
*C07C 67/475* (2006.01)
*C07C 6/04* (2006.01)
*C07C 67/307* (2006.01)
*C07C 67/31* (2006.01)
*C07C 67/333* (2006.01)
*C07C 67/02* (2006.01)
*C07C 67/303* (2006.01)
*B01J 31/22* (2006.01)
*C07F 7/18* (2006.01)

(52) U.S. Cl.
CPC ......... *C07C 67/475* (2013.01); *B01J 31/2265* (2013.01); *B01J 31/2278* (2013.01); *C07C 6/04* (2013.01); *C07C 67/02* (2013.01); *C07C 67/303* (2013.01); *C07C 67/307* (2013.01); *C07C 67/31* (2013.01); *C07C 67/333* (2013.01); *C07F 7/1884* (2013.01); *B01J 2231/543* (2013.01); *B01J 2531/821* (2013.01); *C07C 2531/22* (2013.01); *C07C 2531/24* (2013.01)

(58) Field of Classification Search
None
See application file for complete search history.

(56) References Cited

U.S. PATENT DOCUMENTS

| 5,142,072 A | 8/1992 | Stipp et al. |
| 5,312,940 A | 5/1994 | Grubbs et al. |
| 5,710,298 A | 1/1998 | Grubbs et al. |
| 5,728,785 A | 3/1998 | Grubbs et al. |
| 5,728,917 A | 3/1998 | Grubbs et al. |
| 5,750,815 A | 5/1998 | Grubbs et al. |
| 5,811,515 A | 9/1998 | Grubbs et al. |
| 5,831,108 A | 11/1998 | Grubbs et al. |
| 5,849,851 A | 12/1998 | Grubbs et al. |
| 5,880,231 A | 3/1999 | Grubbs et al. |
| 5,917,071 A | 6/1999 | Grubbs et al. |
| 5,922,863 A | 7/1999 | Grubbs et al. |
| 5,939,504 A | 8/1999 | Woodson, Jr. et al. |
| 5,969,170 A | 10/1999 | Grubbs et al. |
| 5,977,393 A | 11/1999 | Grubbs et al. |
| 6,020,443 A | 2/2000 | Woodson, Jr. et al. |
| 6,040,363 A | 3/2000 | Warner et al. |
| 6,080,826 A | 6/2000 | Grubbs et al. |
| 6,107,420 A | 8/2000 | Grubbs et al. |
| 6,169,198 B1 | 1/2001 | Fischer et al. |
| 6,197,894 B1 | 3/2001 | Sunaga et al. |
| 6,211,315 B1 | 4/2001 | Larock et al. |
| 6,215,019 B1 | 4/2001 | Pederson et al. |
| 6,284,852 B1 | 9/2001 | Lynn et al. |
| 6,306,988 B1 | 10/2001 | Grubbs et al. |
| 6,310,121 B1 | 10/2001 | Woodson, Jr. et al. |
| 6,316,380 B1 | 11/2001 | Nolan et al. |
| 6,323,296 B1 | 11/2001 | Warner et al. |

(Continued)

FOREIGN PATENT DOCUMENTS

| EP | 0429995 A2 | 6/1991 |
| EP | 1408064 A1 | 4/2004 |

(Continued)

OTHER PUBLICATIONS

Nordin et al.,"Metathesis of palm oil", Journal of Molecular Catalysis, vol. 65, Issues 1-2, Mar. 1991, pp. 163-172.*

(Continued)

*Primary Examiner* — Rosalynd A Keys
(74) *Attorney, Agent, or Firm* — Kilpatrick Townsend & Stockton LLP

(57) ABSTRACT

Described are methods of making organic compounds by metathesis chemistry. The methods of the invention are particularly useful for making industrially-important organic compounds beginning with starting compositions derived from renewable feedstocks, such as natural oils. The methods make use of a cross-metathesis step with an olefin compound to produce functionalized alkene intermediates having a pre-determined double bond position. Once isolated, the functionalized alkene intermediate can be self-metathesized or cross-metathesized (e.g., with a second functionalized alkene) to produce the desired organic compound or a precursor thereto. The method may be used to make bifunctional organic compounds, such as diacids, diesters, dicarboxylate salts, acid/esters, acid/amines, acid/alcohols, acid/aldehydes, acid/ketones, acid/halides, acid/nitriles, ester/amines, ester/alcohols, ester/aldehydes, ester/ketones, ester/halides, ester/nitriles, and the like.

13 Claims, 5 Drawing Sheets

(56) References Cited

U.S. PATENT DOCUMENTS

| | | |
|---|---|---|
| 6,376,690 B1 | 4/2002 | Grubbs et al. |
| 6,409,875 B1 | 6/2002 | Giardello et al. |
| 6,410,110 B1 | 6/2002 | Warner et al. |
| 6,410,666 B1 | 6/2002 | Grubbs et al. |
| 6,426,419 B1 | 7/2002 | Grubbs et al. |
| 6,433,101 B1 | 8/2002 | Woodson, Jr. et al. |
| 6,465,590 B1 | 10/2002 | Maughon et al. |
| 6,486,264 B1 | 11/2002 | Tsunogae et al. |
| 6,525,125 B1 | 2/2003 | Giardello et al. |
| 6,583,236 B1 | 6/2003 | Giardello et al. |
| 6,610,626 B2 | 8/2003 | Grubbs et al. |
| 6,613,910 B2 | 9/2003 | Grubbs et al. |
| 6,620,955 B1 | 9/2003 | Pederson et al. |
| 6,696,597 B2 | 2/2004 | Pedersen et al. |
| 6,759,537 B2 | 7/2004 | Grubbs et al. |
| 6,794,534 B2 | 9/2004 | Grubbs et al. |
| 6,803,429 B2 | 10/2004 | Morgan et al. |
| 6,818,586 B2 | 11/2004 | Grubbs et al. |
| 6,838,489 B2 | 1/2005 | Bell et al. |
| 6,884,859 B2 | 4/2005 | Grubbs et al. |
| 6,900,347 B2 | 5/2005 | Paulson et al. |
| 6,921,735 B2 | 7/2005 | Hoveyda et al. |
| 6,921,736 B1 | 7/2005 | Nolan et al. |
| 6,946,533 B2 | 9/2005 | Grubbs et al. |
| 6,962,729 B2 | 11/2005 | Tokas et al. |
| 6,987,154 B2 | 1/2006 | Choi et al. |
| 7,026,495 B1 | 4/2006 | Pederson et al. |
| 7,034,096 B2 | 4/2006 | Choi et al. |
| 7,109,348 B1 | 9/2006 | Nolan |
| 7,119,216 B2 | 10/2006 | Newman et al. |
| 7,176,336 B2 | 2/2007 | Maughon et al. |
| 7,205,424 B2 | 4/2007 | Nolan |
| 7,285,593 B1 | 10/2007 | Giardello et al. |
| 7,314,904 B2 | 1/2008 | Nadolsky et al. |
| 7,329,758 B1 | 2/2008 | Grubbs et al. |
| 7,365,140 B2 | 4/2008 | Piers et al. |
| 7,507,854 B2 | 3/2009 | Lee et al. |
| 7,576,227 B2 | 8/2009 | Lysenko |
| 7,585,990 B2 | 9/2009 | Toor et al. |
| 7,598,330 B2 | 10/2009 | Grubbs et al. |
| 7,622,590 B1 | 11/2009 | Nolan et al. |
| 7,678,932 B2 | 3/2010 | Thurier et al. |
| 7,812,185 B2 | 10/2010 | Burdett et al. |
| 2002/0095007 A1 | 7/2002 | Larock et al. |
| 2003/0055262 A1 | 3/2003 | Grubbs et al. |
| 2003/0100776 A1 | 5/2003 | Grubbs et al. |
| 2003/0149299 A1 | 8/2003 | Borhan et al. |
| 2003/0186035 A1 | 10/2003 | Cruce et al. |
| 2005/0070750 A1 | 3/2005 | Newman et al. |
| 2005/0154221 A1* | 7/2005 | Lysenko ............... C07C 67/333 554/174 |
| 2005/0261451 A1 | 11/2005 | Ung et al. |
| 2006/0079704 A1 | 4/2006 | Lacombe et al. |
| 2006/0289138 A1 | 12/2006 | Borsinger et al. |
| 2007/0179307 A1 | 8/2007 | Olivier-Bourbigou et al. |
| 2007/0270621 A1 | 11/2007 | Millis et al. |
| 2008/0027194 A1 | 1/2008 | Schrodi |
| 2008/0064891 A1 | 3/2008 | Lee |
| 2009/0048459 A1 | 2/2009 | Tupy et al. |
| 2009/0126602 A1 | 5/2009 | Murphy et al. |
| 2009/0217568 A1 | 9/2009 | Murphy et al. |
| 2009/0220443 A1 | 9/2009 | Braksmayer et al. |
| 2009/0259065 A1 | 10/2009 | Abraham et al. |
| 2010/0047499 A1 | 2/2010 | Braksmayer et al. |
| 2010/0094034 A1 | 4/2010 | Kaido et al. |
| 2010/0145086 A1 | 6/2010 | Schrodi et al. |

FOREIGN PATENT DOCUMENTS

| | | |
|---|---|---|
| EP | 1810960 A1 | 7/2007 |
| FR | 2878246 A1 | 5/2006 |
| JP | 56-077243 A | 6/1981 |
| JP | 09-014574 A | 1/1997 |
| SU | 1565872 A1 | 7/1988 |
| WO | WO 94/23836 A1 | 10/1994 |
| WO | WO 96/04289 A1 | 2/1996 |
| WO | WO 01/36368 A2 | 5/2001 |
| WO | WO 03/093215 A1 | 11/2003 |
| WO | WO 2004/062763 A2 | 7/2004 |
| WO | WO 2005/026106 A1 | 3/2005 |
| WO | WO 2005/080455 A1 | 9/2005 |
| WO | WO 2006/052688 A2 | 5/2006 |
| WO | WO 2007/081987 A2 | 7/2007 |
| WO | WO 2007/103398 A1 | 9/2007 |
| WO | WO 2007/103460 A2 | 9/2007 |
| WO | WO 2008/008420 A1 | 1/2008 |
| WO | WO 2008/010961 A2 | 1/2008 |
| WO | WO 2008/046106 A2 | 4/2008 |
| WO | WO 2008/048520 A2 | 4/2008 |
| WO | WO 2008/048522 A1 | 4/2008 |
| WO | WO 2008/063322 A2 | 5/2008 |
| WO | WO 2008/140468 A2 | 11/2008 |

OTHER PUBLICATIONS

C. Mol. ("Metathesis of unsaturated fatty acid esters and fatty oils", Journal of Molecular Catalysis, vol. 90, 1994, pp. 185-199).*

Patel et al. ("High conversion and productive catalyst turnovers in cross-metathesis reactions of natural oils with 2-butene", Green Chemistry, vol. 8, 2006, pp. 450-454).*

Verkuijlen et al., "Metathesis of Unsaturated Fatty Esters," Fette, Seifen, Anstrichmittel, Industrieverlag von Hernhaussen KG, Hamburg, vol. 78, pp. 444-447 (1976).

Communication issued in European Patent App. No. 07874079.2, dated Jul. 22, 2014.

Refvik, M.D. et al., "The Chemistry of Metathesized Soybean Oil," JAOCS, vol. 76, No. 1, 1999, pp. 99-102.

Anderson et al., "Synthesis and Reactivity of Olefin Metathesis Catalysts Bearing Cyclic (Alkyl)(Amino) Carbenes," Angewandte Chemie International Edition, vol. 46, 2007, pp. 7262-7265.

Baumann et al., "Natural Fats and Oils—Renewable Raw Materials for the Chemical Industry," Angewandte Chemie International Edition in English, vol. 27, 1988, pp. 41-62.

Biermann et al., "New Syntheses with Oils and Fats as Renewable Raw Materials for the Chemical Industry,", Angewandte Chemie International Edition, vol. 39, 2000, pp. 2206-2224.

Boelhouwer et al., "Metathesis Reactions of Fatty Acid Esters," Progress of Lipid Research, Pergamon Press, vol. 24, No. 3, 1985, pp. 243-267.

Choi et al., "Olefin Metathesis Involving Ruthenium Enoic Carbene Complexes," Journal of the American Chemical Society, vol. 123, No. 42, 2001, pp. 10417-10418.

Connon et al., "A Solid-Supported Phosphine-Free Ruthenium Alkylidene for Olefin Metathesis in Methanol and Water," Bioorganic & Medical Chem Letters, vol. 12, No. 14, 2002, pp. 1873-1876.

Dunne et al., "A Highly Efficient Olefin Metathesis Initiator: Improved Synthesis and Reactivity Studies," Tetrahedron Letters, vol. 44, No. 13, 2003, pp. 2733-2736.

Erhan et al. , "Drying Properties of Metathesized Soybean Oil," Journal of American Oil Chemists' Society, AOCS Press, vol. 74, No. 6, 1997, pp. 703-706.

Lavallo, "Stable Cyclic (Alkyl)(Amino) Carbenes as Rigid or Flexible, Bulky, Electron-Rich Ligands for Transition-Metal Catalysts: A Quaternary Carbon Atom Makes the Difference," Angewandte Chemie Int. Ed., vol. 44, 2005, pp. 5705-5709.

Maynard et al., "Purification Technique for the Removal of Ruthenium from Olefin Metathesis Reaction Products," Tetrahedron Letters, vol. 40, No. 22, 1999, pp. 4137-4140.

Mol, J.C., "Metathesis of unsaturated fatty acid esters and fatty oils," Journal of Molecular Catalysis, vol. 90, 1994, pp. 185-199.

Mol, "Applications of Olefin Metathesis in Oleochemistry: An Example of Green Chemistry," Green Chemistry, Royal Society of Chemistry, Cambridge, GB, vol. 4, 2002, pp. 5-13.

Mol et al., "Metathesis in Oleochemistry," J Braz Chem Soc, vol. 9, No. 1, 1998, pp. 1-11.

Mol, "Catalytic Metathesis of Unsaturated Fatty Acid Esters and Oils," Topics in Catalysis, vol. 27, No. 1-4, 2004, pp. 97-104.

(56) References Cited

OTHER PUBLICATIONS

Patel et al., "High conversion and productive catalyst turnovers in cross-metathesis reactions of natural oils with 2-butene", Green Chemistry, 2006, vol. 8, pp. 450-454.
Refvik et al., "Ruthenium-Catalyzed Metathesis of Vegetable Oils," Journal of American Oil Chemists' Society, AOCS Press, vol. 76, No. 1, 1999, pp. 93-98.
Schneider et al., "Synthesis of Highly Substituted Cyclopentane and Tetrahydrofuran Derivatives by Crossed Olefin Metathesis," Angewandte Chemi International Edition, vol. 35, No. 4, 1996, pp. 411-412.
Tian et al., "Model Studies and the ADMET Polymerization of Soybean Oil," Journal of American Oil Chemists' Society, AOCS Press, vol. 79, No. 5, 2002, pp. 479-488.
Warwel et al., "Metathese ungesättigter Fettsäureester—ein einfacher Zugang zu langkettigen Dicarbonsäuren," Fat Sci. Technol. vol. 94, No. 9, 1992, pp. 323-327.
Warwel, Siegfried et al., "Polymers and surfactants on the basis of renewable resources," Chemosphere, vol. 43, 2001, pp. 39-48.
Extended European Search Report for European Application No. 07874079.2, dated Oct. 19, 2010, 13, pages.
Patel, Jim et al., "Cross-metathesis of unsaturated natural oils with 2-butene. High conversion and productive catalyst turnovers," Chem. Commun., 2005, 5546-5547.
Warwel, Siegfried et al. "Synthesis of Dicarboxylic Acids by Transition-Metal Catalyzed Oxidative Cleavage of Terminal-Unsaturated Fatty Acids," Topics in Current Chemistry, vol. 164, 1993, pp. 79-98.
International Search Report and Written Opinion for International Application No. PCT/US2007/021933, dated Feb. 26, 2009, 6 pages.
Chatterjee et al., "Synthesis of Trisubstituted Alkenes via Olefin Cross-Metathesis," Organic Letters, vol. 1, No. 11, 1999, pp. 1751-1753.

\* cited by examiner

METHODS OF MAKING ORGANIC COMPOUNDS BY METATHESIS

CROSS-REFERENCE TO RELATED APPLICATIONS

This application is a continuation-in-part of International Application No. PCT/US2007/021933, filed Oct. 15, 2007, which claims the benefit of U.S. Provisional Application having Ser. No. 60/851,632, filed Oct. 13, 2006, and entitled METHODS OF MAKING ORGANIC COMPOUNDS BY METATHESIS, the disclosures of which are incorporated herein by reference.

GOVERNMENT RIGHTS

This invention was made with U.S. Government support under Award Number DE-FG36-04GO14016 awarded by the U.S. Department of Energy. The Government may have certain rights in this invention.

BACKGROUND

It is desirable to use renewable feedstocks (e.g., natural oil-derived fatty acids or fatty esters) as a source material for synthesizing industrially important organic compounds that have been conventionally manufactured from petroleum feedstocks. One useful reaction for modifying the structure of natural oil-derived feedstocks is metathesis. Metathesis is a catalytic reaction involving the rupture and reformation of carbon-carbon double bonds. When metathesis is applied directly to many natural oil-derived feedstocks, a mixture of products results. For example, when metathesis is applied to a mixture of fatty acid esters, the resulting metathesis products include a mixture of monoesters and diesters of various chain lengths. Due to the similarity in molecular weight and functionality of the products, it is difficult to separate the desired product (e.g., a particular chain length diester) from the other metathesis products.

In view of the foregoing, what is desired is a method by which bifunctional compounds such as dicarboxylic acids, dicarboxylate esters, and dicarboxylate salt compounds can be manufactured in high yields from metathesis reactions applied to starting materials such as fatty acids, fatty esters, fatty acid salts, and mixtures thereof.

SUMMARY

The invention relates to methods of making organic compounds by metathesis chemistry. The methods of the invention are particularly useful for making industrially-important organic compounds from starting compositions that are derived from renewable feedstocks, such as natural oils.

The methods of the invention make use of a cross-metathesis step with an olefin compound to produce functionalized alkene intermediates having a pre-determined double bond position. Advantageously, the functionalized alkene intermediates can be isolated at high purity from the other cross-metathesis products and from any remaining starting material. Once isolated, the functionalized alkene intermediate can be self-metathesized or cross-metathesized (e.g., with a second functionalized alkene) to produce the desired bifunctional organic compound or a precursor thereto. Representative organic compounds include bifunctional organic compounds, such as diacids, diesters, dicarboxylate salts, acid/esters, acid/amines, acid/alcohols, acid/aldehydes, acid/ketones, acid/halides, acid/nitriles, ester/amines, ester/alcohols, ester/aldehydes, ester/ketones, ester/halides, ester/nitriles, and the like.

Accordingly, in one aspect, the invention provides a method of making diacid alkenes, diester alkenes, or dicarboxylate salt alkenes by metathesis. The method of the invention comprises the steps of:

(a) providing a starting composition comprising one or more unsaturated fatty acids, unsaturated fatty esters, or unsaturated fatty acid salts;

(b) cross-metathesizing the composition of step (a) with a short-chain olefin in the presence of a first metathesis catalyst, to form cross-metathesis products comprising: (i) one or more olefins; and (ii) one or more acid-, ester-, or carboxylate salt-functionalized alkenes;

(c) separating at least a portion of one or more of the acid-, ester-, or carboxylate salt-functionalized alkenes from the cross-metathesis products; and (d) self-metathesizing the separated acid-, ester-, or carboxylate salt-functionalized alkene in the presence of a second metathesis catalyst to form a composition comprising one or more diacid alkenes, diester alkenes, or dicarboxylate salt alkenes.

In another aspect, the invention provides a method of making bifunctional organic compounds, the method comprising the steps of:

(a) providing a starting composition comprising one or more unsaturated fatty acids, unsaturated fatty esters, or unsaturated fatty acid salts;

(b) cross-metathesizing the starting composition of step (a) with a short-chain olefin in the presence of a first metathesis catalyst to form cross-metathesis products comprising: (i) one or more olefins; and (ii) one or more acid-, ester-, or carboxylate salt-functionalized alkenes;

(c) separating at least a portion of the one or more acid-, ester-, or carboxylate salt-functionalized alkenes from the cross-metathesis products; and (d) cross-metathesizing the separated acid-, ester-, or carboxylate salt-functionalized alkenes with a second functionalized alkene in the presence of a metathesis catalyst to form a composition comprising a bifunctional organic compound.

DETAILED DESCRIPTION

Figure 1:
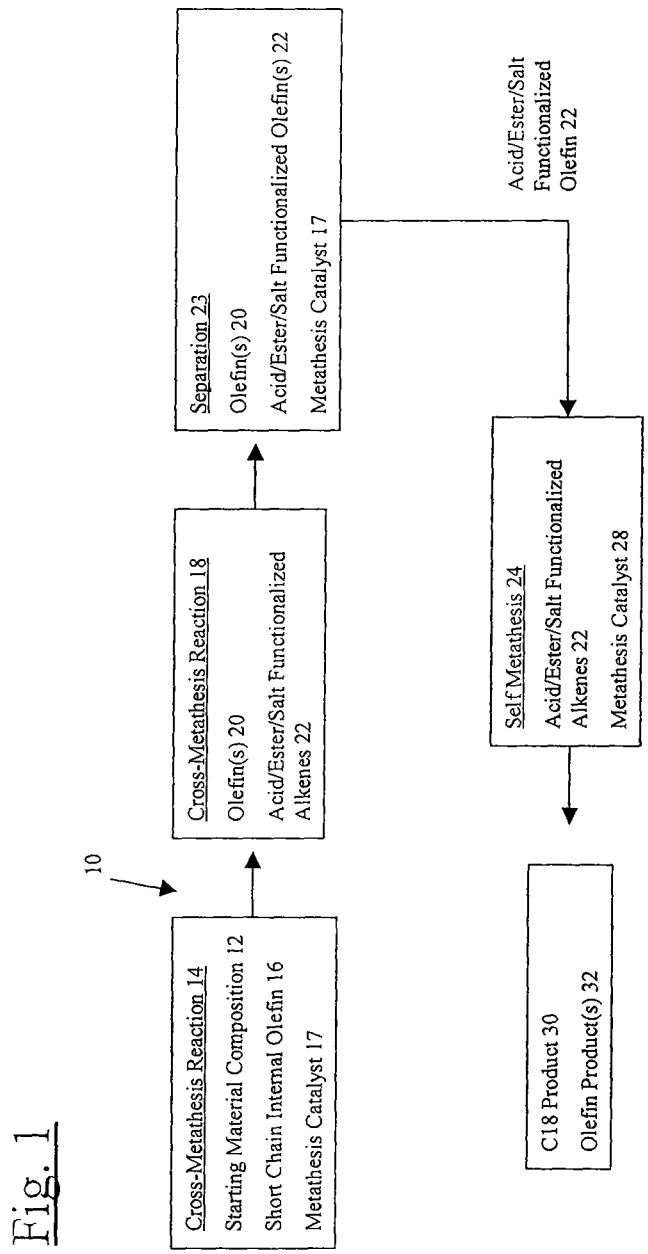
FIG. 1 is a process flow diagram of an embodiment of the method of the invention.

Starting Composition (Step (a)):

As a starting composition, the method of the present invention uses unsaturated fatty acids, unsaturated fatty esters, salts of unsaturated fatty acids, or a mixture. As used herein the term "unsaturated fatty acid" refers to compounds that have an alkene chain with a terminal carboxylic acid group. The alkene chain may be a linear or branched and may optionally include one or more functional groups in addition to the carboxylic acid group. For example, some carboxylic acids include one or more hydroxyl groups. The alkene chain typically contains about 4 to about 30 carbon atoms, more typically about 4 to about 22 carbon atoms. In many embodiments, the alkene chain contains 18 carbon atoms (i.e., a C18 fatty acid). The unsaturated fatty acids have at least one carbon-carbon double bond in the alkene chain (i.e., a monounsaturated fatty acid), and may have more than one double bond (i.e., a polyunsaturated fatty acid) in the alkene chain. In exemplary embodiments, the unsaturated fatty acid has from 1 to 3 carbon-carbon double bonds in the alkene chain.

Also useful as starting compositions are unsaturated fatty esters. As used herein the term "unsaturated fatty ester" refers to a compounds that have an alkene chain with a terminal ester group. The alkene chain may be linear or branched and may optionally include one or more functional groups in addition to the ester group. For example, some unsaturated fatty esters include one or more hydroxyl groups in addition to the ester group. Unsaturated fatty esters include "unsaturated monoesters" and "unsaturated polyol esters". Unsaturated monoesters have an alkene chain that terminates in an ester group, for example, an alkyl ester group such as a methyl ester. The alkene chain of the unsaturated monoesters typically contains about 4 to about 30 carbon atoms, more typically about 4 to 22 carbon atoms. In exemplary embodiments, the alkene chain contains 18 carbon atoms (i.e., a C18 fatty ester). The unsaturated monoesters have at least one carbon-carbon double bond in the alkene chain and may have more than one double bond in the alkene chain. In exemplary embodiments, the unsaturated fatty ester has 1 to 3 carbon-carbon double bonds in the alkene chain.

Also useful as a starting composition are metal salts of unsaturated fatty acids (i.e., carboxylate salts of unsaturated fatty acids). The metal salts may be salts of alkali metals (e.g., a group IA metal such as Li, Na, K, Rb, and Cs); alkaline earth metals (e.g., group IIA metals such as Be, Mg, Ca, Sr, and Ba); group IIIA metals (e.g., B, Al, Ga, In, and Tl); group IVA metals (e.g., Sn and Pb), group VA metals (e.g., Sb and Bi), transition metals (e.g., Sc, Ti, V, Cr, Mn, Fe, Co, Ni, Cu, Zn, Zr, Mo, Ru, Rh, Pd, Ag and Cd), lanthanides or actinides.

In many embodiments, the unsaturated fatty acid, ester, or carboxylate salt has a straight alkene chain and can be represented by the general formula:

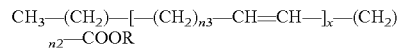

where:
R is hydrogen (fatty acid), an aliphatic group (fatty ester), or a metal ion (carboxylate salt);
n1 is an integer equal to or greater than 0 (typically 0 to 15; more typically 0, 3, (or 6);
n2 is an integer equal to or greater than 0 (typically 2 to 11; more typically 3, 4, 7, 9, or, a);
n3 is an integer equal to or greater than 0 (typically 0 to 6; more typically 1); and
x is an integer equal to or greater than 1 (typically 1 to 6, more typically 1 to 3).

A summary of some unsaturated fatty acids and esters is provided in TABLE A.

TABLE A

Unsaturated Fatty Acids/Esters

| Type | General Formula | Examples of fatty acids | Examples of fatty esters |
|---|---|---|---|
| Monounsaturated | $CH_3$—$(CH_2)_{n1}$—[—$(CH_2)_{n3}$—CH=CH—]$_x$—$(CH_2)_{n2}$—COOR<br>Where x is 1, and n1, n2, n3, and R are as described above. | Oleic Acid<br>(x = 1,<br>n1 = 6;<br>n2 = 7;<br>n3 = 1;<br>and R is H.) | Methyl Oleate<br>(x = 1,<br>n1 = 6;<br>n2 = 7;<br>n3 = 1;<br>and R is CH3.) |
| Polyunsaturated | Diunsaturated<br>$CH_3$—$(CH_2)_{n1}$—[—$(CH_2)_{n3}$—CH=CH—]$_x$—$(CH_2)_{n2}$—COOR<br>Where x is 2, and n1, n2, n3, and R are as described above. | Linoleic acid<br>(x = 2,<br>n1 = 3;<br>n2 = 7;<br>n3 = 1;<br>and R is H.) | Methyl Linoleate<br>(x = 2,<br>n1 = 3;<br>n2 = 7;<br>n3 = 1;<br>and R is CH3.) |
| | Triunsaturated<br>$CH_3$—$(CH_2)_{n1}$—[—$(CH_2)_{n3}$—CH=CH—]$_x$—$(CH_2)_{n2}$—COOR<br>Where x is 3, and n1, n2, n3, and R are as described above. | Linolenic acid<br>(x = 3,<br>n1 = 0;<br>n2 = 7;<br>n3 = 1;<br>and R is H.) | Methyl Linolenate<br>(x = 3,<br>n1 = 0;<br>n2 = 7;<br>n3 = 1;<br>and R is CH3.) |

Unsaturated monoesters may be alkyl esters (e.g., methyl esters) or aryl esters and may be derived from unsaturated fatty acids or unsaturated glycerides by transesterifying with a monohydric alcohol. The monohydric alcohol may be any monohydric alcohol that is capable of reacting with the unsaturated free fatty acid or unsaturated glyceride to form the corresponding unsaturated monoester. In some embodiments, the monohydric alcohol is a C1 to C20 monohydric alcohol, for example, a C1 to C12 monohydric alcohol, a C1 to C8 monohydric alcohol, or a C1 to C4 monohydric alcohol. The carbon atoms of the monohydric alcohol may be arranged in a straight chain or in a branched chain structure, and may be substituted with one or more substituents. Representative examples of monohydric alcohols include methanol, ethanol, propanol (e.g., isopropanol), and butanol.

Transesterification of an unsaturated triglyceride can be represented as follows.

1 Unsaturated Triglyceride+3 Alcohol→1 Glycerol+3 Monoesters

Depending upon the make-up of the unsaturated triglyceride, the above reaction may yield one, two, or three moles of unsaturated monoester.

Transesterification is typically conducted in the presence of a catalyst, for example, alkali catalysts, acid catalysts, or enzymes. Representative alkali transesterification catalysts include NaOH, KOH, sodium and potassium alkoxides (e.g., sodium methoxide), sodium ethoxide, sodium propoxide, sodium butoxide. Representative acid catalysts include sulfuric acid, phosphoric acid, hydrochloric acid, and sulfonic acids. Heterogeneous catalysts may also be used for transesterification. These include alkaline earth metals or their salts such as CaO, MgO, calcium acetate, barium acetate, natural clays, zeolites, Sn, Ge or Pb, supported on various materials such as ZnO, MgO, $TiO_2$, activated carbon or graphite, and inorganic oxides such as alumina, silica-alumina, boria, oxides of P, Ti, Zr, Cr, Zn, Mg, Ca, and Fe. In exemplary embodiments, the triglyceride is transesterified with methanol ($CH_3OH$) in order to form free fatty acid methyl esters.

In some embodiments, the unsaturated fatty esters are unsaturated polyol esters. As used herein the term "unsaturated polyol ester" refers to compounds that have at least one unsaturated fatty acid that is esterified to the hydroxyl group of a polyol. The other hydroxyl groups of the polyol may be unreacted, may be esterified with a saturated fatty acid, or may be esterified with an unsaturated fatty acid. The fatty acids in the polyol ester may be linear or branched and may optionally have functional groups other than the carboxylic acid such as one or more hydroxyl groups. Examples of polyols include glycerol, 1, 3 propanediol, propylene glycol, erythritol, trimethylolpropane, pentaerythritol, and sorbitol. In many embodiments, unsaturated polyol esters have the general formula:

$$R(O-Y)_m(OH)_n(O-X)_b$$

where
R is an organic group having a valency of (n+m+b);
m is an integer from 0 to (n+m+b−1), typically 0 to 2;
b is an integer from 1 to (n+m+b), typically 1 to 3;
n is an integer from 0 to (n+m+b−1), typically 0 to 2;
(n+m+b) is an integer that is 2 or greater;
X is —(O)C—$(CH_2)_{n2}$—[—CH=CH—$(CH_2)_{n3}$—]$_x$—$(CH_2)_{n1}$—$CH_3$;
Y is —(O)C—R';
R' is a straight or branched chain alkyl or alkenyl group;
n1 is an integer equal to or greater than 0 (typically 0 to 15; more typically 0, 3, or 6);
n2 is an integer equal to or greater than 0 (typically 2 to 11; more typically 3, 4, 7, 9, or 11);
n3 is an integer equal to or greater than 0 (typically 0 to 6; more typically 1); and
x is an integer equal to or greater than 1 (typically 1 to 6, more typically 1 to 3).

In many embodiments, the unsaturated polyol esters are unsaturated glycerides. As used herein the term "unsaturated glyceride" refers to a polyol ester having at least one (e.g., 1 to 3) unsaturated fatty acid that is esterified with a molecule of glycerol. The fatty acid groups may be linear or branched and may include pendant hydroxyl groups. In many embodiments, the unsaturated glycerides are represented by the general formula:

$$CH_2A\text{-}CHB\text{--}CH_2C$$

where -A; —B; and —C are selected from
—OH;
—O(O)C—$(CH_2)_{n2}$—[—CH=CH—$(CH_2)_{n3}$—]$_x$—$(CH_2)_{n1}$—$CH_3$; and
—O(O)C—R';
with the proviso that at least one of -A, —B, or —C is
—O(O)C—$(CH_2)_{n2}$—[—CH=CH—$(CH_2)_{n3}$-]$_x$—$(CH_2)_{n1}$—$CH_3$.

In the above formula:
R' is a straight or branched chain alkyl or alkenyl group;
n1 is an integer equal to or greater than 0 (typically 0 to 15; more typically 0, 3, or 6);
n2 is an integer equal to or greater than 0 (typically 2 to 11; more typically 3, 4, 7, 9, or 11);
n3 is an integer equal to or greater than 0 (typically 0 to 6; more typically 1); and
x is an integer equal to or greater than 1 (typically 1 to 6, more typically 1 to 3).

Unsaturated glycerides having two —OH groups (e.g., -A and —B are —OH) are commonly known as unsaturated monoglycerides. Unsaturated glycerides having one —OH group are commonly known as unsaturated diglycerides. Unsaturated glycerides having no —OH groups are commonly known as unsaturated triglycerides.

As shown in the formula above, the unsaturated glyceride may include monounsaturated fatty acids, polyunsaturated fatty acids, and saturated fatty acids that are esterified to the glycerol molecule. The main chain of the individual fatty acids may have the same or different chain lengths. Accordingly, the unsaturated glyceride may contain up to three different fatty acids so long as at least one fatty acid is an unsaturated fatty acid.

In many embodiments, useful starting compositions are derived from natural oils such as plant-based oils or animal fats. Representative examples of plant-based oils include canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, castor oil, and the like. Representative examples of animal fats include lard, tallow, chicken fat (yellow grease), and fish oil. Other useful oils include tall oil and algae oil.

In many embodiments, the plant-based oil is soybean oil. Soybean oil comprises unsaturated glycerides, for example, in many embodiments about 95% weight or greater (e.g., 99% weight or greater) triglycerides. Major fatty acids making up soybean oil include saturated fatty acids, for example, palmitic acid (hexadecanoic acid) and stearic acid (octadecanoic acid), and unsaturated fatty acids, for example, oleic acid (9-octadecenoic acid), linoleic acid (9, 12-octadecadienoic acid), and linolenic acid (9,12,15-octadecatrienoic acid). Soybean oil is a highly unsaturated vegetable oil with many of the triglyceride molecules having at least two unsaturated fatty acids.

The method of the invention can be used to produce multiple organic acid compounds. As discussed below, the position of the carbon-carbon double bond closest to the carboxylic acid, ester, or carboxylate salt group dictates the chain length of the organic acid compound that is formed by the method of the invention.

Δ9 Starting Compositions:

In many embodiments, the starting composition comprises a Δ9 unsaturated fatty acid, a Δ9 unsaturated fatty ester (e.g., monoesters or polyol esters), a Δ9 unsaturated fatty acid salt, or a mixture of two or more of the foregoing. Δ9 unsaturated starting materials have a carbon-carbon double bond located between the 9$^{th}$ and 10$^{th}$ carbon atoms (i.e., between C9 and C10) in the alkene chain of the unsaturated fatty acid, ester, or salt. In determining this position, the alkene chain is numbered beginning with the carbon atom in the carbonyl group of the unsaturated fatty acid, ester, or salt. Δ9 unsaturated fatty acids, esters, and salts include polyunsaturated fatty acids, esters, or salts (i.e., having more than one carbon-carbon double bond in the alkene chain) so long as one of the carbon-carbon double bonds is located between C9 and C10. For example, included within the definition of Δ9 unsaturated fatty acids, esters, or salts are Δ9, 12 unsaturated fatty acids, esters or salts, and Δ9, 12, 15 unsaturated fatty acids, esters or salts.

In many embodiments, the Δ9 unsaturated starting materials have a straight alkene chain and may be represented by the general structure:

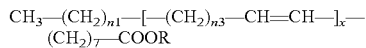

where
R is hydrogen (fatty acid), an aliphatic group (fatty monoester) or a metal ion (carboxylate salt);
n1 is an integer equal to or greater than 0 (typically 0 to 6; more typically 0, 3, 6);
n3 is an integer equal to or greater than 0 (typically 1); and
x is an integer equal to or greater than 1 (typically 1 to 6, more typically 1 to 3).

In exemplary embodiments, the Δ9 unsaturated starting materials have a total of 18 carbons in the alkene chain. Examples include

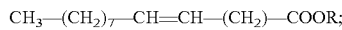

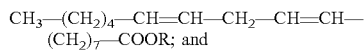

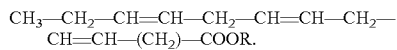

where R is hydrogen (fatty acid), an aliphatic group (fatty monoester) or a metal ion (fatty acid salt);

Δ9 unsaturated fatty esters may be monoesters or polyol esters. In many embodiments, the Δ9 unsaturated polyol esters have the general structure

CH$_2$A-CHB—CH$_2$C where -A; —B; and —C are independently selected from
—OH;
—O(O)C—R'; and
—O(O)C—(CH$_2$)$_7$—[—CH=CH—(CH$_2$)$_{n3}$—]$_x$—(CH$_2$)$_{n1}$—CH$_3$;
with the proviso that at least one of -A, —B, or —C is
—O(O)C—(CH$_2$)$_7$—[—CH=CH—(CH$_2$)$_{n3}$—]$_x$—(CH$_2$)$_{n1}$—CH$_3$.

In the above formula:
R' is a straight or branched chain alkyl or alkenyl group;
n1 is an integer equal to or greater than 0 (typically 0 to 6; more typically 0, 3, 6);
n3 is an integer equal to or greater than 0 (typically 1); and
x is an integer equal to or greater than 1 (typically 1 to 6, more typically 1 to 3).

In exemplary embodiments, the starting composition comprises one or more C18 fatty acids, for example, oleic acid (i.e., 9-octadecenoic acid), linoleic acid (i.e., 9, 12-octadecadienoic acid), and linolenic acid (i.e., 9, 12, 15-octadecatrienoic acid).

In other exemplary embodiments, the starting composition comprises one or more C18 fatty esters, for example, methyl oleate, methyl linoleate, and methyl linolenate. In yet another exemplary embodiment, the starting composition comprises an unsaturated glyceride comprising Δ9 fatty acids, for example, C18 Δ9 fatty acids.

Δ9 starting compositions may be derived, for example, from vegetable oils such as soybean oil, rapeseed oil, corn oil, sesame oil, cottonseed oil, sunflower oil, canola oil, safflower oil, palm oil, palm kernel oil, linseed oil, castor oil, olive oil, peanut oil, and the like. Since these vegetable oils yield predominately in glyceride form, the oils are typically processed (e.g., by transesterification) to yield unsaturated free fatty esters, unsaturated free fatty acids, or carboxylate salts thereof. Δ9 starting materials may also be derived from tung oil which typically contains oleic acid, linoleic acid, and eleostearic acid (C18; Δ9, 11, 13) in glyceride form. Δ9 starting materials may also be derived from tail oil, fish oil, lard, and tallow.

Δ5 Starting Compositions:

Also useful as a starting composition in the methods of the present invention are Δ5 unsaturated fatty acids, esters, or salts. As used herein "Δ5" refers to unsaturated fatty acids, esters, or salts having a carbon-carbon double bond located between the 5th and 6th carbon atom in the alkene chain of the unsaturated fatty acid, ester, or salt. In some embodiments, Δ5 unsaturated fatty acids, esters, and salts have the general structure:

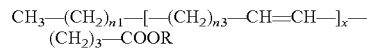

where
R is hydrogen (fatty acid), an aliphatic group (fatty monoester) or a metal ion (carboxylate salt);
n1 is an integer equal to or greater than 0 (typically 1 to 15; more typically 1, 13, or 15);
n3 is an integer equal to or greater than 0 (typically 0 to 6; more typically 0 or 6); and
x is an integer equal to or greater than 1 (typically 1 to 6, more typically 1 to 2).

The Δ5 unsaturated fatty esters may be monoesters or polyol esters (e.g., unsaturated glycerides). In many embodiments, the Δ5 unsaturated polyol esters have the general structure:

CH$_2$A-CHB—CH$_2$C where -A; —B; and —C are independently selected from
—OH;
—O(O)C—R'; and
—O(O)C—(CH$_2$)$_3$—[—CH=CH—(CH$_2$)$_{n3}$—]$_x$—(CH$_2$)$_{n1}$—CH$_3$;
with the proviso that at least one of -A, —B, or —C is
—O(O)C—(CH$_2$)$_3$—[—CH=CH—(CH$_2$)$_{n3}$—]$_x$—(CH$_2$)$_{n1}$CH$_3$.

In the above formula:
R' is a straight or branched chain alkyl or alkenyl group;
n1 is an integer equal to or greater than 0 (typically 1 to 15; more typically 1, 13, or 15);
n3 is an integer equal to or greater than 0 (typically 0 to 6; more typically 0 or 6); and
x is an integer equal to or greater than 1 (typically 1 to 6, more typically 1 to 2).

Δ5 starting compositions may be derived, for example, from meadowfoam oil which contains a twenty carbon monounsaturated fatty acid (C20:1; Δ5) in glyceride form. Δ5 starting compositions may also be derived from fish oil which typically contains eicosapentaenoic acid (C20:5; Δ5, 8, 11, 14, 17) in glyceride form.

Δ6 Starting Compositions:

Also useful as a starting composition in the methods of the present invention are Δ6 unsaturated fatty acids, esters, or salts. As used herein "Δ6" refers to unsaturated fatty acids, esters, or salts having a carbon-carbon double bond located between the 6th and 7th carbon atom in the alkene chain of the unsaturated fatty acid, ester, or salt. In some embodiments, Δ6 unsaturated fatty acids, esters, and salts have the general structure:

$$CH_3—(CH_2)_{n1}—[—(CH_2)_{n3}—CH=CH—]_x—(CH_2)_4—COOR$$

where
R is hydrogen (fatty acid), an aliphatic group (fatty monoester) or a metal ion (carboxylate salt);
n1 is an integer equal to or greater than 0 (typically 0 to 10);
n3 is an integer equal to or greater than 0; (typically 0); and
x is an integer equal to or greater than 1 (typically 1 to 6, more typically 1).

The Δ6 unsaturated fatty esters may be monoesters or polyol esters (e.g., unsaturated glycerides). In many embodiments, the Δ6 unsaturated polyol esters have the general structure:

$$CH_2A\text{-}CHB—CH_2C$$

where -A; —B; and —C are independently selected from
—OH;
—O(O)C—R'; and
—O(O)C—(CH_2)_4—[—CH=CH—(CH_2)_{n3}—]_x—(CH_2)_{n1}—CH_3;
with the proviso that at least one of -A, —B, or —C is
—O(O)C—(CH_2)_4—[—CH=CH—(CH_2)_{n3}—]_x—(CH_2)_{n1}—CH_3.

In the above formula:
R' is a straight or branched chain alkyl or alkenyl group;
n1 is an integer equal to or greater than 0 (typically 0 to 10);
n3 is an integer equal to or greater than 0; (typically 0); and
x is an integer equal to or greater than 1 (typically 1 to 6, more typically 1).

Δ6 starting compositions may be derived from coriander oil which contains an 18 carbon unsaturated fatty acid (C18:1; Δ6) in glyceride form.

Δ11 Starting Compositions:

Also useful as a starting composition in the methods of the present invention are Δ11 unsaturated fatty acids, esters, or salts. As used herein "Δ11" refers to unsaturated fatty acids, esters, or salts having a carbon-carbon double bond located between the $11^{th}$ and $12^{th}$ carbon atom in the alkene chain of the unsaturated fatty acid, ester, or salt. In some embodiments, Δ11 unsaturated fatty acids, esters, and salts have the general structure:

$$CH_3—(CH_2)_{n1}—[—(CH_2)_{n3}—CH=CH—]_x—(CH_2)_9—COOR$$

where
R is hydrogen (fatty acid), an aliphatic group (fatty monoester) or a metal ion (carboxylate salt);
n1 is an integer equal to or greater than 0 (typically 0 to 7; more typically 7);
n3 is an integer equal to or greater than 0 (typically 0); and
x is an integer equal to or greater than 1 (typically 1 to 6, more typically 1).

The Δ11 unsaturated fatty esters may be monoesters or polyol esters (e.g., unsaturated glycerides). In many embodiments, the Δ11 unsaturated polyol esters have the general structure:

$$CH_2A\text{-}CHB—CH_2C$$

where -A; —B; and —C are independently selected from
—OH;
—O(O)C—R'; and
—O(O)C—(CH_2)_9—[—CH=CH—(CH_2)_{n3}—]_x—(CH_2)_{n1}CH_3;
with the proviso that at least one of -A, —B, or —C is
—O(O)C—(CH_2)_9—[—CH=CH—(CH_2)_{n3}—]_x—(CH_2)_{n1}CH_3.

In the above formula:
R' is a straight or branched chain alkyl or alkenyl group;
n1 is an integer equal to or greater than 0 (typically 0 to 7; more typically 7);
n3 is an integer equal to or greater than 0 (typically 0); and
x is an integer equal to or greater than 1 (typically 1 to 6, more typically 1).

Sources of Δ11 starting compositions include camelina oil which contains gondoic acid (C20:1 Δ11) at approximately 15% of the fatty acid composition.

Δ13 Starting Compositions:

Also useful as a starting composition in the methods of the present invention are Δ13 unsaturated fatty acids, esters, or salts. As used herein "Δ13" refers to unsaturated fatty acids, esters, or salts having a carbon-carbon double bond located between the $13^{th}$ and $14^{th}$ carbon atom in the alkene chain of the unsaturated fatty acid, ester, or salt. In some embodiments, Δ13 unsaturated fatty acids, esters, and salts have the general structure:

$$CH_3—(CH_2)_{n1}—[—(CH_2)_{n3}—CH=CH—]_x—(CH_2)_{11}—COOR$$

where
R is hydrogen (fatty acid), an aliphatic group (fatty monoester) or a metal ion (carboxylate salt);
n1 is an integer equal to or greater than 0 (typically 7);
n3 is an integer equal to or greater than 0 (typically 0)
x is an integer equal to or greater than 1 (typically 1 to 6, more typically 1).

The Δ13 unsaturated fatty esters may be monoesters or polyol esters (e.g., unsaturated glycerides). In many embodiments, the Δ13 unsaturated polyol esters have the general structure $$CH_2A\text{-}CHB—CH_2C$$

where -A; —B; and —C are independently selected from
—OH;
—O(O)C—R'; and
—O(O)C—(CH_2)_{11}—[—CH=CH—(CH_2)_{n3}—]_x—(CH_2)_{n1}—CH_3;
with the proviso that at least one of -A, —B, or —C is
—O(O)C—(CH_2)_{11}[—CH=CH—(CH_2)_{n3}—]_x—(CH_2)_{n1}—CH_3.

In the above formula:
R' is a straight or branched chain alkyl or alkenyl group;
n1 is an integer equal to or greater than 0 (typically 7);
n3 is an integer equal to or greater than 0 (typically 0)
x is an integer equal to or greater than 1 (typically 1 to 6, more typically 1).

Sources of Δ13 starting compositions include crambe oil, fish oil, and high erucic acid rapeseed oil which are high in erucic acid (C22:1 Δ13) in glyceride form.

Other useful starting compositions include, for example, Δ8 and Δ4 starting materials. Δ4 starting materials may be obtained, for example, from fish oil which typically includes an amount of docosahexaenoic acid (C22:6; Δ4, 7, 10, 13, 16, 19). Δ8 starting materials may also be obtained from fish oil which typically includes an amount of eicosatetraenoic acid (C20:4; Δ8, 11, 14, 17).

A summary of some useful starting compositions is provided in TABLE B.

TABLE B

| Starting Composition | Description | Classification | Bond Locations |
|---|---|---|---|
| Oleic acid | C18 monounsaturated fatty acid (C18:1) | Δ9 | Δ9 |
| Linoleic acid | C18 diunsaturated fatty acid (C18:2) | Δ9 | Δ9, 12 |
| Linolenic acid | C18 triunsaturated fatty acid (C18:3) | Δ9 | Δ9, 12, 15 |
| Alkyl oleate | C18 monounsaturated fatty ester (C18:1) | Δ9 | Δ9 |
| Alkyl linoleate | C18 diunsaturated fatty ester (C18:2) | Δ9 | Δ9, 12 |
| Alkyl linolenate | C18 triunsaturated fatty ester (C18:3) | Δ9 | Δ9, 12, 15 |
| Vegetable Oil (e.g., soybean oil) | Unsaturated glycerides of C18:1, C18:2, and C18:3 fatty acids | Δ9 | Δ9 Δ9, 12 Δ9, 12, 15 |
| Tung Oil | Unsaturated glycerides of C18:1; C18:2; and C18:3 fatty acids | Δ9 | Δ9, 11, 13 Δ9 Δ9, 12 |
| Meadowfoam Oil | Unsaturated glycerides of C20:1 fatty acids. | Δ5 | Δ5 |
| Coriander Oil | Unsaturated glycerides of C18:1 fatty acids. | Δ6 | Δ6 |
| Camelina oil | Unsaturated glycerides of C20:1 fatty acids | Δ11 | Δ11 |
| Crambe Oil or High Erucic Rapeseed Oil | Unsaturated glycerides of C22:1 fatty acids | Δ13 | Δ13 |

Cross-Metathesis (Step (b)):

According to the method of the invention, the starting composition is cross-metathesized with a short-chain olefin in the presence of a metathesis catalyst to form cross-metathesis products comprising: (i) one or more olefin compounds; and (ii) one or more acid-, ester-, or carboxylate salt-functionalized alkenes having at least one carbon-carbon double bond.

Short-chain olefins are short chain length organic compounds that have at least one carbon-carbon double bond. In many embodiments, the short chain olefins have between about 4 and about 9 carbon atoms. Short chain olefins can be represented by the structure (II):

$$R^7R^8C=CR^9R^{10} \qquad (II)$$

where $R^7$, $R^8$, $R^9$, and $R^{10}$ are each, independently, hydrogen or an organic group, with the proviso that at least one of $R^7$ or $R^8$ is an organic group.

The organic group may be an aliphatic group, an alicyclic group, or an aromatic group. Organic groups may optionally include heteroatoms (e.g., O, N, or S atoms), as well as functional groups (e.g., carbonyl groups). The term aliphatic group means a saturated or unsaturated, linear or branched, hydrocarbon group. This term is used to encompass alkyl groups. The term alkyl group means a monovalent, saturated, linear, branched, or cyclic hydrocarbon group. Representative examples of alkyl groups include methyl, ethyl, propyl (n-propyl or i-propyl), butyl (n-butyl or t-butyl), pentyl, hexyl, and heptyl. An alicyclic group is an aliphatic group arranged in one or more closed ring structures. The term is used to encompass saturated (i.e., cycloparaffins) or unsaturated (cycloolefins or cycloacetylenes) groups. An aromatic or aryl group is an unsaturated cyclic hydrocarbon having a conjugated ring structure. Included within aromatic or aryl groups are those possessing both an aromatic ring structure and an aliphatic or alicyclic group.

In many embodiments, the short-chain olefin is a short-chain internal olefin. Short-chain internal olefins may be represented by structure (II):

$$R^7R^8C=CR^9R^{10} \qquad (II)$$

where $R^7$, $R^8$, $R^9$, and $R^{10}$ are each, independently, hydrogen or an organic group, with the proviso that at least one of $R^7$ or $R^8$ is an organic group, and at least one of $R^9$ or $R^{10}$ is an organic group.

Short-chain internal olefins may be symmetric or asymmetric. Symmetric short-chain internal olefins having one carbon-carbon double bond may be represented by structure (II-A):

$$R^7CH=CHR^9 \qquad (II-A)$$

where $—R^7$ and $—R^9$ are same organic group.

Representative examples of symmetric short-chain internal olefins include 2-butene, 3-hexene, and 4-octene. In some embodiments, the short-chain internal olefin is asymmetric. Representative examples of asymmetric short-chain internal olefins include 2-pentene, 2-hexene, 2-heptene, 3-heptene, 2-octene, 3-octene, 2-nonene, 3-nonene, and 4-nonene.

In many embodiments, symmetric short-chain internal olefins are preferred for cross-metathesis because the cross-metathesis products that result will include fewer products than if an asymmetric short-chain internal olefin is used for cross-metathesis. For example, as shown below, when a first double-bond containing compound (i.e., A=B) is cross-metathesized with a symmetric short-chain internal olefin (i.e., represented by C=C), two cross-metathesis products are produced. By contrast, when the same double-bond containing compound is cross-metathesized with an asymmetric short-chain internal olefin (i.e., represented by C=D), four cross-metathesis products are produced.

Metathesis of Symmetric Short-chain Internal Olefin (C=C)

$$A=B+C=C \leftrightarrow A=C+B=C$$

Metathesis of Asymmetric Short-chain Internal Olefin (C=D):

$$A=B+C=D \leftrightarrow A=C+B=C+A=D+B=D$$

In some embodiments, the short-chain olefin is an α-olefin. Alpha olefins are included in general structure (II) when $R^7$, $R^8$, and $R^9$ are all hydrogen. Representative α-olefin are shown in general structure (II-B):

$$CH_2=CH—R^{10} \qquad (II-B)$$

where $—R^{10}$ is an organic group.

Representative $—R^{10}$ groups include $—(CH_2)_n—CH_3$, where n ranges from 0 to 6. Exemplary alpha olefin compounds include 1-propene, 1-butene, 1-pentene, 1-hexene, 1-heptene, 1-octene, and 1-nonene.

Metathesis Catalysts:

Metathesis reactions proceed in the presence of a catalytically effective amount of a metathesis catalyst. The term "metathesis catalyst" includes any catalyst or catalyst system which catalyzes the olefin metathesis reaction.

Any known or future-developed metathesis catalyst may be used, alone or in combination with one or more additional catalysts, in accordance with embodiments of the present method. Exemplary metathesis catalysts include metal carbene catalysts based upon transition metals, for example, ruthenium, molybdenum, osmium, chromium, rhenium, and tungsten. In certain embodiments, the metathesis catalyst is preferably a Group 8 transition metal complex having the structure of formula (III)

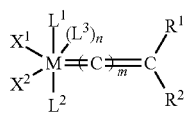
(III)

in which the various substituents are as follows:
M is a Group 8 transition metal;
$L^1$, $L^2$ and $L^3$ are neutral electron donor ligands;
n is 0 or 1, such that $L^3$ may or may not be present;
m is 0, 1, or 2;
$X^1$ and $X^2$ are anionic ligands; and
$R^1$ and $R^2$ are independently selected from hydrogen, hydrocarbyl, substituted hydrocarbyl, heteroatom-containing hydrocarbyl, substituted heteroatom-containing hydrocarbyl, and functional groups,
wherein any two or more of $X^1$, $X^2$, $L^1$, $L^2$, $L^3$, $R^1$ and $R^2$ can be taken together to form a cyclic group, and further wherein any one or more of $X^1$, $X^2$, $L^1$, $L^2$, $L^3$, $R^1$, and $R^2$ may be attached to a support.

Preferred catalysts contain Ru or Os as the Group 8 transition metal, with Ru particularly preferred.

Numerous embodiments of the catalysts useful in the reactions of the disclosure are described in more detail infra. For the sake of convenience, the catalysts are described in groups, but it should be emphasized that these groups are not meant to be limiting in any way. That is, any of the catalysts useful in the disclosure may fit the description of more than one of the groups described herein.

A first group of catalysts, then, are commonly referred to as 1$^{st}$ Generation Grubbs-type catalysts, and have the structure of formula (III). For the first group of catalysts, M and m are as described above, and n, $X^1$, $X^2$, $L^1$, $L^2$, $L^3$, $R^1$, and $R^2$ are described as follows.

For the first group of catalysts, n is 0, and $L^1$ and $L^2$ are independently selected from phosphine, sulfonated phosphine, phosphite, phosphinite, phosphonite, arsine, stibine, ether, amine, amide, imine, sulfoxide, carboxyl, nitrosyl, pyridine, substituted pyridine, imidazole, substituted imidazole, pyrazine, and thioether. Exemplary ligands are trisubstituted phosphines.

$X^1$ and $X^2$ are anionic ligands, and may be the same or different, or are linked together to form a cyclic group, typically although not necessarily a five- to eight-membered ring. In preferred embodiments, $X^1$ and $X^2$ are each independently hydrogen, halide, or one of the following groups: $C_1$-$C_2$ alkyl, $C_5$-$C_{24}$ aryl, $C_1$-$C_{20}$ alkoxy, $C_5$-$C_{24}$ aryloxy, $C_2$-$C_{20}$ alkoxycarbonyl, $C_6$-$C_{24}$ aryloxycarbonyl, $C_2$-$C_{24}$ acyl, $C_2$-$C_{24}$ acyloxy, $C_1$-$C_{20}$ alkylsulfonato, $C_5$-$C_{24}$ arylsulfonato, $C_1$-$C_{20}$ alkylsulfanyl, $C_5$-$C_{24}$ arylsulfanyl, $C_1$-$C_{20}$ alkylsulfinyl, or $C_5$-$C_{24}$ arylsulfinyl. Optionally, $X^1$ and $X^2$ may be substituted with one or more moieties selected from $C_1$-$C_{12}$ alkyl, $C_1$-$C_{12}$ alkoxy, $C_5$-$C_{24}$ aryl, and halide, which may, in turn, with the exception of halide, be further substituted with one or more groups selected from halide, $C_1$-$C_6$ alkyl, CC alkoxy, and phenyl. In more preferred embodiments, $X^1$ and $X^2$ are halide, benzoate, $C_2$-$C_6$ acyl, $C_2$-$C_6$ alkoxycarbonyl, $C_1$-$C_6$ alkyl, phenoxy, $C_1$-$C_6$ alkoxy, $C_1$-$C_6$ alkylsulfanyl, aryl, or $C_1$-$C_6$ alkylsulfonyl. In even more preferred embodiments, $X^1$ and $X^2$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethane-sulfonate. In the most preferred embodiments, $X^1$ and $X^2$ are each chloride.

$R^1$ and $R^2$ are independently selected from hydrogen, hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), heteroatom-containing hydrocarbyl (e.g., heteroatom-containing $C_1$-$C_{20}$ alkyl, $C_2$-$C_{20}$ alkenyl, $C_2$-$C_{20}$ alkynyl, $C_5$-$C_{24}$ aryl, $C_1$-$C_{24}$ alkaryl, $C_6$-$C_{24}$ aralkyl, etc.), and substituted heteroatom-containing hydrocarbyl (e.g., substituted heteroatom-containing $C_{1\text{-}20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and functional groups. $R^1$ and $R^2$ may also be linked to form a cyclic group, which may be aliphatic or aromatic, and may contain substituents and/or heteroatoms. Generally, such a cyclic group will contain 4 to 12, preferably 5, 6, 7, or 8 ring atoms.

In preferred catalysts, $R^1$ is hydrogen and $R^2$ is selected from $C_1$-$C_{20}$ alkyl, $C_2$-$C_{20}$ alkenyl, and $C_5$-$C_{24}$ aryl, more preferably $C_1$-$C_6$ alkyl, $C_2$—C alkenyl, and $C_5$-$C_{14}$ aryl. Still more preferably, $R^2$ is phenyl, vinyl, methyl, isopropyl, or t-butyl, optionally substituted with one or more moieties selected from $C_1$-$C_6$ alkyl, $C_1$-$C_6$ alkoxy, phenyl, and a functional group Fn as defined earlier herein. Most preferably, $R^2$ is phenyl or vinyl substituted with one or more moieties selected from methyl, ethyl, chloro, bromo, iodo, fluoro, nitro, dimethylamino, methyl, methoxy, and phenyl. Optimally, $R^2$ is phenyl or —C=$C(CH_3)_2$.

Any two or more (typically two, three, or four) of $X^1$, $X^2$, $L^1$, $L^2$, $L^3$, $R^1$, and $R^2$ can be taken together to form a cyclic group, as disclosed, for example, in U.S. Pat. No. 5,312,940 to Grubbs et al. When any of $X^1$, $X^2$, $L^1$, $L^2$, $L^3$, $R^1$, and $R^2$ are linked to form cyclic groups, those cyclic groups may contain 4 to 12, preferably 4, 5, 6, 7 or 8 atoms, or may comprise two or three of such rings, which may be either fused or linked. The cyclic groups may be aliphatic or aromatic, and may be heteroatom-containing and/or substituted. The cyclic group may, in some cases, form a bidentate ligand or a tridentate ligand. Examples of bidentate ligands include, but are not limited to, bisphosphines, dialkoxides, alkyldiketonates, and aryldiketonates.

A second group of catalysts, commonly referred to as 2$^{nd}$ Generation Grubbs-type catalysts, have the structure of formula (III), wherein $L^1$ is a carbene ligand having the structure of formula (IV)

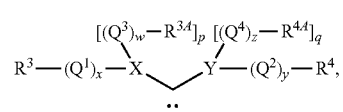
(IV)

such that the complex may have the structure of formula (V)

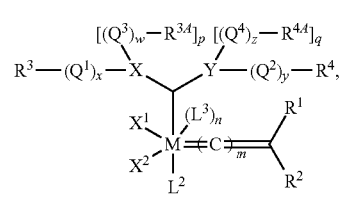
(V)

wherein M, m, n, $X^1$, $X^2$, $L^2$, $L^3$, $R^1$, and $R^2$ are as defined for the first group of catalysts, and the remaining substituents are as follows.

X and Y are heteroatoms typically selected from N, O, S, and P. Since O and S are divalent, p is necessarily zero when X is O or S, and q is necessarily zero when Y is O or S. However, when X is N or P, then p is 1, and when Y is N or P, then q is 1. In a preferred embodiment, both X and Y are N.

$Q^1$, $Q^2$, $Q^3$, and $Q^4$ are linkers, e.g., hydrocarbylene (including substituted hydrocarbylene, heteroatom-containing hydrocarbylene, and substituted heteroatom-containing hydrocarbylene, such as substituted and/or heteroatom-containing alkylene) or —(CO)—, and w, x, y, and z are independently zero or 1, meaning that each linker is optional. Preferably, w, x, y, and z are all zero. Further, two or more substituents on adjacent atoms within $Q^1$, $Q^2$, $Q^3$, and $Q^4$ may be linked to form an additional cyclic group.

$R^3$, $R^{3A}$, $R^4$, and $R^{4A}$ are independently selected from hydrogen, hydrocarbyl, substituted hydrocarbyl, heteroatom-containing hydrocarbyl, and substituted heteroatom-containing hydrocarbyl.

In addition, any two or more of $X^1$, $X^2$, L, $L^2$, $L^3$, $R^1$, $R^2$, $R^3$, $R^{3A}$, $R^4$, and $R^{4A}$ can be taken together to form a cyclic group, and any one or more of $X^1$, $X^2$, $L^1$, $L^2$, $L^3$, $R^1$, $R^2$, $R^3$, $R^{3A}$, $R^4$, and $R^{4A}$ may be attached to a support.

Preferably, $R^{3A}$ and $R^{4A}$ are linked to form a cyclic group so that the carbene ligand is an heterocyclic carbene and preferably an N-heterocyclic carbene, such as the N-heterocylic carbene having the structure of formula (VI):

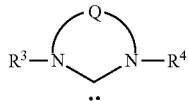

(VI)

where $R^3$ and $R^4$ are defined above, with preferably at least one of $R^3$ and $R^4$, and more preferably both $R^3$ and $R^4$, being alicyclic or aromatic of one to about five rings, and optionally containing one or more heteroatoms and/or substituents. Q is a linker, typically a hydrocarbylene linker, including substituted hydrocarbylene, heteroatom-containing hydrocarbylene, and substituted heteroatom-containing hydrocarbylene linkers, wherein two or more substituents on adjacent atoms within Q may also be linked to form an additional cyclic structure, which may be similarly substituted to provide a fused polycyclic structure of two to about five cyclic groups. Q is often, although again not necessarily, a two-atom linkage or a three-atom linkage.

Examples of N-heterocyclic carbene ligands suitable as $L^1$ thus include, but are not limited to, the following:

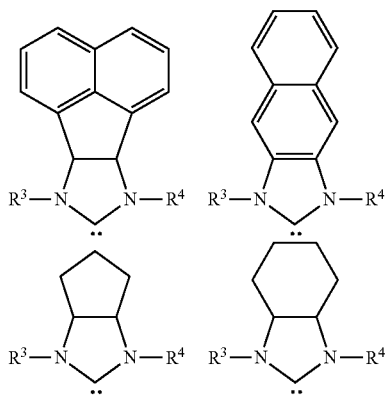

-continued

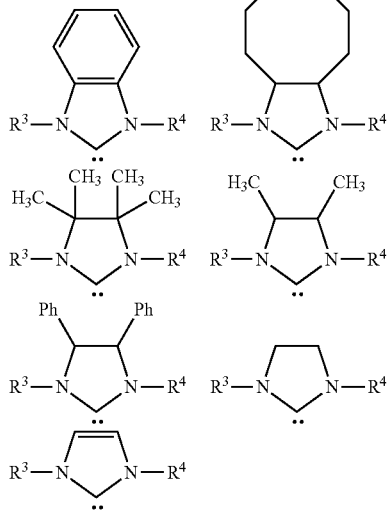

When M is ruthenium, then, the preferred complexes have the structure of formula (VII).

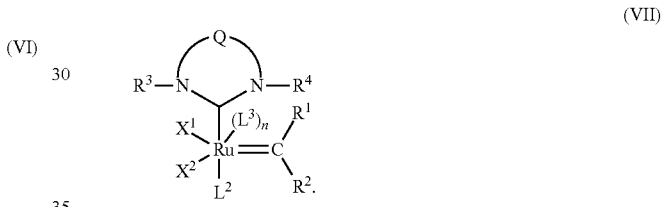

(VII)

In a more preferred embodiment, Q is a two-atom linkage having the structure —$CR^{11}R^{12}$—$CR^{13}R^{14}$— or —$CR^{11}$=$CR^{13}$—, preferably —$CR^{11}R^{12}$—$R^{13}R^{14}$—, wherein $R^{11}$, $R^{12}$, $R^{13}$, and $R^{14}$ are independently selected from hydrogen, hydrocarbyl, substituted hydrocarbyl, heteroatom-containing hydrocarbyl, substituted heteroatom-containing hydrocarbyl, and functional groups. Examples of functional groups here include carboxyl, $C_1$-$C_{20}$ alkoxy, $C_5$-$C_{24}$ aryloxy, $C_2$-$C_{20}$ alkoxycarbonyl, $C_5$-$C_{24}$ alkoxycarbonyl, $C_2$-$C_{24}$ acyloxy, $C_1$-$C_{20}$ alkylthio, $C_5$-$C_{24}$ arylthio, $C_1$-$C_{20}$ alkylsulfonyl, and $C_1$-$C_{20}$ alkylsulfinyl, optionally substituted with one or more moieties selected from $C_1$-$C_{12}$ alkyl, $C_1$-$C_{12}$ alkoxy, $C_5$-$C_{14}$ aryl, hydroxyl, sulfhydryl, formyl, and halide. $R^{11}$, $R^{12}$, $R^{13}$, and $R^{14}$ are preferably independently selected from hydrogen, $C_1$-$C_{12}$ alkyl, substituted $C_1$-$C_{12}$ alkyl, $C_1$-$C_{12}$ heteroalkyl, substituted $C_1$-$C_{12}$ heteroalkyl, phenyl, and substituted phenyl. Alternatively, any two of $R^{11}$, $R^{12}$, $R^{13}$, and $R^{14}$ may be linked together to form a substituted or unsubstituted, saturated or unsaturated ring structure, e.g., a $C_4$-$C_{12}$ alicyclic group or a $C_5$ or $C_6$ aryl group, which may itself be substituted, e.g., with linked or fused alicyclic or aromatic groups, or with other substituents.

When $R^3$ and $R^4$ are aromatic, they are typically although not necessarily composed of one or two aromatic rings, which may or may not be substituted, e.g., $R^3$ and $R^4$ may be phenyl, substituted phenyl, biphenyl, substituted biphenyl, or the like. In one preferred embodiment, $R^3$ and $R^4$ are the same and are each unsubstituted phenyl or phenyl substituted with up to three substituents selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide. Preferably, any substituents present are hydrogen, $C_1$-$C_{12}$ alkyl, $C_1$-$C_{12}$ alkoxy, $C_5$-$C_{14}$ aryl, substituted $C_5$-$C_4$ aryl, or halide. As an example, $R^3$ and $R^4$ are mesityl.

In a third group of catalysts having the structure of formula (III), M, m, n, $X^1$, $X^2$, $R^1$, and $R^2$ are as defined for the first group of catalysts, $L^1$ is a strongly coordinating neutral electron donor ligand such as any of those described for the first and second groups of catalysts, and $L^2$ and $L^3$ are weakly coordinating neutral electron donor ligands in the form of optionally substituted heterocyclic groups. Again, n is zero or 1, such that $L^3$ may or may not be present. Generally, in the third group of catalysts, $L^2$ and $L^3$ are optionally substituted five- or six-membered monocyclic groups containing 1 to 4, preferably 1 to 3, most preferably 1 to 2 heteroatoms, or are optionally substituted bicyclic or polycyclic structures composed of 2 to 5 such five- or six-membered monocyclic groups. If the heterocyclic group is substituted, it should not be substituted on a coordinating heteroatom, and any one cyclic moiety within a heterocyclic group will generally not be substituted with more than 3 substituents.

For the third group of catalysts, examples of $L^2$ and $L^3$ include, without limitation, heterocycles containing nitrogen, sulfur, oxygen, or a mixture thereof.

Examples of nitrogen-containing heterocycles appropriate for $L^2$ and $L^3$ include pyridine, bipyridine, pyridazine, pyrimidine, bipyridamine, pyrazine, 1,3,5-triazine, 1,2,4-triazine, 1,2,3-triazine, pyrrole, 2H-pyrrole, 3H-pyrrole, pyrazole, 2H-imidazole, 1,2,3-triazole, 1,2,4-triazole, indole, 3H-indole, 1H-isoindole, cyclopenta(b)pyridine, indazole, quinoline, bisquinoline, isoquinoline, bisisoquinoline, cinnoline, quinazoline, naphthyridine, piperidine, piperazine, pyrrolidine, pyrazolidine, quinuclidine, imidazolidine, picolylimine, purine, benzimidazole, bisimidazole, phenazine, acridine, and carbazole.

Examples of sulfur-containing heterocycles appropriate for $L^2$ and $L^3$ include thiophene, 1,2-dithiole, 1,3-dithiole, thiepin, benzo(b)thiophene, benzo(c)thiophene, thionaphthene, dibenzothiophene, 2H-thiopyran, 4H-thiopyran, and thioanthrene.

Examples of oxygen-containing heterocycles appropriate for $L^2$ and $L^3$ include 2H-pyran, 4H-pyran, 2-pyrone, 4-pyrone, 1,2-dioxin, 1,3-dioxin, oxepin, furan, 2H-1-benzopyran, coumarin, coumarone, chromene, chroman-4-one, isochromen-1-one, isochromen-3-one, xanthene, tetrahydrofuran, 1,4-dioxan, and dibenzofuran.

Examples of mixed heterocycles appropriate for $L^2$ and $L^3$ include isoxazole, oxazole, thiazole, isothiazole, 1,2,3-oxadiazole, 1,2,4-oxadiazole, 1,3,4-oxadiazole, 1,2,3,4-oxatriazole, 1,2,3,5-oxatriazole, 3H-1,2,3-dioxazole, 3H-1,2-oxathiole, 1,3-oxathiole, 4H-1,2-oxazine, 2H-1,3-oxazine, 1,4-oxazine, 1,2,5-oxathiazine, o-isooxazine, phenoxazine, phenothiazine, pyrano[3,4-b]pyrrole, indoxazine, benzoxazole, anthranil, and morpholine.

Preferred $L^2$ and $L^3$ ligands are aromatic nitrogen-containing and oxygen-containing heterocycles, and particularly preferred $L^2$ and $L^3$ ligands are monocyclic N-heteroaryl ligands that are optionally substituted with 1 to 3, preferably 1 or 2, substituents. Specific examples of particularly preferred $L^2$ and $L^3$ ligands are pyridine and substituted pyridines, such as 3-bromopyridine, 4-bromopyridine, 3,5-dibromopyridine, 2,4,6-tribromopyridine, 2,6-dibromopyridine, 3-chloropyridine, 4-chloropyridine, 3,5-dichloropyridine, 2,4,6-trichloropyridine, 2,6-dichloropyridine, 4-iodopyridine, 3,5-diiodopyridine, 3,5-dibromo-4-methylpyridine, 3,5-dichloro-4-methylpyridine, 3,5-dimethyl-4-bromopyridine, 3,5-dimethylpyridine, 4-methylpyridine, 3,5-diisopropylpyridine, 2,4,6-trimethylpyridine, 2,4,6-triisopropylpyridine, 4-(tert-butyl)pyridine, 4-phenylpyridine, 3,5-diphenylpyridine, 3,5-dichloro-4-phenylpyridine, and the like.

In general, any substituents present on $L^2$ and/or $L^3$ are selected from halo, $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, substituted $C_5$-$C_{24}$ heteroaryl, $C_6$-$C_{24}$ alkaryl, substituted $C_6$-$C_{24}$ alkaryl, $C_6$-$C_{24}$ heteroalkaryl, substituted $C_6$-$C_{24}$ heteroalkaryl, $C_6$-$C_{24}$ aralkyl, substituted $C_6$-$C_{24}$ aralkyl, $C_6$-$C_{24}$ heteroaralkyl, substituted $C_6$-$C_{24}$ heteroaralkyl, and functional groups, with suitable functional groups including, without limitation, $C_1$-$C_{20}$ alkoxy, $C_5$-$C_{24}$ aryloxy, $C_2$-$C_{20}$ alkylcarbonyl, $C_6$-$C_{24}$ arylcarbonyl, $C_2$-$C_{20}$ alkylcarbonyloxy, $C_6$-$C_{24}$ arylcarbonyloxy, $C_2$-$C_{20}$ alkoxycarbonyl, $C_6$-$C_{24}$ aryloxycarbonyl, halocarbonyl, $C_2$-$C_{20}$ alkylcarbonato, $C_6$-$C_{24}$ arylcarbonato, carboxy, carboxylato, carbamoyl, mono-($C_1$-$C_{20}$ alkyl)-substituted carbamoyl, di-($C_1$-$C_{20}$ alkyl)-substituted carbamoyl, di-N—($C_1$-$C_{20}$ alkyl), N—($C_5$-$C_{24}$ aryl)-substituted carbamoyl, mono-($C_5$-$C_{24}$ aryl)-substituted carbamoyl, di-($C_6$-$C_{24}$ aryl)-substituted carbamoyl, thiocarbamoyl, mono-($C_1$-$C_{20}$ alkyl)-substituted thiocarbamoyl, di-($C_1$-$C_{20}$ alkyl)-substituted thiocarbamoyl, di-N—($C_1$-$C_{20}$ alkyl)-N—($C_6$-$C_{24}$ aryl)-substituted thiocarbamoyl, mono-($C_6$-$C_{24}$ aryl)-substituted thiocarbamoyl, di-($C_6$-$C_{24}$ aryl)-substituted thiocarbamoyl, carbamido, formyl, thioformyl, amino, mono-($C_1$-$C_{20}$ alkyl)-substituted amino, di-($C_1$-$C_{20}$ alkyl)-substituted amino, mono-($C_5$-$C_{24}$ aryl)-substituted amino, di-($C_5$-$C_{24}$ aryl)-substituted amino, di-N—($C_1$-$C_{20}$ alkyl), N—($C_5$-$C_{24}$ aryl)-substituted amino, $C_2$-$C_{20}$ alkylamido, $C_6$-$C_{24}$ arylamido, imino, $C_1$-$C_{20}$ alkylimino, $C_5$-$C_{24}$ arylimino, nitro, and nitroso. In addition, two adjacent substituents may be taken together to form a ring, generally a five- or six-membered alicyclic or aryl ring, optionally containing 1 to 3 heteroatoms and 1 to 3 substituents as above.

Preferred substituents on $L^2$ and $L^3$ include, without limitation, halo, $C_{1-12}$ alkyl, substituted $C_1$-$C_{12}$ alkyl, $C_1$-$C_{12}$ heteroalkyl, substituted $C_1$-$C_{12}$ heteroalkyl, $C_5$-$C_{14}$ aryl, substituted $C_6$-$C_{14}$ aryl, $C_5$-$C_{14}$ heteroaryl, substituted $C_5$-$C_{14}$ heteroaryl, $C_6$-$C_{16}$ alkaryl, substituted $C_6$-$C_{16}$ alkaryl, $C_6$-$C_{16}$ heteroalkaryl, substituted $C_6$-$C_{16}$ heteroalkaryl, $C_6$-$C_{16}$ aralkyl, substituted $C_6$-$C_{16}$ aralkyl, $C_6$-$C_{16}$ heteroaralkyl, substituted $C_6$-$C_{16}$ heteroaralkyl, $C_1$-$C_{12}$ alkoxy, $C_5$-$C_{14}$ aryloxy, $C_2$-$C_{12}$ alkylcarbonyl, $C_6$-$C_{14}$ arylcarbonyl, $C_2$-$C_{12}$ alkylcarbonyloxy, $C_6$-$C_{14}$ arylcarbonyloxy, $C_2$-$C_{12}$ alkoxycarbonyl, $C_6$-$C_{14}$ aryloxycarbonyl, halocarbonyl, formyl, amino, mono-($C_1$-$C_{12}$ alkyl)-substituted amino, di-($C_1$-$C_{12}$ alkyl)-substituted amino, mono-($C_5$-$C_{14}$ aryl)-substituted amino, di-($C_5$-$C_{14}$ aryl)-substituted amino, and nitro.

Of the foregoing, the most preferred substituents are halo, $C_1$-$C_6$ alkyl, $C_1$-$C_6$ haloalkyl, $C_1$-$C_6$ alkoxy, phenyl, substituted phenyl, formyl, N,N-di$C_1$-$C_6$ alkyl)amino, nitro, and nitrogen heterocycles as described above (including, for example, pyrrolidine, piperidine, piperazine, pyrazine, pyrimidine, pyridine, pyridazine, etc.).

$L^2$ and $L^3$ may also be taken together to form a bidentate or multidentate ligand containing two or more, generally two, coordinating heteroatoms such as N, O, S, or P, with preferred such ligands being diimine ligands of the Brookhart type. One representative bidentate ligand has the structure of formula (VIII)

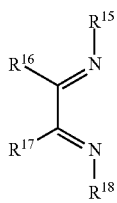
(VIII)

wherein $R^{15}$, $R^{16}$, $R^{17}$, and $R^{18}$ hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, or $C_6$-$C_{24}$ aralkyl), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, or $C_6$-$C_{24}$ aralkyl), heteroatom-containing hydrocarbyl (e.g., $C_1$-$C_{20}$ heteroalkyl, $C_5$-$C_{24}$ heteroaryl, heteroatom-containing $C_6$-$C_{24}$ aralkyl, or heteroatom-containing $C_6$-$C_{24}$ alkaryl), or substituted heteroatom-containing hydrocarbyl (e.g., substituted $C_1$-$C_{20}$ heteroalkyl, $C_5$-$C_{24}$ heteroaryl, heteroatom-containing $C_6$-$C_{24}$ aralkyl, or heteroatom-containing $C_6$-$C_{24}$ alkaryl), or (1) $R^{15}$ and $R^{16}$, (2) $R^{17}$ and $R^{18}$, (3) $R^{16}$ and $R^{17}$, or (4) both $R^{15}$ and $R^{16}$, and $R^{17}$ and $R^{18}$, may be taken together to form a ring, i.e., an N-heterocycle. Preferred cyclic groups in such a case are five- and six-membered rings, typically aromatic rings.

In a fourth group of catalysts that have the structure of formula (III), two of the substituents are taken together to form a bidentate ligand or a tridentate ligand. Examples of bidentate ligands include, but are not limited to, bisphosphines, dialkoxides, alkyldiketonates, and aryldiketonates. Specific examples include —P(Ph)$_2$CH$_2$CH$_2$P(Ph)$_2$-, —As(Ph)$_2$CH$_2$CH$_2$As(Ph)$_2$-, —P(Ph)$_2$CH$_2$CH$_2$C(CF$_3$)$_2$—, binaphtholate dianions, pinacolate dianions, —P(CH$_3$)$_2$(CH$_2$)$_2$P(CH$_3$)$_2$—, and —OC(CH$_3$)$_2$(CH$_3$)$_2$CO—. Preferred bidentate ligands are —P(Ph)$_2$ CH$_2$CH$_2$P(Ph)$_2$- and —P(CH$_3$)$_2$(CH$_2$)$_2$P(CH$_3$)$_2$—. Tridentate ligands include, but are not limited to, (CH$_3$)$_2$ NCH$_2$CH$_2$P(Ph)CH$_2$CH$_2$N (CH$_3$)$_2$. Other preferred tridentate ligands are those in which any three of $X^1$, $X^2$, $L^1$, $L^2$, $L^3$, $R^1$, and $R^2$ (e.g., $X^1$, $L^1$, and $L^2$) are taken together to be cyclopentadienyl, indenyl, or fluorenyl, each optionally substituted with $C_2$-$C_{20}$ alkenyl, $C_2$-$C_{20}$ alkynyl, $C_1$-$C_{20}$ alkyl, $C_5$-$C_{20}$ aryl, $C_1$-$C_{20}$ alkoxy, $C_2$-$C_{20}$ alkenyloxy, $C_2$-$C_{20}$ alkynyloxy, $C_6$-$C_{20}$ aryloxy, $C_2$-$C_{20}$ alkoxycarbonyl, $C_1$-$C_{20}$ alkylthio, $C_1$-$C_{20}$ alkylsulfonyl, or $C_1$-$C_{20}$ alkylsulfinyl, each of which may be further substituted with $C_1$-$C_6$ alkyl, halide, $C_1$-$C_6$ alkoxy or with a phenyl group optionally substituted with halide, $C_1$-$C_6$ alkyl, or $C_1$-$C_6$ alkoxy. More preferably, in compounds of this type, X, $L^1$, and $L^2$ are taken together to be cyclopentadienyl or indenyl, each optionally substituted with vinyl, $C_1$-$C_0$ alkyl, $C_5$-$C_{20}$ aryl, $C_1$-$C_{10}$ carboxylate, $C_2$-$C_{10}$ alkoxycarbonyl, $C_1$-$C_{10}$ alkoxy, or $C_5$-$C_{20}$ aryloxy, each optionally substituted with $C_1$-$C_6$ alkyl, halide, $C_1$-$C_6$ alkoxy or with a phenyl group optionally substituted with halide, $C_1$-$C_6$ alkyl or $C_1$-$C_6$ alkoxy. Most preferably, X, $L^1$ and $L^2$ may be taken together to be cyclopentadienyl, optionally substituted with vinyl, hydrogen, methyl, or phenyl. Tetradentate ligands include, but are not limited to O$_2$C(CH$_2$)$_2$P(Ph)(CH$_2$)$_2$P(Ph)(CH$_2$)$_2$CO$_2$, phthalocyanines, and porphyrins.

Complexes wherein $L^2$ and $R^2$ are linked are examples of the fourth group of catalysts, and are commonly called "Grubbs-Hoveyda" catalysts. Examples of Grubbs-Hoveyda-type catalysts include the following:

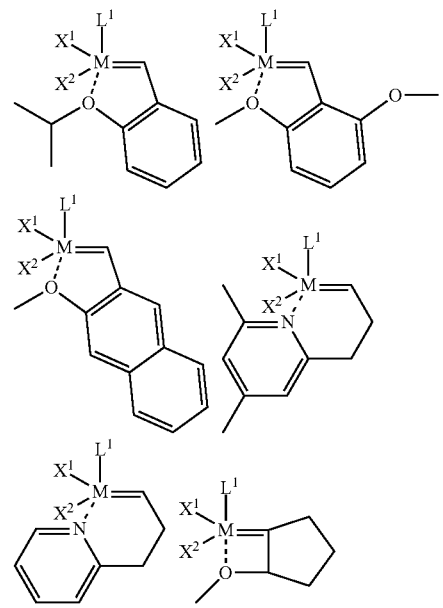

wherein $L^1$, $X^1$, $X^2$, and M are as described for any of the other groups of catalysts.

In addition to the catalysts that have the structure of formula (III), as described above, other transition metal carbene complexes include, but are not limited to:

neutral ruthenium or osmium metal carbene complexes containing metal centers that are formally in the +2 oxidation state, have an electron count of 16, are penta-coordinated, and are of the general formula (IX);

neutral ruthenium or osmium metal carbene complexes containing metal centers that are formally in the +2 oxidation state, have an electron count of 18, are hexa-coordinated, and are of the general formula (X);

cationic ruthenium or osmium metal carbene complexes containing metal centers that are formally in the +2 oxidation state, have an electron count of 14, are tetra-coordinated, and are of the general formula (XI); and cationic ruthenium or osmium metal carbene complexes containing metal centers that are formally in the +2 oxidation state, have an electron count of 14, are tetra-coordinated, and are of the general formula (XII)

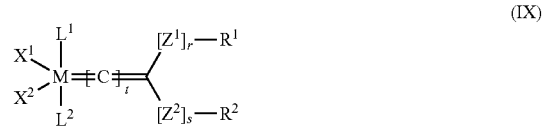
(IX)

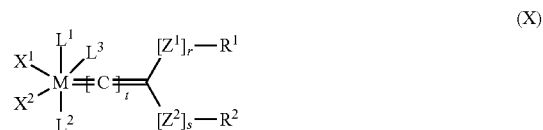
(X)

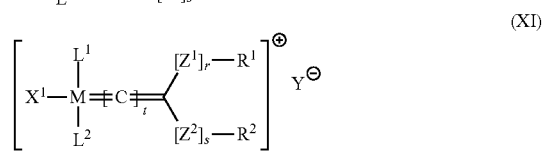
(XI)

-continued

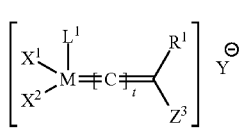
(XII)

wherein: $X^1$, $X^2$, $L^1$, $L^2$, n, $L^3$, $R^1$, and $R^2$ are as defined for any of the previously defined four groups of catalysts; r and s are independently zero or 1; t is an integer in the range of zero to 5;

Y is any non-coordinating anion (e.g., a halide ion, $BF_4^-$, etc.); $Z^1$ and $Z^2$ are independently selected from —O—, —S—, —$NR^2$—, —$PR^2$—, —P(=O)$R^2$—, —P(O$R^2$)—, —P(=O)(O$R^2$)—, —C(=O)—, —C(=O)O—, —OC(=O)—, —OC(=O)O—, —S(=O)—, and —S(=O)$_2$—; $Z^3$ is any cationic moiety such as —P($R^2$)$_3^+$ or —N($R^2$)$_3^+$; and any two or more of $X^1$, $X^2$, $L^1$, $L^2$, $L^3$, n, $Z^1$, $Z^2$, $Z^3$, $R^1$, and $R^2$ may be taken together to form a cyclic group, e.g., a multidentate ligand, and wherein any one or more of $X^1$, $X^2$, $L^1$, $L^2$, n, $L^3$, $Z^1$, $Z^2$, $Z^3$, $R^1$, and $R^2$ may be attached to a support.

Other suitable complexes include Group 8 transition metal carbenes bearing a cationic substituent, such as are disclosed in U.S. Pat. No. 7,365,140 (Piers et al.) having the general structure (XIII):

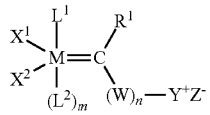
(XIII)

wherein:
M is a Group 8 transition metal;
$L^1$ and $L^2$ are neutral electron donor ligands;
X and $X^2$ are anionic ligands;
$R^1$ is hydrogen, $C_1$-$C_{12}$ hydrocarbyl, or substituted $C_1$-$C_{12}$ hydrocarbyl;
W is an optionally substituted and/or heteroatom-containing $C_1$-$C_{20}$ hydrocarbylene linkage;
Y is a positively charged Group 15 or Group 16 element substituted with hydrogen, $C_1$-$C_{12}$ hydrocarbyl, substituted $C_1$-$C_{12}$ hydrocarbyl; heteroatom-containing $C_1$-$C_{12}$ hydrocarbyl, or substituted heteroatom-containing hydrocarbyl;
$Z^-$ is a negatively charged counterion;
m is zero or 1; and
n is zero or 1;
wherein any two or more of $L^1$, $L^2$, $X^1$, $X^2$, $R^1$, W, and Y can be taken together to form a cyclic group.

Each of M, $L^1$, $L^2$, $X^1$ and $X^2$ in structure (XIII) may be as previously defined herein.

W is an optionally substituted and/or heteroatom-containing $C_1$-$C_{20}$ hydrocarbylene linkage, typically an optionally substituted $C_1$-$C_{12}$ alkylene linkage, e.g., —(CH$_2$)$_i$— where i is an integer in the range of 1 to 12 inclusive and any of the hydrogen atoms may be replaced with a non-hydrogen substituent as described earlier herein with regard to the definition of the term "substituted." The subscript n is zero or 1, meaning that W may or may not be present. In a preferred embodiment, n is zero.

Y is a positively charged Group 15 or Group 16 element substituted with hydrogen, $C_1$-$C_{12}$ hydrocarbyl, substituted $C_1$-$C_{12}$ hydrocarbyl, heteroatom-containing $C_1$-$C_{12}$ hydrocarbyl, or substituted heteroatom-containing hydrocarbyl. Preferably, Y is a $C_1$-$C_{12}$ hydrocarbyl-substituted, positively charged Group 15 or Group 16 element. Representative Y groups include P($R^2$)$_3$, P($R^2$)$_3$, As($R^2$)$_3$, S($R^2$)$_2$, O($R^2$)$_2$, where the $R^2$ are independently selected from $C_1$-$C_{12}$ hydrocarbyl; within these, preferred Y groups are phosphines of the structure P($R^2$)$_3$ wherein the $R^2$ are independently selected from $C_1$-$C_{12}$ alkyl and aryl, and thus include, for example, methyl, ethyl, n-propyl, isopropyl, n-butyl, isobutyl, t-butyl, cyclopentyl, cyclohexyl, and phenyl. Y can also be a heterocyclic group containing the positively charged Group 15 or Group 16 element. For instance, when the Group or Group 16 element is nitrogen, Y may be an optionally substituted pyridinyl, pyrazinyl, or imidazolyl group.

$Z^-$ is a negatively charged counterion associated with the cationic complex, and may be virtually any anion, so long as the anion is inert with respect to the components of the complex and the reactants and reagents used in the metathesis reaction catalyzed. Preferred $Z^-$ moieties are weakly coordinating anions, such as, for instance, [B(C$_6$F$_5$)$_4$]$^-$, [BF$_4$]$^-$, [B(C$_6$H$_6$)$_4$]$^-$, [CF$_3$S(O)$_3$]$^-$, [PF$_6$]$^-$, [SbF$_6$]$^-$, [AlCl$_4$]$^-$, [FSO$_3$]$^-$, [CB$_{11}$H$_6$Cl$_6$]$^-$, [CB$_{11}$H$_6$Br$_6$]$^-$, and [SO$_3$F:SbF$_5$]$^-$. Preferred anions suitable as Z are of the formula B($R^{15}$)$_4^-$ where $R^{15}$ is fluoro, aryl, or perfluorinated aryl, typically fluoro or perfluorinated aryl. Most preferred anions suitable as $Z^-$ are BF$_4^-$ and B(C$_6$F$_5$)$^-$, optimally the latter.

It should be emphasized that any two or more of $X^1$, $X^2$, $L^1$, $L^2$, $R^1$, W, and Y can be taken together to form a cyclic group, as disclosed, for example, in U.S. Pat. No. 5,312,940 to Grubbs et al. When any of $X^1$, $X^2$, $L^1$, $L^2$, $R^1$, W, and Y are linked to form cyclic groups, those cyclic groups may be five- or six-membered rings, or may comprise two or three five- or six-membered rings, which may be either fused or linked. The cyclic groups may be aliphatic or aromatic, and may be heteroatom-containing and/or substituted, as explained in part (1) of this section.

One group of exemplary catalysts encompassed by the structure of formula (XIII) are those wherein m and n are zero, such that the complex has the structure of formula (XIV)

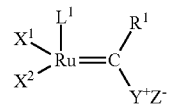
(XIV)

Possible and preferred $X^1$, $X^2$, and $L^1$ ligands are as described earlier with respect to complexes of formula (I), as are possible and preferred $Y^+$ and $Z^-$ moieties. M is Ru or Os, preferably Ru, and $R^1$ is hydrogen or $C_1$-$C_{12}$ alkyl, preferably hydrogen.

In formula (XIV)-type catalysts, $L^1$ is preferably a heteroatom-containing carbene ligand having the structure of formula (XV)

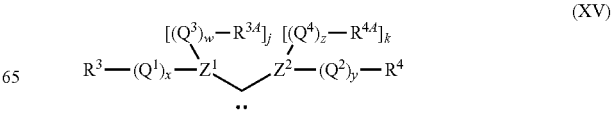
(XV)

such that complex (XIV) has the structure of formula (XVI)

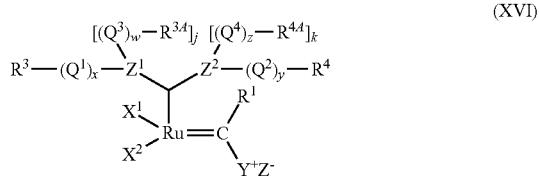

wherein $X^1$, $X^2$, $R^1$, $R^2$, Y, and Z are as defined previously, and the remaining substituents are as follows:

$Z^1$ and $Z^2$ are heteroatoms typically selected from N, O, S, and P. Since O and S are divalent, j is necessarily zero when $Z^1$ is O or S, and k is necessarily zero when $Z^2$ is O or S. However, when $Z^1$ is N or P, then j is 1, and when $Z^2$ is N or P, then k is 1. In a preferred embodiment, both $Z^1$ and $Z^2$ are N.

$Q^1$, $Q^2$, $Q^3$, and $Q^4$ are linkers, e.g., $C_1$-$C_{12}$ hydrocarbylene, substituted $C_1$-$C_{12}$ hydrocarbylene, heteroatom-containing $C_1$-$C_{12}$ hydrocarbylene, substituted heteroatom-containing $C_1$-$C_{12}$ hydrocarbylene, or —(CO)—, and w, x, y, and z are independently zero or 1, meaning that each linker is optional. Preferably, w, x, y, and z are all zero.

$R^3$, $R^{3A}$, $R^4$, and $R^{4A}$ are independently selected from hydrogen, hydrogen, $C_1$-$C_{20}$ hydrocarbyl, substituted $C_1$-$C_{20}$ hydrocarbyl, heteroatom-containing $C_1$-$C_{20}$ hydrocarbyl, and substituted heteroatom-containing $C_1$-$C_{20}$ hydrocarbyl.

Preferably, w, x, y, and z are zero, $Z^1$ and $Z^1$ are N, and $R^{3A}$ and $R^{4A}$ are linked to form -Q-, such that the complex has the structure of formula (XVII)

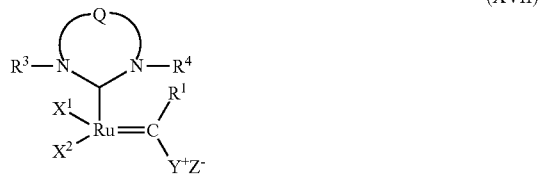

wherein $R^3$ and $R^4$ are defined above, with preferably at least one of $R^3$ and $R^4$, and more preferably both $R^3$ and $R^4$, being alicyclic or aromatic of one to about five rings, and optionally containing one or more heteroatoms and/or substituents. Q is a linker, typically a hydrocarbylene linker, including $C_1$-$C_{12}$ hydrocarbylene, substituted $C_1$-$C_1$ hydrocarbylene, heteroatom-containing $C_1$-$C_{12}$ hydrocarbylene, or substituted heteroatom-containing $C_1$-$C_{12}$ hydrocarbylene linker, wherein two or more substituents on adjacent atoms within Q may be linked to form an additional cyclic structure, which may be similarly substituted to provide a fused polycyclic structure of two to about five cyclic groups. Q is often, although not necessarily, a two-atom linkage or a three-atom linkage, e.g., —$CH_2$—$CH_2$—, —CH(Ph)-CH(Ph)- where Ph is phenyl; =CR—N=, giving rise to an unsubstituted (when R=H) or substituted (R=other than H) triazolyl group; or —$CH_2$—$SiR_2$—$CH_2$— (where R is H, alkyl, alkoxy, etc.).

In a more preferred embodiment, Q is a two-atom linkage having the structure —$CR^8R^9$—$CR^{10}R^{11}$— or —$CR^8$=$CR^{10}$—, preferably —$CR^8R^9$—$CR^{10}R^{11}$—, wherein $R^8$, $R^9$, $R^{10}$, and $R^{11}$ are independently selected from hydrogen, $C_1$-$C_{12}$ hydrocarbyl, substituted $C_1$-$C_{12}$ hydrocarbyl, heteroatom-containing $C_1$-$C_{12}$ hydrocarbyl, substituted heteroatom-containing $C_1$-$C_{12}$ hydrocarbyl, and functional groups as defined in part (I) of this section. Examples of functional groups here include carboxyl, $C_1$-$C_{20}$ alkoxy, $C_5$-$C_{20}$ aryloxy, $C_2$-$C_{20}$ alkoxycarbonyl, $C_2$-$C_{20}$ alkoxycarbonyl, $C_2$-$C_{20}$ acyloxy, $C_1$-$C_{20}$ alkylthio, $C_5$-$C_{20}$ arylthio, $C_1$-$C_{20}$ alkylsulfonyl, and $C_1$-$C_{20}$ alkylsulfinyl, optionally substituted with one or more moieties selected from $C_{1-10}$ alkyl, $C_1$-$C_{10}$ alkoxy, $C_5$-$C_{20}$ aryl, hydroxyl, sulfhydryl, formyl, and halide. Alternatively, any two of $R^8$, $R^9$, $R^{10}$, and $R^{11}$ may be linked together to form a substituted or unsubstituted, saturated or unsaturated ring structure, e.g., a $C_4$-$C_{12}$ alicyclic group or a C or C aryl group, which may itself be substituted, e.g., with linked or fused alicyclic or aromatic groups, or with other substituents.

Further details concerning such formula (XIII) complexes, as well as associated preparation methods, may be obtained from U.S. Pat. No. 7,365,140, herein incorporated by reference.

As is understood in the field of catalysis, suitable solid supports for any of the catalysts described herein may be of synthetic, semi-synthetic, or naturally occurring materials, which may be organic or inorganic, e.g., polymeric, ceramic, or metallic. Attachment to the support will generally, although not necessarily, be covalent, and the covalent linkage may be direct or indirect, if indirect, typically through a functional group on a support surface.

Non-limiting examples that may be used in the reactions of the disclosure include the following, some of which for convenience are identified throughout this disclosure by reference to their molecular weight:

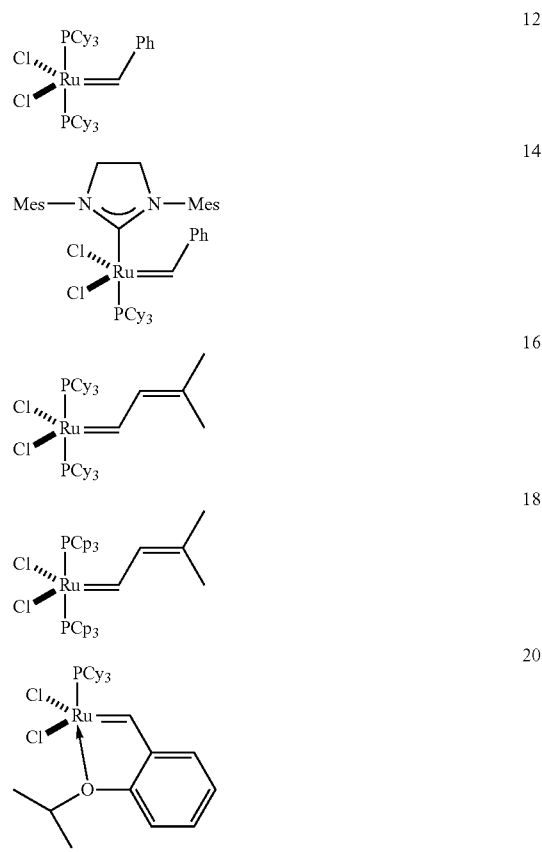

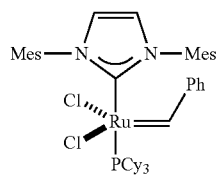
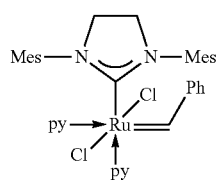
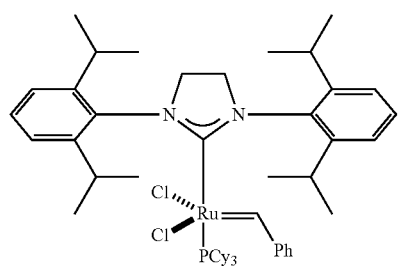
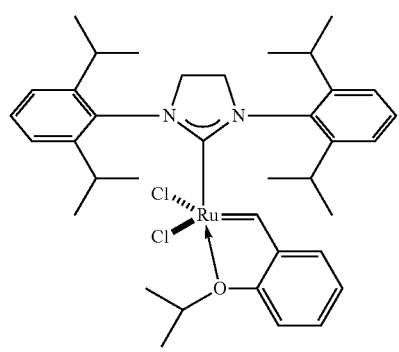
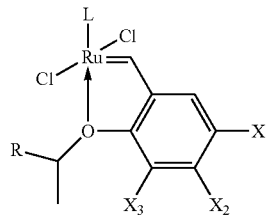
where
L = PCy$_3$, sIMes, Mes, Phobane
X = H, NO$_2$, SO$_2$N(CH$_3$)$_2$
X$_2$ = H, N$^+$(C$_2$H$_3$)$_2$, CH$_3$
X$_3$ = H, Phenyl
R = H, alkyl, aryl, CO$_2$Me
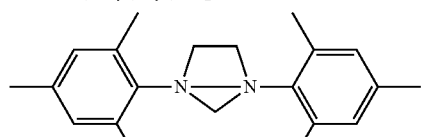
sIMes
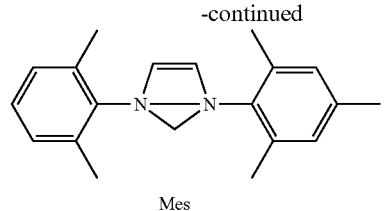
Mes
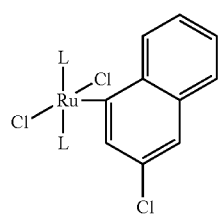
where
L = PCy$_3$, SIMes, Phobane
L = PCy$_3$, Phobane
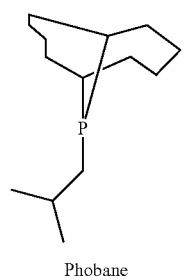
Phobane
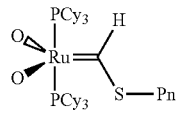
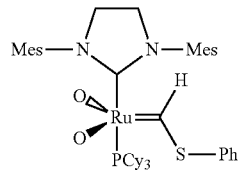
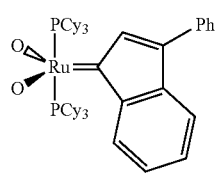
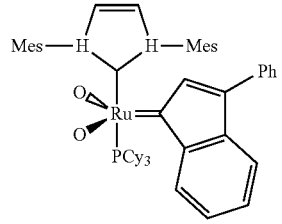

-continued
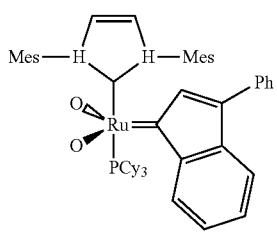
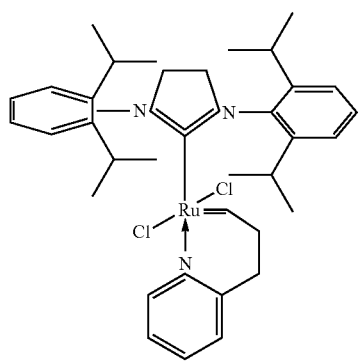
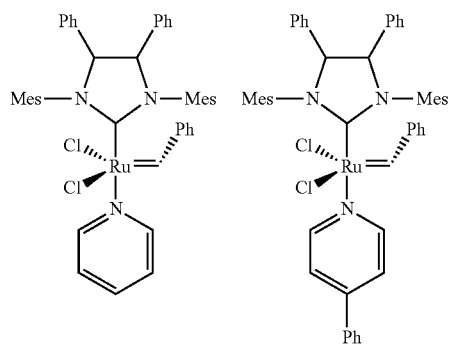
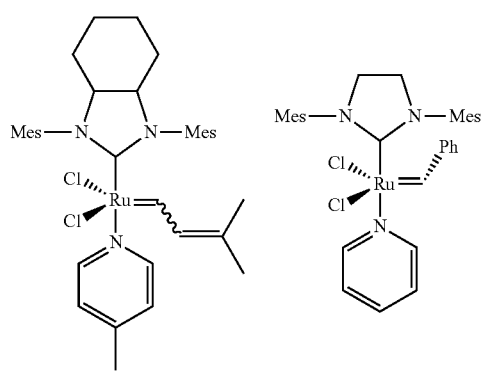
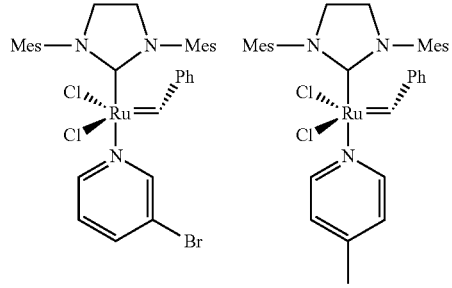
-continued
68
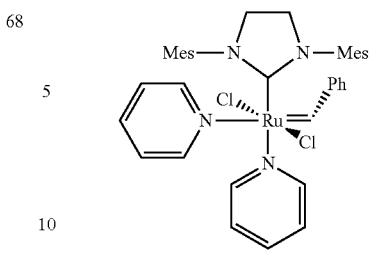
C682
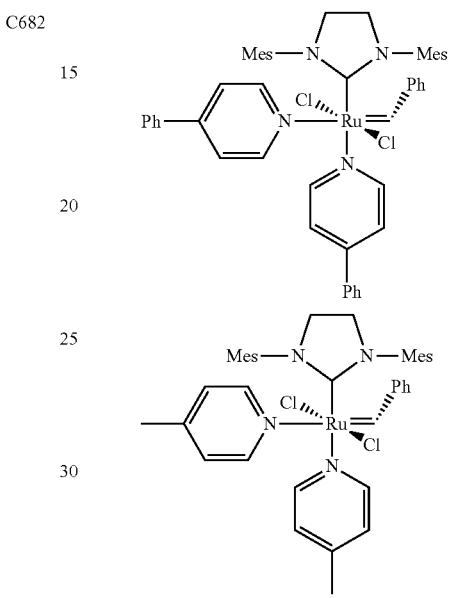
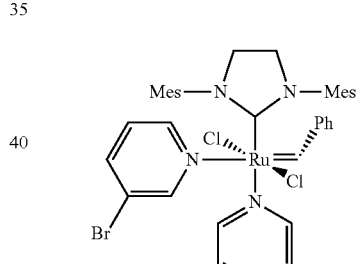
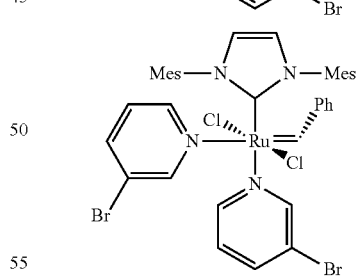
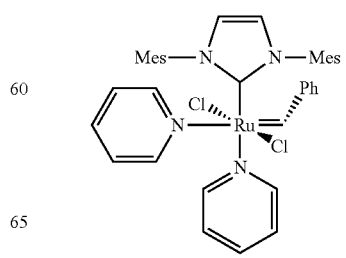

C827
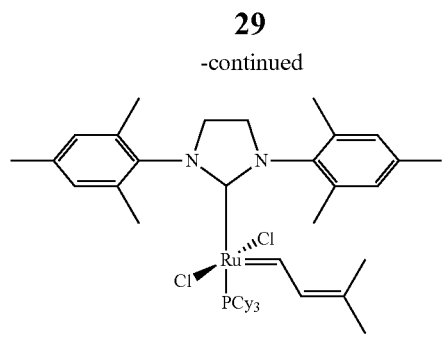
C859
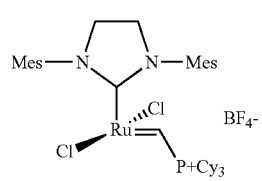
C841-n
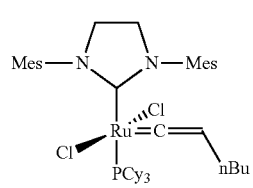
C916
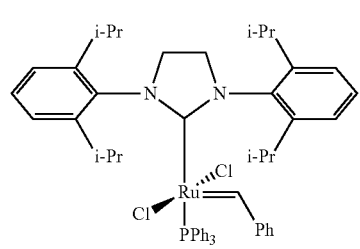
C965-p
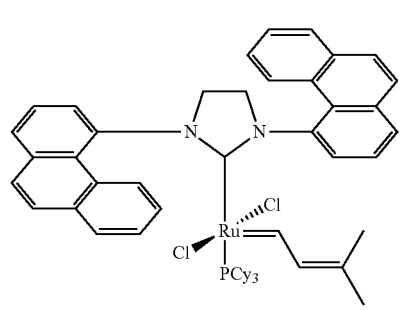
C727
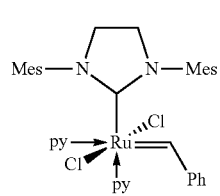
C577
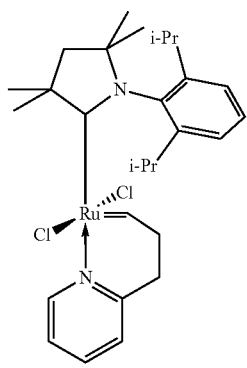
C646
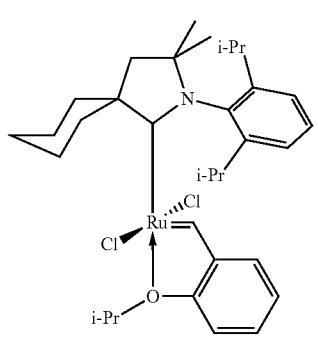
C701
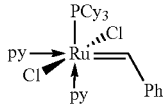
C767-m
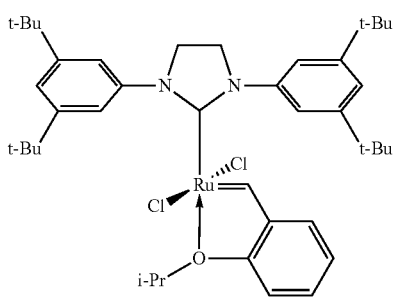
C811
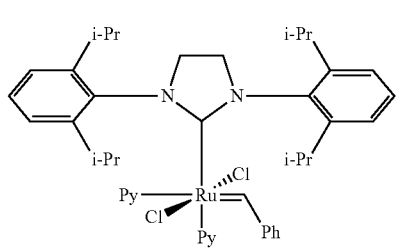
C801
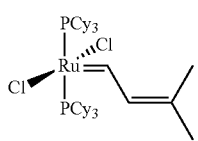

C838
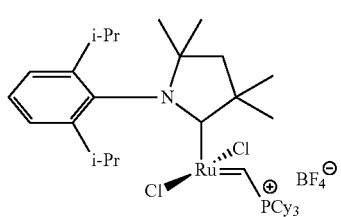
C712
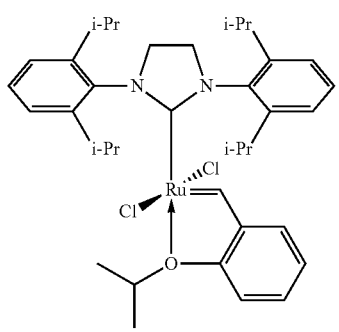
C933
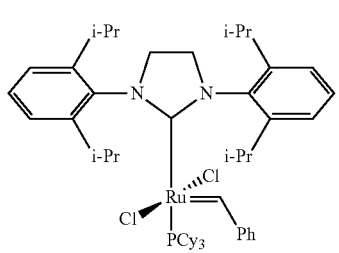
C824
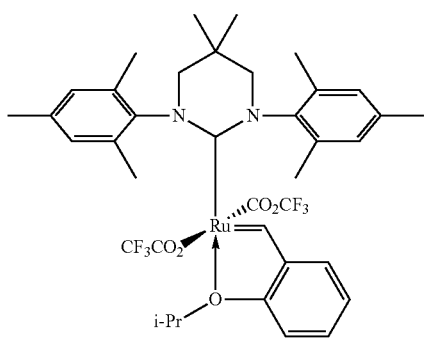
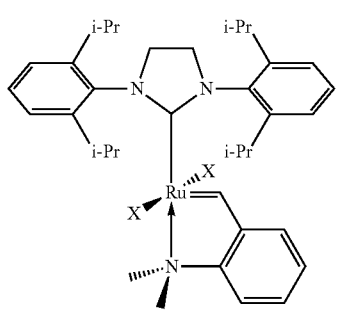
C697 (X = Cl)
C785 (X = Br)
C879 (X = I)
C601
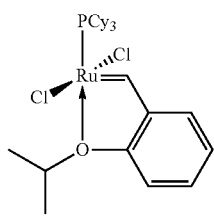
C848
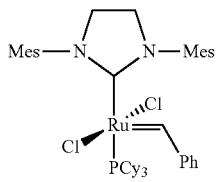
C831
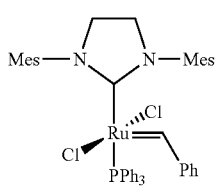
C627
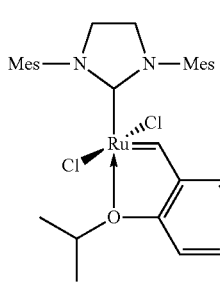
C672
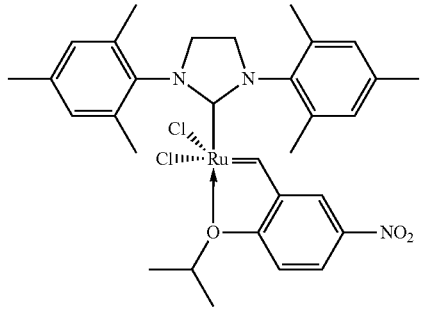
C657
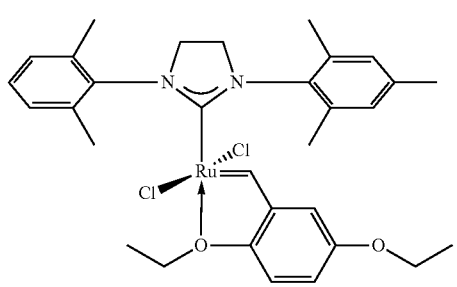

-continued
C734
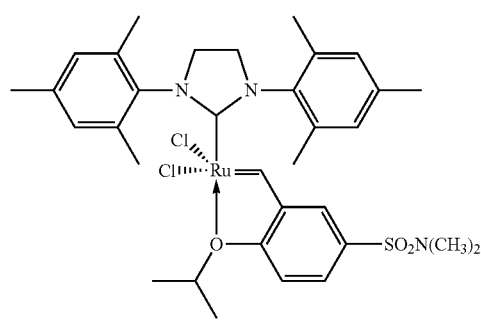
C767
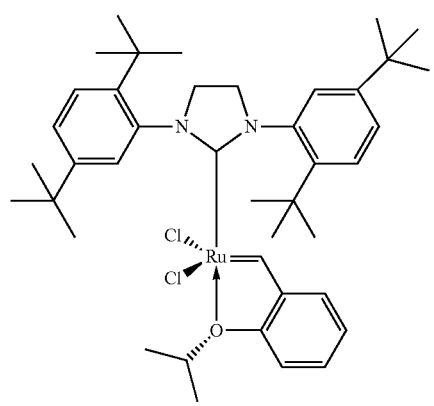
C809
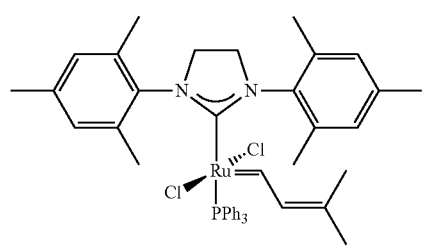
C849
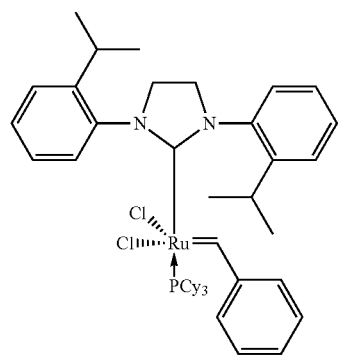
C923
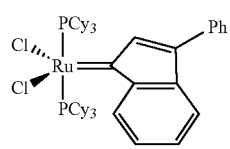
-continued
C-524
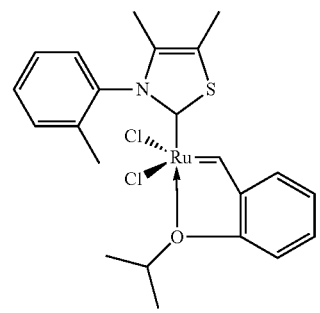
C-552
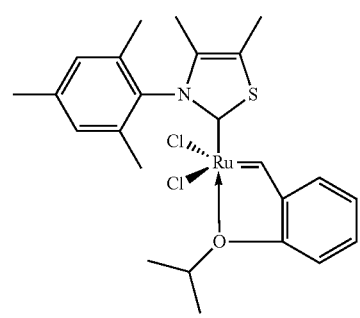
C-566
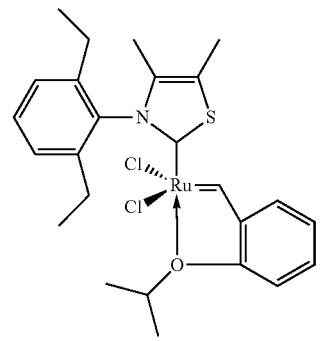
DPA1-278
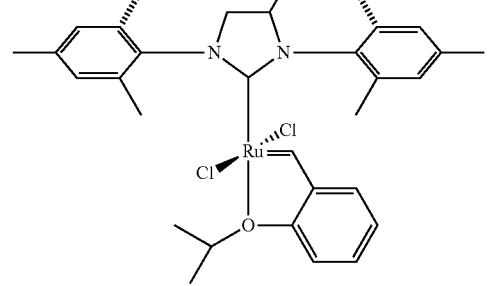

C-598
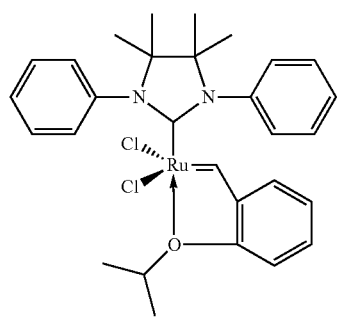
C-626
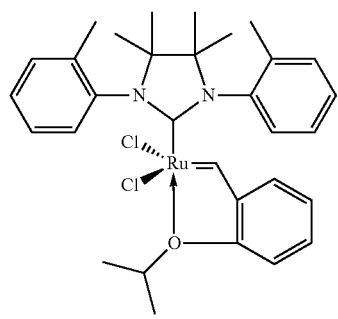
C949
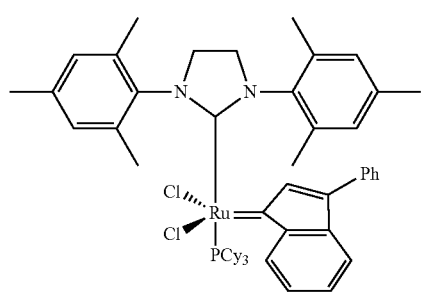
C823
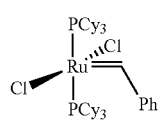
C606
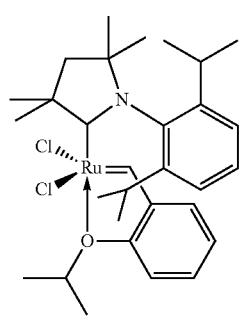
C629
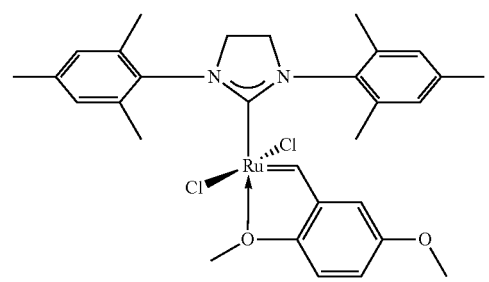
C833
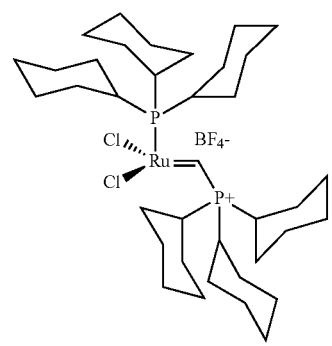
C613
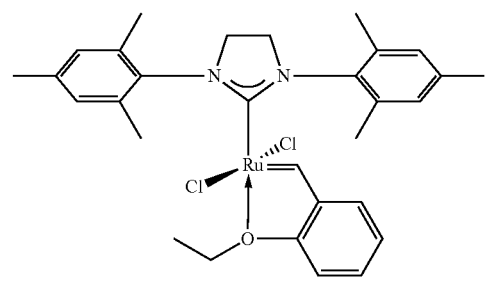
C827
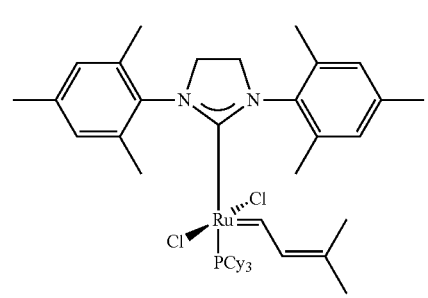
C627
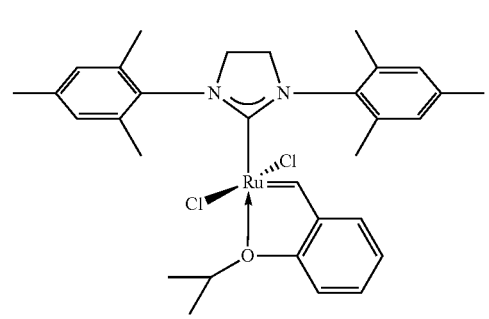

-continued
C793
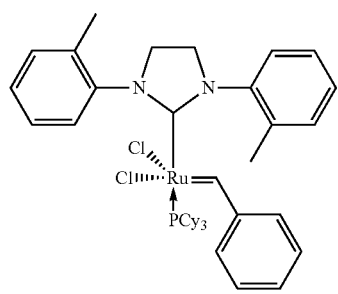
C598Cs
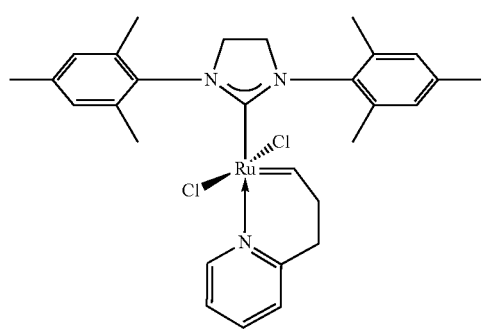
C782
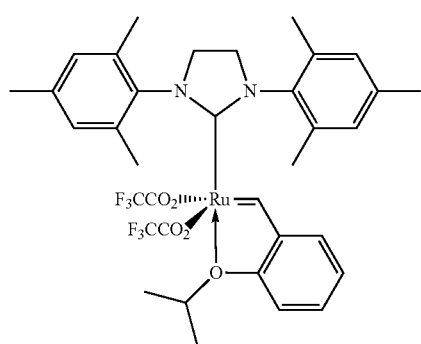
C702
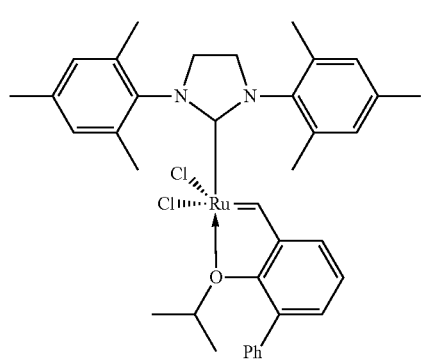
-continued
C884
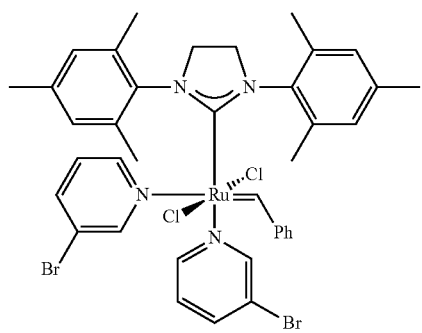
C933
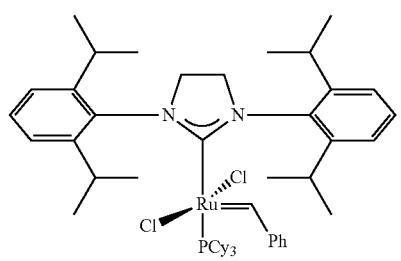
C866
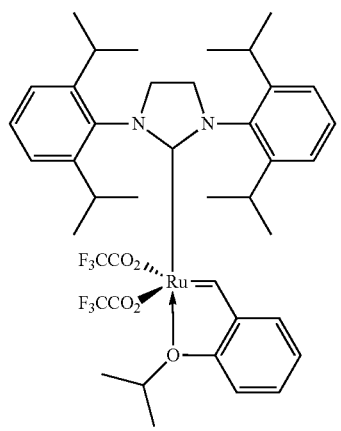
C571
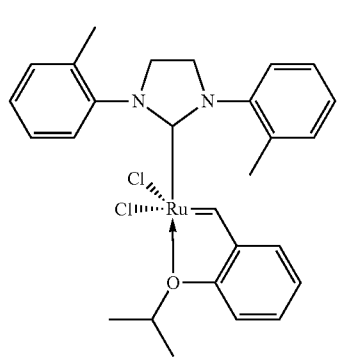

-continued

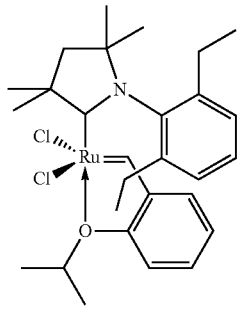

C578

In the foregoing molecular structures and formulae, Ph represents phenyl, Cy represents cyclohexane, Me represents methyl, nBu represents n-butyl, i-Pr represents isopropyl, py represents pyridine (coordinated through the N atom), and Mes represents mesityl (i.e., 2,4,6-trimethylphenyl).

Further examples of catalysts useful in the reactions of the present disclosure include the following: ruthenium (II) dichloro (3-methyl-1,2-butenylidene) bis(tricyclopentylphosphine) (C716); ruthenium (II) dichloro (3-methyl-1,2-butenylidene) bis(tricyclohexylphosphine) (C801); ruthenium (II) dichloro (phenylmethylene) bis (tricyclohexylphosphine) (C823); ruthenium (II) [1,3-bis-(2,4,6-trimethylphenyl)-2-imidazolidinylidene) dichloro (phenylmethylene) (triphenylphosphine) (C830), and ruthenium (II) dichloro (vinyl phenylmethylene) bis(tricyclohexylphosphine) (C835); ruthenium (II) dichloro (tricyclohexylphosphine) (o-isopropoxyphenylmethylene) (C601), and ruthenium (II) (1, 3-bis-(2, 4, 6,-trimethylphenyl)-2-imidazolidinylidene) dichloro (phenylmethylene) (bis 3-bromopyridine (C884)).

Exemplary ruthenium-based metathesis catalysts include those represented by structures 12 (commonly known as Grubbs's catalyst), 14 and 16. Structures 18, 20, 22, 24, 26, 28, 60, 62, 64, 66, and 68 represent additional ruthenium-based metathesis catalysts. Catalysts C627, C682, C697, C712, and C827 represent still additional ruthenium-based catalysts. General structures 50 and 52 represent additional ruthenium-based metathesis catalysts of the type reported in *Chemical & Engineering News*; Feb. 12, 2007, at pages 37-47. In the structures, Ph is phenyl, Mes is mesityl, py is pyridine, Cp is cyclopentyl, and Cy is cyclohexyl.

Techniques for using the metathesis catalysts are known in the art (see, for example, U.S. Pat. Nos. 7,102,047; 6,794,534; 6,696,597; 6,414,097; 6,306,988; 5,922,863; 5,750,815; and metathesis catalysts with ligands in U.S. Publication No. 2007/0004917 A1), all incorporated by reference herein in their entireties. A number of the metathesis catalysts as shown are manufactured by Materia, Inc. (Pasadena, Calif.).

Additional exemplary metathesis catalysts include, without limitation, metal carbene complexes selected from the group consisting of molybdenum, osmium, chromium, rhenium, and tungsten. The term "complex" refers to a metal atom, such as a transition metal atom, with at least one ligand or complexing agent coordinated or bound thereto. Such a ligand typically is a Lewis base in metal carbene complexes useful for alkene, alkyne or alkene-metathesis. Typical examples of such ligands include phosphines, halides and stabilized carbenes. Some metathesis catalysts may employ plural metals or metal co-catalysts (e.g. a catalyst comprising a tungsten halide, a tetraalkyl tin compound, and an organoaluminum compound).

An immobilized catalyst can be used for the metathesis process. An immobilized catalyst is a system comprising a catalyst and a support, the catalyst associated with the support. Exemplary associations between the catalyst and the support may occur by way of chemical bonds or weak interactions (e.g. hydrogen bonds, donor acceptor interactions) between the catalyst, or any portions thereof, and the support or any portions thereof. Support is intended to include any material suitable to support the catalyst. Typically, immobilized catalysts are solid phase catalysts that act on liquid or gas phase reactants and products. Exemplary supports are polymers, silica, or alumina. Such an immobilized catalyst may be used in a flow process. An immobilized catalyst can simplify purification of products and recovery of the catalyst so that recycling the catalyst may be more convenient.

The metathesis process for producing industrial chemicals can be conducted under any conditions adequate to produce the desired metathesis product or products. For example, stoichiometry, atmosphere, solvent, temperature and pressure can be selected to produce a desired product and to minimize undesirable byproducts. The metathesis process may be conducted under an inert atmosphere. Similarly, if an olefin reagent is supplied as a gas, an inert gaseous diluent can be used. The inert atmosphere or inert gaseous diluent typically is an inert gas, meaning that the gas does not interact with the metathesis catalyst to substantially impede catalysis. For example, particular inert gases are selected from the group consisting of helium, neon, argon, nitrogen, and combinations thereof.

Similarly, if a solvent is used, the solvent chosen may be selected to be substantially inert with respect to the metathesis catalyst. For example, substantially inert solvents include, without limitation, aromatic hydrocarbons, such as benzene, toluene, xylenes, etc.; halogenated aromatic hydrocarbons, such as chlorobenzene and dichlorobenzene; aliphatic solvents, including pentane, hexane, heptane, cyclohexane, etc.; and chlorinated alkanes, such as dichloromethane, chloroform, dichloroethane, etc.

In certain embodiments, a ligand may be added to the metathesis reaction mixture. In many embodiments using a ligand, the ligand is selected to be a molecule that stabilizes the catalyst, and may thus provide an increased turnover number for the catalyst. In some cases the ligand can alter reaction selectivity and product distribution. Examples of ligands that can be used include Lewis base ligands, such as, without limitation, trialkylphosphines, for example tricyclohexylphosphine and tributyl phosphine; triarylphosphines, such as triphenylphosphine; diarylalkylphosphines, such as, diphenylcyclohexylphosphine; pyridines, such as 2,6-dimethylpyridine, 2,4,6-trimethylpyridine; as well as other Lewis basic ligands, such as phosphine oxides and phosphinites. Additives may also be present during metathesis that increase catalyst lifetime.

Using currently known catalysts, the metathesis processing temperature may largely be a rate-dependent variable where the temperature is selected to provide a desired product at an acceptable production rate. The selected temperature may be greater than about −40° C., may be more than about −20° C., and is generally selected to be more than about 0° C. or more than about 20° C. Generally, the process temperature may be no more than about 150° C., and may be no more than about 120° C. Thus, an exemplary temperature range for the metathesis reaction may be from about 20° C. to about 120° C. Lower temperatures can be used, for example, to minimize the production of undesired impurities or to favor a particular reaction pathway.

Any useful amount of the selected metathesis catalyst can be used in the process. For example, the molar ratio of the unsaturated polyol ester to catalyst may range from about 5:1 to about 10,000,000:1 or from about 50:1 to 500,000:1.

The metathesis process steps (i.e., step (b) and step (d)) can be conducted under any desired pressure. For example, the cross-metathesis step (b) is typically conducted at a pressure ranging from about 10 kPa to about 7000 kPa or from about 100 kPa to about 3000 kPa. In some embodiments, it is preferred to conduct the self-metathesis step (i.e., step (d)) at low pressure, for example, about 0.01 kPa to about 100 kPa, more typically about 0.01 kPa to about 50 kPa. By conducting the self-metathesis at low pressure, the low boiling point olefin products (e.g., the short-chain internal olefin or alpha olefin) that are formed during the cross-metathesis reaction can be easily separated from the higher boiling point functionalized olefin products (e.g., the one or more diacid olefins, diester olefins, or disalt olefins). This separation is advantageous for two reasons. First, in an integrated process, the separation of the short-chain internal olefin product allows this material to be recycled back to the reactor where the cross-metathesis step (i.e., step (b)) is being conducted. Second, the removal of the olefin products from the functionalized olefin products drives the equilibrium of the self-metathesis reaction (i.e., step (d)) to the formation of more functionalized olefin product. This results in a higher yield of the desired functionalized olefin product.

The metathesis reaction may be catalyzed by a system containing both a transition and a non-transition metal component. The most active and largest number of two-part catalyst systems are derived from Group VI A transition metals, for example, tungsten and molybdenum.

Separation Step (Step (c)):

After cross-metathesis with a short-chain olefin, at least a portion of the acid-, ester-, or carboxylate salt-functionalized alkene is separated from the remaining cross-metathesis products. If cross-metathesis is conducted on an unsaturated glyceride starting composition the resulting cross-metathesis products should be transesterified prior to separation. This allows the separation step to separate the ester-functionalized alkene from any ester functionalized alkane that may be present in the transesterification products.

Useful techniques for separating the acid-, ester-, or carboxylate salt-functionalized alkene from the remaining cross-metathesis products include, for example, distillation, reactive distillation, chromatography, fractional crystallization, membrane separation, liquid/liquid extraction, or a combination thereof.

In many embodiments, the acid-, ester-, or carboxylate salt-functionalized alkene can be purified to a high degree using one or more of the above-described techniques. For example, the acid-, ester-, or carboxylate salt-functionalized alkene can be purified to a level of 90% wt. or greater (e.g., 95% wt. or greater, 96% wt. or greater, 97% wt. or greater, 98% wt. or greater, 99% wt. or greater, 99.5% wt. or greater, or 99.9% wt. or greater). Using the method of the invention, a high purity functionalized alkene intermediate can be obtained using one or more conventional separation processes. Achieving a high purity functionalized alkene intermediate allows for the production of a high purity products from the methods of the invention For example, in some embodiments, the product has a purity of 90% wt. or greater (e.g., 95% wt. or greater, 96% wt. or greater, 97% wt. or greater, 98% wt. or greater, 99% wt. or greater, 99.5% wt. or greater, or 99.9% wt. or greater).

Self or Cross-Metathesis Step (Step (d)):

In some embodiments, after separation, the isolated acid-, ester-, or salt-functionalized alkene is self-metathesized in the presence of a metathesis catalyst to form a composition comprising one or more diacid alkenes, diester alkenes, or dicarboxylate salt alkenes. For example, when a Δ9 acid-functionalized starting composition is used and is cross-metathesized with 2-butene, the resulting acid-functionalized alkene has the structure HOOC—(CH$_2$)$_7$—CH=CH—CH$_3$. After separation, self-metathesis of the acid-functionalized alkene yields an unsaturated C18 diacid and 2-butene according to the formula below:

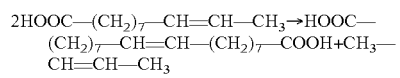

In similar fashion, when a Δ9 methyl ester-functionalized starting composition is used and is cross-metathesized with 2-butene, the resulting methyl ester-functionalized alkene has structure CH$_3$OOC—(CH$_2$)$_7$—CH=CH—CH$_3$. Self-metathesis of the ester-functionalized olefin yields an unsaturated C18 diester and 2-butene according to the formula below:

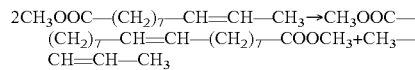

In another embodiment, a Δ5 acid-functionalized starting composition is used and is cross-metathesized with 2-butene to provide an acid-functionalized alkene having the structure HOOC—(CH$_2$)$_3$—CH=CH—CH$_3$. Self-metathesis of the acid-functionalized alkene yields an unsaturated C10 diacid and 2-butene according to the formula below:

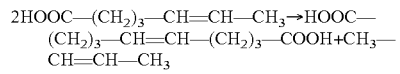

In another embodiment, a Δ6 acid-functionalized starting composition is used and is cross-metathesized with 2-butene to provide an acid-functionalized alkene having the structure HOOC—(CH$_2$)$_4$—CH=CH—CH$_3$. Self-metathesis of the ester-functionalized alkene yields an unsaturated C12 diacid and 2-butene according to the formula below:

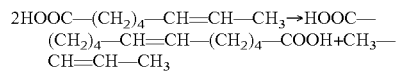

In another embodiment, a Δ13 acid-functionalized starting composition is used and is cross-metathesized with 2-butene to provide an acid-functionalized alkene having the structure HOOC—(CH$_2$)$_{11}$—CH=CH—CH$_3$. Self-metathesis of the ester-functionalized alkene yields an unsaturated C26 diacid and 2-butene according to the formula below:

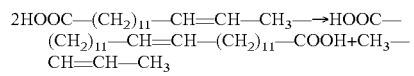

Other self-metathesis reactions would follow the above reaction scheme.

In some embodiments, after separation, the isolated acid-, ester-, or carboxylate salt-functionalized alkene is cross-metathesized with a second functionalized alkene compound in the presence of a metathesis catalyst to form a bifunctional organic compound. Exemplary bifunctional organic compounds obtainable by this method include diacids, acid/esters, acid/amines, acid/alcohols, acid/aldehydes, acid/ketones, acid/halides, acid/nitriles, as well as diesters, ester/amines, ester/alcohols, ester/aldehydes, ester/ketones, ester/halides, and ester/nitriles. In many embodiments, after cross-metathesis, the resulting bifunctional organic compound is hydrogenated in order to saturate the double-bond that is present in the bifunctional compound. For example, starting with fatty acids ☐5 and higher, alpha, omega-diacids from C7 to C18 and higher can be made. Similarly, omega-hydroxycarboxylic acids and omega-aminocarboxylic acids from C7 to C18 and higher can be made.

The second functionalized alkene compound has at least one carbon-carbon double bond and has at least one organic functional group. Examples of organic functional groups include carboxylic acids, esters, amines, amides, halogens, aldehydes, nitriles, isocyanates, ketones, epoxides, and alcohols. In many embodiments, the second functionalized alkene has the general structure:

$$R^{12}-CH=CH-(CH_2)_n-R^{13}$$

where n is 0 or an integer (typically 1 to 20);

—$R^{12}$ is hydrogen, an alkyl group, an aryl group, or —$(CH_2)_n$—$R^{13}$;

—$R^{13}$ is a functional group (typically —COOH, —$COOR^{14}$, —COH; —$COR^{14}$; —$CONH_2$; —C≡N; —$NH_2$; —OH; or —X);

—$R^{14}$ is alkyl group or an aryl group; and

—X is a halogen (typically Cl, F, Br, or 1).

Examples of second functionalized alkene compounds include 2-butene-1,4-dioic acid (HOOCCH=CHCOOH), acrylic acid (CH=CHCOOH), 2-butenoic acid ($CH_3CH$=CHCOOH), 2-pentenoic acid ($CH_3CH_2CH$=CHCOOH), 2-hexenoic acid ($CH_3CH_2CH_2CH$=CHCOOH), 3-hexenedioc acid ($HOOCCH_2CH$=$CHCH_2COOH$), the dimethyl ester of 3-hexenedioc acid ($CH_3OOCH_2CH$=$CHCH_2COOCH_3$), 3-hexenoic acid ($HOOCCH_2CH$=$CHCH_2CH_3$), the methyl ester of 3-hexenoic acid ($CH_3OOCCH_2CH$=$CHCH_2CH_3$), 3-pentenoic acid ($HOOCCH_2CH$=$CHCH_3$), methyl ester of 3-pentenoic acid ($CH_3OOCCH_2CH$=$CHCH_3$), 4-pentenoic acid, 4-hexenoic acid, 4-heptenoic acid, 4-octenoic acid and its esters, 4-octene-1,8-dioic acid and its esters, 5-hexenoic acid, 1-bromo-3 hexene, 3-butenal diethyl acetal, 5-heptenoic acid, 5-octenoic acid and its esters, 5-decene-1, 10-dioic acid and its esters, 6-heptenoic acid, 6-octenoic acid, 6-nonenoic acid, 6-decenoic acid and its esters, 6-dodecene-1,12-dioic acid and its esters, 7-octenoic acid, 7-nonenoic acid, 7-decenoic acid, 7-undecenoic acid, and 7-dodecenoic acid and its esters.

Additional examples of second functionalized alkene compounds include allyl alcohol, 2-butenol, 3-buten-1-ol, 2-penten-1-ol, 3-penten-1-ol, 4-penten-1-ol, 2-hexen-1-ol, 3-hexen-1-ol, 4-hexen-1-ol, 5-hexen-1-ol, and the like; buten-1,4-diol, 2-penten-1,5-diol, 2-hexen-1,6-diol, 3-hexen-1,6-diol, and the like; allyl amine, 1-amino-2-butene, 1-amino-3-butene, 1-amino-2-pentene, 1-amino-3-pentene, 1-amino-4-pentene, 1-amino-2-hexene, 1-amino-3-hexene, 1-amino-4 hexene, 1-amino-5-hexene, and the like; 1,4-diamino-2-butene, 1,5-diamino-2-pentene, 1,6-diamino-2-hexene, 1,6-diamino-3-hexene, and the like; 1-chloro-2-propene (i.e., allyl chloride), 1-chloro-2-butene, 1-chloro-3-butene, 1-chloro-2-pentene, 1-chloro-3-pentene, 1-chloro-4-pentene, 1-chloro-2-hexene, 1-chloro-3-hexene, 1-chloro-4-hexene, 1-chloro-5-hexene, and the like (including the F, Br, or I analogs); 1,4-dichloro-2-butene (Cl—$CH_2$—CH=CH—$CH_2$—Cl), 1,5-dichloro-2-pentene, 1,6-dichloro-2-hexene, 1,6-dichloro-3-hexene, and the like (including the F, Br, or I analogs); acrolein (propenal), 2-butenal, 3-butenal, 2-pentenal, 3-pentenal, 4-pentenal, 2-hexenal, 3-hexenal, 4-hexenal, 5-hexenal, and the like; 2-buten-1,4-dial, 2-penten-1,5-dial, 2-hexen-1,6-dial, 3-hexen-1,6-dial, and the like; acrylonitrile (cyanoethylene), 1-cyano-1-propene, 1-cyano-2-propene, 1-cyano-1-butene, 1-cyano-2-butene, 1-cyano-3-butene, 1-cyano-1-pentene, 1-cyano-2-pentene, 1-cyano-3-pentene, and the like; 1,2-dicyanoethylene, 1,3-dicyanopropene, 1,4-dicyano-1-butene, 1,4-dicyano-2-butene, and the like.

In exemplary embodiments, the second functionalized alkene is symmetric about its carbon-carbon double bond. That is, the group —$R^{12}$ is the same as group —$(CH_2)_n$—$R^{13}$. Advantageously, when the second functionalized alkene is symmetric, the number of products formed in the cross-metathesis reaction is reduced as compared to cross-metathesis reactions where the second functionalized alkene is asymmetric. This may provide for higher yields and/or easier separation of the desired bifunctional compound. Representative examples of symmetric functionalized alkenes include maleic acid ($HO_2CCH$=$CHCO_2H$) and esters thereof, 3-hexenedioc acid ($HO_2CCH_2CH$=$CHCH_2CO_2H$) and esters thereof (e.g., the dimethyl ester of 3-hexenedioc acid ($CH_3O_2CCH_2CH$=$CHCH_2CO_2CH_3$)), 4-octene-1,8-dioic acid and esters thereof, 5-decene-1,10-dioic acid and esters thereof, and 6-dodecene-1,12-dioic acid esters.

In an exemplary embodiment, a Δ9 acid-functionalized starting composition is used and is cross-metathesized with 2-butene, providing an acid-functionalized alkene having the structure $HO_2C$—$(CH_2)_7$—CH=CH—$CH_3$. After separation, the acid-functionalized alkene is cross-metathesized with 3-hexenedioc acid ($HO_2CCH_2CH$=$CHCH_2CO_2H$) in the presence of a metathesis catalyst. The cross-metathesis yields an unsaturated C12 diacid according to the formula below:

$$HO_2C-(CH_2)-CH=CH-CH_3+$$
$$HO_2CCH_2CH=CHCH_2CO_2H \rightarrow HO_2C-$$
$$(CH_2)_7-CH=CH-CH_2-CO_2H+CH_3-$$
$$CH=CHCH_2CO_2H$$

Optionally, the unsaturated C12 diacid may be hydrogenated to produce the corresponding saturated C12 diacid.

In another exemplary embodiment, a Δ9 acid-functionalized starting composition is used and is cross-metathesized with 2-butene, providing an acid-functionalized alkene having the structure $HO_2C$—$(CH_2)_7$—CH=CH—$CH_3$. After separation, the acid-functionalized alkene is cross-metathesized with maleic acid ($HO_2C$—CH=CH—$CO_2H$) in the presence of a metathesis catalyst. The cross-metathesis yields an unsaturated C11 diacid according to the formula below:

$$HO_2C-(CH_2)-CH=CH-CH_3+HO_2C-$$
$$CH=CH-CO_2H \rightarrow HO_2C-(CH_2)-$$
$$CH=CH-CO_2H+CH_3-CH=CH-CO_2H$$

Other examples of bifunctional organic products that may be made using the method of the invention are summarized in TABLES C-D.

TABLE C

| Starting Composition | Second Functionalized Alkene | Bifunctional Organic Compound |
| --- | --- | --- |
| Δ9 acid | But-2-ene-1,4-dial | 11-oxoundec-9-enoic acid OHCCH=CH(CH$_2$)$_7$CO$_2$H |
| Δ9 acid | But-2-ene-1,4-diamide | 10-carboxamidodec-9-enoic acid H$_2$NCOCH=CH(CH$_2$)$_7$CO$_2$H |
| Δ9 acid | But-2-ene-1,4-diol | 11-hydroxyundec-9-enoic acid HOCH$_2$CH=CH(CH$_2$)$_7$CO$_2$H |
| Δ9 acid | But-2-ene-1,4-diamine | 11-aminoundec-9-enoic acid H$_2$NCH$_2$CH=CH(CH$_2$)$_7$CO$_2$H |

TABLE C-continued

| Starting Composition | Second Functionalized Alkene | Bifunctional Organic Compound |
|---|---|---|
| Δ9 acid | But-2-ene-1,4-dichloride | 11-chloroundec-9-enoic acid $ClCH_2CH=CH(CH_2)_7CO_2H$ |
| Δ9 acid | Hex-3-ene-1,6-dial | 12-oxodec-9-enoic acid $OHCCH_2CH=CH(CH_2)_7CO_2H$ |
| Δ9 acid | Hex-3-ene-1,6-diamide | 11-carboxamidoundec-9-enoic acid $H_2NCOCH_2CH=CH(CH_2)_7CO_2H$ |
| Δ9 acid | Hex-3-ene-1,6-diol | 12-hydroxydodec-9-enoic acid $HO(CH_2)_2CH=CH(CH_2)_7CO_2H$ |
| Δ9 acid | Hex-3-ene-1,6-diamine | 12-aminododec-9-enoic acid $H_2N(CH_2)_2CH=CH(CH_2)_7CO_2H$ |
| Δ9 acid | Hex-3-ene-1,6-dichloride (or other halogens) | 12-chlorododec-9-enoic acid (or other halogens) $Cl(CH_2)_2CH=CH(CH_2)_7CO_2H$ |

TABLE D

| Starting Composition | Second Functionalized Alkene | Bifunctional Organic Compound |
|---|---|---|
| Δ9 methyl ester | But-2-ene-1,4-dial | Methyl 11-oxoundec-9-enoate $OHCCH=CH(CH_2)_7CO_2CH_3$ |
| Δ9 methyl ester | But-2-ene-1,4-diamide | Methyl 10-carboxamidodec-9-enoate $H_2NCOCH=CH(CH_2)_7CO_2CH_3$ |
| Δ9 methyl ester | But-2-ene-1,4-diol | Methyl 11-hydroxyundec-9-enoate $HOCH_2CH=CH(CH_2)_7CO_2CH_3$ |
| Δ9 methyl ester | But-2-ene-1,4-diamine | Methyl 11-aminoundec-9-enoate $H_2NCH_2CH=CH(CH_2)_7CO_2CH_3$ |
| Δ9 methyl ester | But-2-ene-1,4-dichloride | Methyl 11-chloroundec-9-enoate $ClCH_2CH=CH(CH_2)_7CO_2CH_3$ |
| Δ9 methyl ester | Hex-3-ene-1,6-dial | Methyl 12-oxododec-9-enoate $OHCCH_2CH=CH(CH_2)_7CO_2CH_3$ |
| Δ9 methyl ester | Hex-3-ene-1,6-diamide | Methyl 11-carboxamidoundec-9-enoate $H_2NCH_2COCH=CH(CH_2)_7CO_2CH_3$ |
| Δ9 methyl ester | Hex-3-ene-1,6-diol | Methyl 12-hydroxydodec-9-enoate $HO(CH_2)_2CH=CH(CH_2)_7CO_2CH_3$ |
| Δ9 methyl ester | Hex-3-ene-1,6-diamine | Methyl 12-aminododec-9-enoate $H_2N(CH_2)_2CH=CH(CH_2)_7CO_2CH_3$ |
| Δ9 methyl ester | Hex-3-ene-1,6-dichloride (or other halogens) | Methyl 12-chlorododec-9-enoate (or other halogens) $Cl(CH_2)_2CH=CH(CH_2)_7CO_2CH_3$ |

Optionally, the above-listed unsaturated compounds may be hydrogenated to form the corresponding saturated compounds.

Hydrogenation Catalysts

After self- or cross-metathesis (i.e., step (d)), the resulting alkene may be hydrogenated to remove the carbon-carbon double bond. Hydrogenation is typically conducted by exposing the alkene to $H_2$ gas in the presence of a hydrogenation catalyst.

The principal component of the catalyst useful for the hydrogenation is selected from metals from the group consisting of palladium, ruthenium, rhenium, rhodium, iridium, platinum, nickel, cobalt, copper, iron, osmium; compounds thereof; and combinations thereof.

The catalyst may be supported or unsupported. A supported catalyst is one in which the active catalyst agent is deposited on a support material by a number of methods, such as spraying, soaking or physical mixing, followed by drying, calcination, and if necessary, activation through methods such as reduction or oxidation. Materials frequently used as a support are porous solids with high total surface areas (external and internal), which can provide high concentrations of active sites per unit weight of catalyst. The catalyst support may enhance the function of the catalyst agent. A supported metal catalyst is a supported catalyst in which the catalyst agent is a metal.

A catalyst that is not supported on a catalyst support material is an unsupported catalyst. An unsupported catalyst may be platinum black or a Raney™ (W.R. Grace & Co., Columbia, Md.) catalyst. Raney™ catalysts have a high surface area due to selectively leaching an alloy containing the active metal(s) and a leachable metal (usually aluminum). Raney® catalysts have high activity due to the higher specific area and allow the use of lower temperatures in hydrogenation reactions. The active metals of Raney™ catalysts include nickel, copper, cobalt, iron, rhodium, ruthenium, rhenium, osmium, iridium, platinum, palladium; compounds thereof; and combinations thereof.

The catalyst support useful herein can be any solid, inert substance including, but not limited to, oxides such as silica, alumina and titania; barium sulfate; calcium carbonate; and carbons. The catalyst support can be in the form of powder, granules, pellets, or the like.

A preferred support material of the invention is selected from the group consisting of carbon, alumina, silica, silica-alumina, silica-titania, titania, titania-alumina, barium sulfate, calcium carbonate, strontium carbonate, compounds thereof and combinations thereof. Supported metal catalysts can also have supporting materials made from one or more compounds. More preferred supports are carbon, titania and alumina. Further preferred supports are carbons with a surface area greater than 100 $m^2/g$. A further preferred support is carbon with a surface area greater than 200 $m^2/g$. Preferably, the carbon has an ash content that is less than 5% by weight of the catalyst support; the ash content is the inorganic residue (expressed as a percentage of the original weight of the carbon) which remains after incineration of the carbon.

The preferred content of the metal catalyst in the supported catalyst is from about 0.1% to about 20% of the supported catalyst based on metal catalyst weight plus the support weight. A more preferred metal catalyst content range is from about 1% to about 10% of the supported catalyst.

Combinations of metal catalyst and support system may include any one of the metals referred to herein with any of the supports referred to herein. Preferred combinations of metal catalyst and support include palladium on carbon, palladium on calcium carbonate, palladium on barium sulfate, palladium on alumina, palladium on titania, platinum on carbon, platinum on alumina, platinum on silica, iridium on silica, iridium on carbon, iridium on alumina, rhodium on carbon, rhodium on silica, rhodium on alumina, nickel on carbon, nickel on alumina, nickel on silica, rhenium on carbon, rhenium on silica, rhenium on alumina, ruthenium on carbon, ruthenium on alumina and ruthenium on silica.

Further preferred combinations of metal catalyst and support include palladium on carbon, palladium on alumina, palladium on titania, platinum on carbon, platinum on alumina, rhodium on carbon, rhodium on alumina, ruthenium on carbon and ruthenium on alumina.

The method of the invention will now be described with reference to FIG. 1 to FIG. 3. Referring now to FIG. 1, a process flow diagram of an embodiment of the method 10 of the invention is shown. In the method 10, starting material composition 12 is provided that comprises a Δ9 unsaturated fatty acid, a Δ9 unsaturated fatty ester, a salt thereof, or a mixture thereof. In reaction 14, starting material composition 12 is cross-metathesized with a short-chain internal olefin 16 in the presence of a first metathesis catalyst 17 to produce cross-metathesis products 18 comprising (i) one or more olefins 20, and (ii) one or more acid-, ester-, or salt-functionalized alkenes 22. Following this, at least a portion of the acid-, ester-, or salt-functionalized alkene 22 is separated 23 from the remaining cross-metathesis products 18. Spent metathesis catalyst 17 may also be removed. In the next step, the isolated acid-, ester-, or salt-functionalized alkene 22 is then self-metathesized 24 in the presence of a second metathesis catalyst 28 to produce a C18 diacid, diester, or disalt alkene 30 and one or more olefin products 32. Optionally, the C18 diacid, diester, or disalt alkene can be hydrogenated to form a saturated C18 diacid, diester, or disalt compound.

If the starting material comprises a fatty ester in glyceride form, the glyceride may be converted (e.g., by transesterification) into free fatty esters prior to being cross-metathesized with the short-chain internal olefin, or the glyceride can be cross-metathesized with the short-chain internal olefin followed by conversion (e.g., by transesterification) into free fatty esters.

Figure 2:
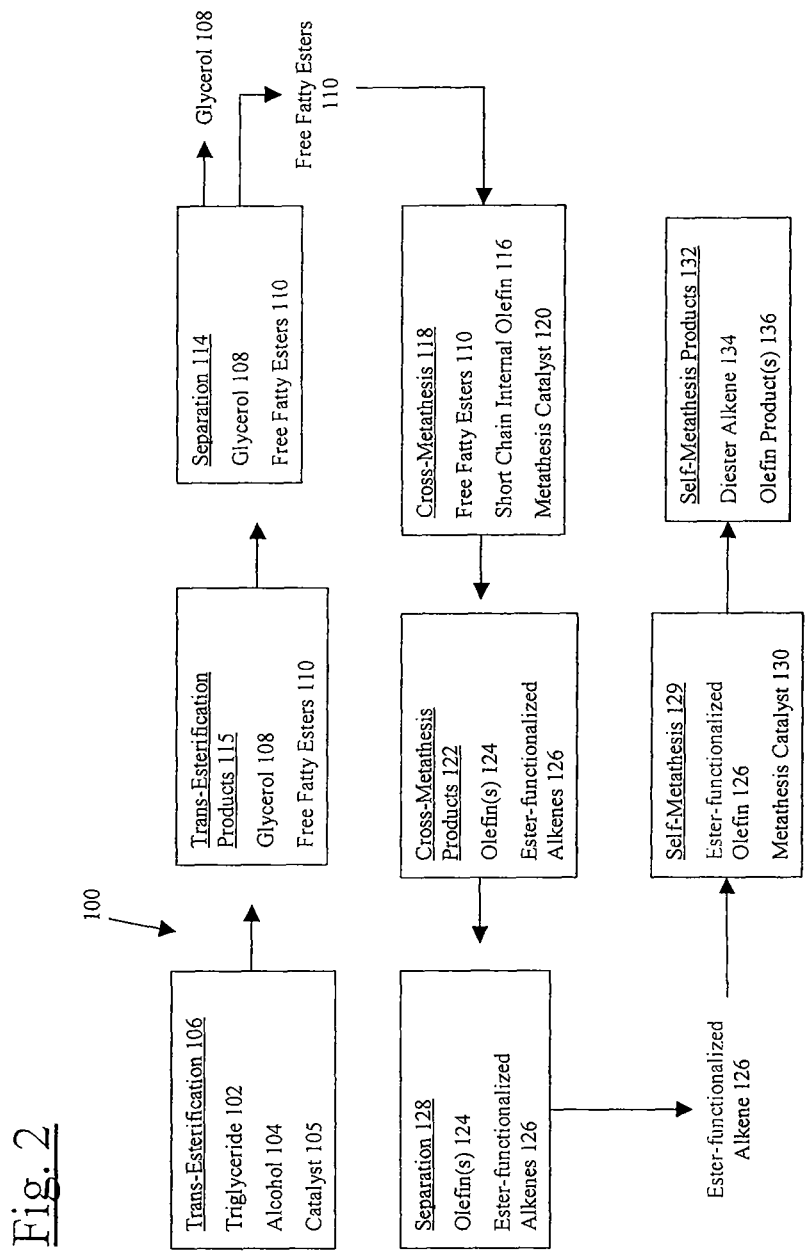
FIG. 2 is a process flow diagram of an embodiment of the method of the invention.

Referring now to FIG. 2, a process flow diagram of an embodiment of the method 100 of the invention is shown. In this embodiment, a fatty acid triglyceride starting material is converted into free fatty esters prior to cross-metathesizing the free fatty esters with a short-chain internal olefin. In a first step of the method, triglyceride 102 and alcohol 104 are trans-esterified 106 in the presence of trans-esterification catalyst 105. Trans-esterification reaction 106 converts triglyceride 102 into glycerol 108 and free fatty esters 110. Together, the glycerol 108 and free fatty acid esters 110 are referred to as trans-esterification products 115. After trans-esterification reaction 106, a separation 114 (e.g., water wash or distillation) is conducted on the trans-esterification products 115 in order to separate the glycerol 108 from the free fatty acid esters 110. Spent metathesis catalyst 105 may also be removed.

After separation, a cross-metathesis reaction 118 is conducted between the free fatty esters 110 and short-chain internal olefin 116. The cross-metathesis 118 is conducted in the presence of a metathesis catalyst 120 in order to form cross-metathesis products 122 comprising one or more olefins 124 and one or more ester-functionalized alkenes 126. Following this, at least a portion of the ester-functionalized alkenes 126 are separated 128 (e.g., using distillation) from the cross-metathesis products 122. The isolated ester-functionalized alkene 126 is then self-metathesized 129 in the presence of a second metathesis catalyst 130 to produce the self-metathesis products 132 comprising a diester alkene 134 and one or more olefin products 136.

Figure 3:
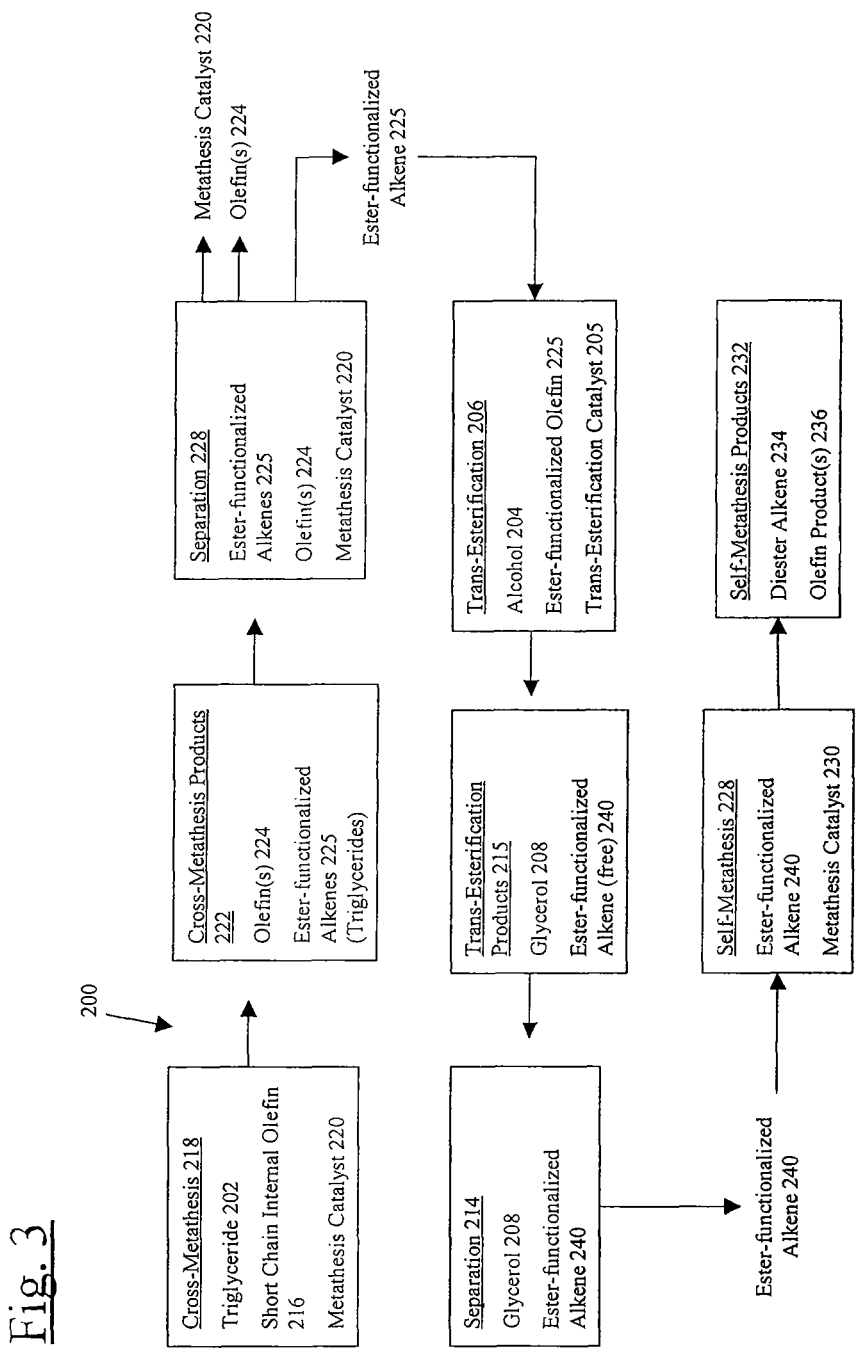
FIG. 3 is a process flow diagram of an embodiment of the method of the invention.

Referring to FIG. 3, a process flow diagram of another embodiment of the method 200 of the invention is shown. In this embodiment, a fatty acid triglyceride starting material is cross-metathesized with a short-chain internal olefin. In the first reaction of method 200, triglyceride 202 and short-chain internal olefin 216 are cross-metathesized 218 in the presence of a metathesis catalyst 220 to form cross-metathesis products 222. Cross-metathesis products 222 comprise one or more olefins 224 and one or more ester-functionalized alkenes 225. In this embodiment, the ester-functionalized alkenes 225 are triglycerides. The cross-metathesis products 222 are then separated 228 into one or more ester-functionalized alkenes (triglyceride) products 225 and one or more olefins 224. Spent metathesis catalyst 220 can also be removed. Following this, the ester-functionalized alkene (triglyceride) products 225 are trans-esterified 206 with an alcohol 204 in the presence of a trans-esterification catalyst 205. Trans-esterification reaction 206 converts the ester-functionalized alkene (triglyceride) products 225 into trans-esterification products 215 comprising glycerol 208 and free ester-functionalized alkene 240. After trans-esterification reaction 206, a separation 214 is conducted in order to separate the glycerol 208 from the free ester-functionalized alkene 240. The free ester-functionalized alkene 240 is then self-metathesized 228 in the presence of a metathesis catalyst 230 in order to form a diester alkene product 234 and one or more olefin products 236. In an alternative embodiment (not shown in FIG. 3), the ester-functionalized alkene (triglyceride) is self-metathesized and the resulting product is trans-esterified to produce glycerol and free ester-functionalized alkene.

Figure 2A:
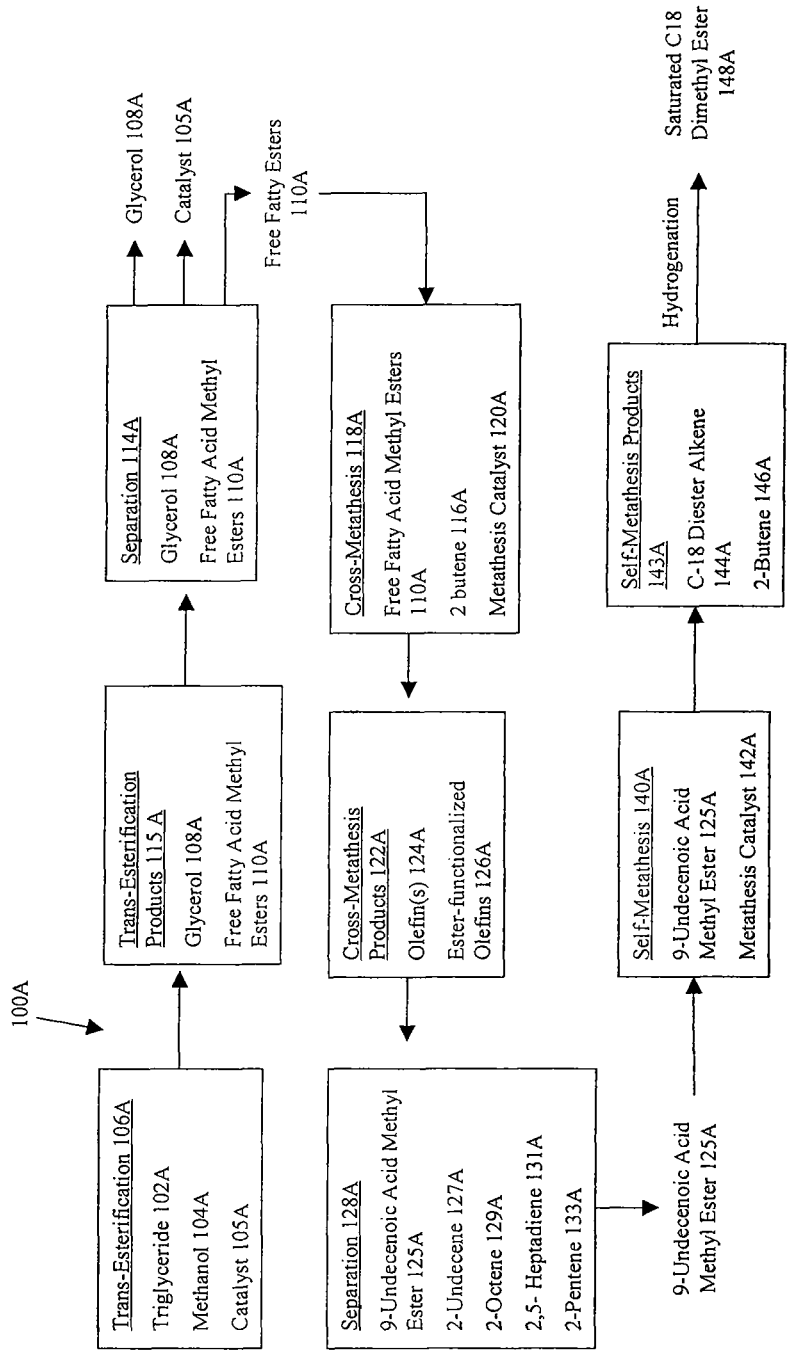
FIG. 2A is a process flow diagram of an embodiment of the method of the invention.

In an exemplary embodiment, as shown in FIG. 2A, triglyceride 102A is reacted with methanol 104A in trans-esterification reaction 106A in the presence of trans-esterification catalyst 105A. Trans-esterification reaction 106A converts triglyceride 102A into glycerol 108A and free fatty acid methyl esters 110A. Collectively, glycerol 108A and free fatty acid methyl esters 110A are referred to as trans-esterification products 115A. In this embodiment, the free fatty acid methyl esters 110A comprise methyl oleate (i.e., the methyl ester of oleic acid), methyl linoleate (i.e., the methyl ester of linoleic acid), and methyl linolenate (i.e., the methyl ester of linolenic acid). After trans-esterification reaction 106A, separation process 114A is conducted on the trans-esterification products 115A in order to separate the glycerol 108A from the free fatty acid methyl esters 110A. Spent metathesis catalyst 105A can also be removed. Following separation, the free fatty acid methyl esters 110A and 2-butene 116A (i.e., a short-chain internal olefin) are cross-metathesized 118A in the presence of a metathesis catalyst 120A to form cross-metathesis products 122A comprising olefins 124A and ester-functionalized alkenes 126A. The cross-metathesis products 122A are then separated by separation process 128A into product streams comprising 9-undecenoic acid methyl ester 125A, 2-undecene 127A, 2-octene 129A, 2, 5-heptadiene 131A, and 2-pentene 133A. Next, 9-undecenoic acid methyl ester 125A is self-metathesized 140A in the presence of a metathesis catalyst 142A to form self-metathesis products 143A comprising a C18 diester alkene 144A and 2-butene 146A. Optionally, the C18 diester alkene 144A can be hydrogenated to form a saturated C18 diester 148A.

Figure 2B:
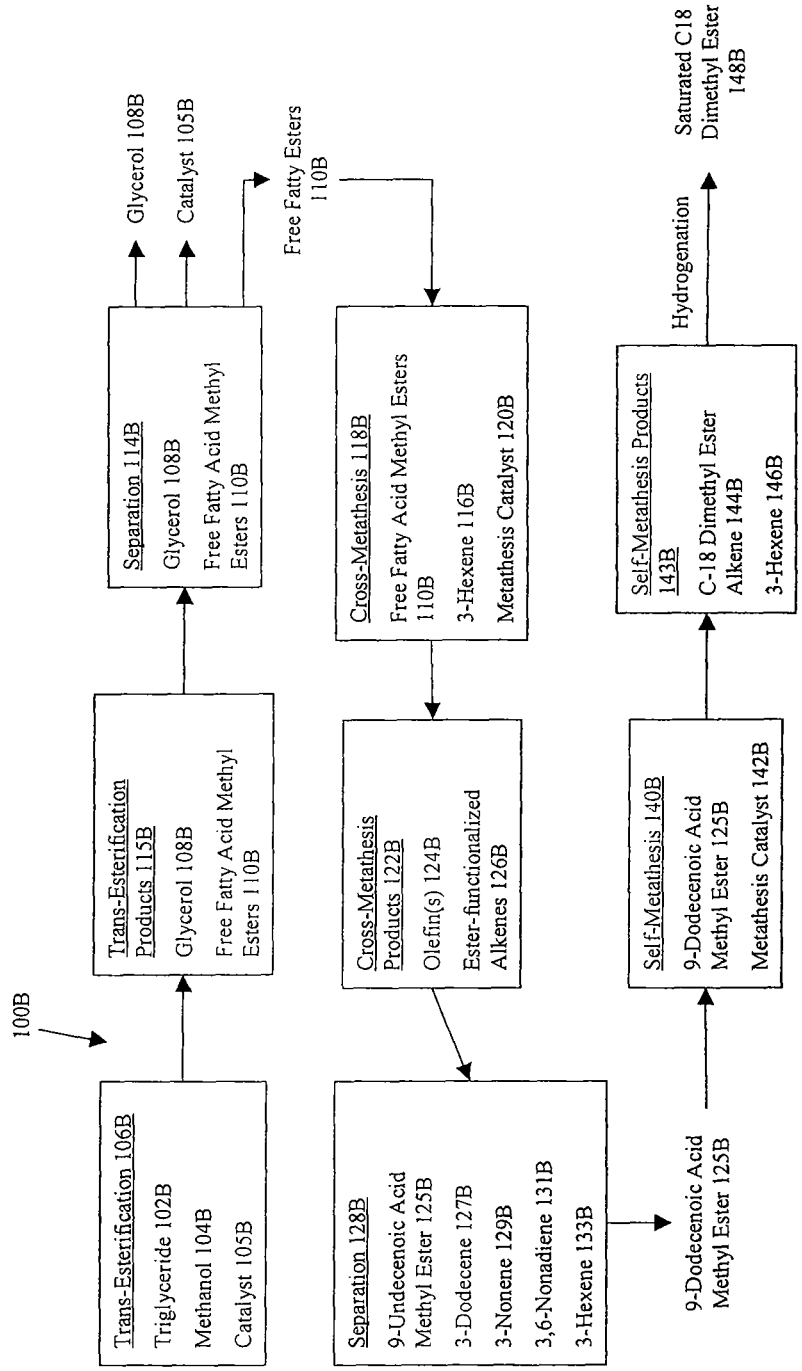
FIG. 2B is a process flow diagram of an embodiment of the method of the invention.

In another exemplary embodiment, as shown in FIG. 2B, triglyceride 102B is reacted with methanol 104B in trans-esterification reaction 106B in the presence of trans-esterification catalyst 105B. Trans-esterification reaction 106B converts triglyceride 102B into trans-esterification products 115B including glycerol 108B and free fatty acid methyl ester 110B. After trans-esterification reaction 106B, separation process 114B is conducted on the trans-esterification products 115B in order to separate the glycerol 108B from the free fatty acid methyl ester 110B. Spent metathesis catalyst 105B can also be removed. Following separation, fatty acid methyl ester 110B and 3-hexene 116B (i.e., a short-chain internal olefin) are cross-metathesized 118B in the presence of a metathesis catalyst 120B to form cross-metathesis products 122B comprising olefins 124B and ester-functionalized alkenes 126B. Cross-metathesis products 122B are separated via separation process 128B into product streams comprising: 9-dodecenoic acid methyl ester 125B, 3-dodecene 127B, 3-nonene 129B, 3, 6-nonadiene 131B, and 3-hexene 133B. Next, 9-dodecenoic acid methyl ester 125B is self-metathesized 140B in the presence of a metathesis catalyst 142B to form self-metathesis products 143B comprising a C18 dimethyl ester alkene 144B and 3-hexene 146B. Optionally, the C18 diester alkene can be hydrogenated to form a saturated C18 dimethyl ester 148B.

The invention will now be described with reference to the following non-limiting examples.

EXAMPLES

Example 1: Synthesis of 1, 18-Diester (1,18-dimethyl ester of 9-octadecene) from 3-Hexene and Soybean Oil

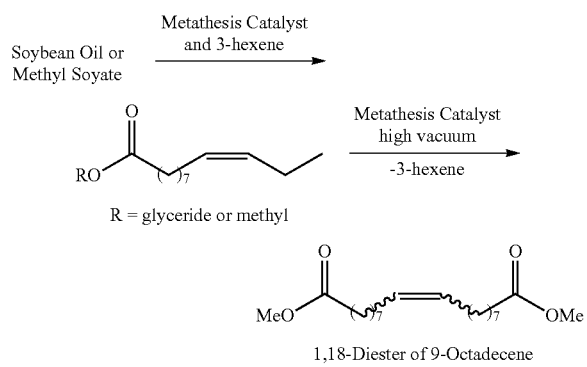

1,18-Diester of 9-Octadecene

Step 1: Production of Methyl 9-dodecenoate [CH$_3$CH$_2$CH=CH(CH$_2$)$_7$CO$_2$CH$_3$]

Metathesis reactions were conducted in a 250 ml 3-neck round bottom Schlenk flask that was equipped with a reflux condenser (connected to a bubbler), two septa, a stir bar, and a thermocouple. Prior to adding any reactants, the apparatus was degassed with argon for thirty minutes. Then, 70 ml (64.4 g) of degassed soybean oil (Cargill soybean oil (Salad oil), Lot # F4102) was added to the apparatus. In a separate container, 3-hexene was degassed with argon for one hour. Following degassing, 127 ml (86.4 grams) of the degassed 3-hexene was added to the flask using a graduated cylinder. The resulting mixture was degassed for fifteen minutes with argon. The mixture was then heated to 65° C. before adding the metathesis catalyst.

Metathesis catalyst (C827, Lot #067-050B) was added to the degassed mixture of soybean oil and 3-hexene in the amount shown in TABLE 1. In each case, the resulting mixture was allowed to react at 65° C., with aliquots taken at 2, 4, and 6 hours to check for conversion using a gas chromatograph. Maximum conversion was reached after two hours in all cases. In each case, after reacting for 6 hours, 1.30 grams of activated clay (Pure-Flo B80 natural Bleaching Adsorbent) was added, and the resulting composition was stirred overnight. Following this, the composition was filtered through a bed of silica to remove the activated clay and metathesis catalyst. The filtrates were sealed in a sample bottle and refrigerated. Percent yield of methyl 9-dodecenoate was determined using a gas chromatograph. The resulting data is presented in TABLE 1.

TABLE 1

| Example No. | Catalyst Loading[1] (ppm) | % Yield of Methyl 9-dodecenoate[2] |
|---|---|---|
| 1-1 | 100 | 33.7 |
| 1-2 | 75 | 40.1 |
| 1-3 | 50 | 30.5 |
| 1-4 | 100 | 33.0 |

[1]Catalyst 827 loading in ppm per double bond of SBO. 3-Hexene was added in 3 equivalents per double bond of SBO.
[2]GC yield after 2 hours, yields did not change significantly at 6 hours.

Step 2: Self-Metathesis of Methyl 9-Dodecenoate

Samples of methyl 9-dodecenoate were warmed to temperature (see, TABLE 2) and were degassed with argon for 30 minutes. Next, a metathesis catalyst (see, TABLE 2) was added to the methyl 9-dodecenoate and vacuum was applied to provide a pressure of <1 mmHg. The methyl 9-dodecenoate was then allowed to self-metathesize for the time reported in TABLE 2. GC analysis indicated that 1,18-dimethyl ester of 9-octadecene [CH$_3$O$_2$C(CH$_2$)$_7$CH=CH(CH$_2$)$_7$CO$_2$CH$_3$] was produced in the yield reported in TABLE 2.

TABLE 2

| Example No. | 9C$_{12}$O$_2$Me | Catalyst No. | Catalyst Loading (ppm) | Reaction Time (hours) | Reaction Temp. (° C.) | 9-C18(O$_2$Me)$_2$ (GC Area %) |
|---|---|---|---|---|---|---|
| 1-5 | 10.6 | C-827 | 100 | 3 | 50 | 83.5 |
| 1-6 | 10.6 | C-827 | 150 | 3 | 50 | 87.0 |
| 1-7 | 10.6 | C-848 | 75 | 20 | 25 | 86.0 |
| 1-8 | 10.6 | C-848 | 150 | 20 | 25 | 81.1 |
| 1-9 | 10.6 | C-827 | 50 | 3 | 50 | 82.5 |
| 1-10 | 10.6 | C-848 | 25 | 5 | 40 | 83.7 |
| 1-11 | 10.6 | C-827 | 25 | 3 | 50 | 83.0 |
| 1-12 | 10.6 | C-827 | 10 | 3 | 50 | 66.2 |
| 1-13 | 10.6 | C-827 | 17 | 4 | 50 | 81.8 |
| 1-14 | 10.6 | C-827 | 15 | 4 | 50 | 90.0 |
| 1-15 | 10.6 | C-827 | 13 | 4 | 50 | 89.9 |
| 1-16 | 10.6 | C-827 | 10 | 4 | 50 | 81.1 |
| 1-17 | 10.6 | C-827 | 5 | 4 | 50 | 50.9 |
| 1-18 | 10.6 | C-627 | 25 | 4 | 55 | 84.0 |
| 1-19 | 10.6 | C-627 | 10 | 4 | 55 | 87.5 |

Example 2: Vacuum Distillation of 9C$_{12}$O$_2$Me

A glass 2.0 L 3-necked round bottom flask with a magnetic stirrer, packed column, distillation head, and temperature controller was charged with esterified products and was placed in a heating mantle. The flask was attached to a 2-inch×36-inch glass distillation packed column containing 0.16" Pro-Pak™ stainless steel saddles. The distillation column was connected to a fractional distillation head, which was connected to a vacuum line. A 500 mL pre-weighed round bottom flask was used to collect the distilled fractions. During distillation, vacuum was applied to provide a pressure of <1 mmHg. TABLE 3 contains the vacuum distillation results.

TABLE 3

Distillation Data

| Distillation Fraction | Distillation Head Temperature (° C.) | Pot Temperature (° C.) | Isolated Weight (grams) | GC Retention Time (min) |
|---|---|---|---|---|
| $3C_9 + 3,6\ C_9$ | 26 | 37 | 136.5 | 1.6 |
| $3C_{12} + 3,6\ C_{12}$ | 48 | 58 | 125.4 | 3.87 |
| $6C_{15} + 6,9\ C_{15}$ | 92-94 | 115-120 | 68 | 7.45 |
| $9C_{12}\text{—}O_2Me$ | 93-96 | 120-122 | 275.4 | 7.88 |

$6C_{15}+6,9C_{15}$ impurities were separated from $9C_{12}O_2Me$ by equilibrating the distillation column for 24 hours, followed by collecting $6C_{15}+6,9C_{15}$ with a reflux ratio of 1:10 (i.e. 1 drop collected for every 10 drops sent back to the packed column). This procedure demonstrates that $9C_{12}O_2Me$ (275.4 g.) could be isolated in 50.9% yield and in 99.2% chemical purity. The $6C_{15}+6,9C_{15}$ impurities could be removed by fractional distillation.

Example 3: Self-Metathesis of Methyl 9-Decenoate

Methyl 9-decenoate (25 g, 114 mmol, ~90% chemical purity) obtained by ethenolysis of methyl oleate was charged in a 250 mL round-bottomed flask and was degassed with argon for 30 min. C823 metathesis catalyst (127 mg, 0.15 mmol, 0.13 mol %) was then added, and the reaction contents were heated to 35° C. under vacuum for 16 hrs. A 1.0 M solution of tris(hydroxymethyl)phosphine (4 mL) was then added and the reaction contents were heated to 90° C. for 4 hr. The reaction contents were then cooled to room temperature and were diluted with 50 mL of ethyl acetate. The diluted reaction contents were then washed sequentially with (1) 50 mL of 1.0 M aqueous HCl, (2) water, and (3) brine. The resulting organic phase was then dried with anhydrous sodium sulfate, filtered, and concentrated by rotary evaporation. 1 gram of the crude diester (1,18-dimethyl 9-octadecenedioate) was then dissolved in 4.5 mL of hexanes and the resulting homogeneous solution was cooled to −11° C. for 5 hrs. The crystals that formed were filtered and air-dried. GC analysis of the crystals indicated 95.8% chemical purity and 99:1 E:Z isomeric ratio.

Example 4: Preparation of 1,12-Diester of Dodecene from Methyl-9-Dodecenoate and Methyl-3-Pentenoate Step 1: Methyl-9-dodecenoate was Prepared as Described in Step 1 of EXAMPLE 1

Step 2: Cross-metathesis of Methyl 9-dodecenoate with Methyl-3-Pentenoate

Methyl 9-dodecenoate and methyl-3-pentenoate were combined and degassed with argon for 30 minutes, then warmed to temperature (see, TABLE 4). Next, a metathesis catalyst (see, TABLE 4) was added to the methyl 9-dodecenoate and methyl-3-pentenoate mixture. The mixture was then allowed to metathesize for the time reported in TABLE 4. GC analysis indicated that 1,12-dimethyl ester of dodecene [$CH_3O_2C(CH_2)_7CH\!=\!CH(CH_2)CO_2CH_3$] was produced in the GC yield reported in TABLE 4.

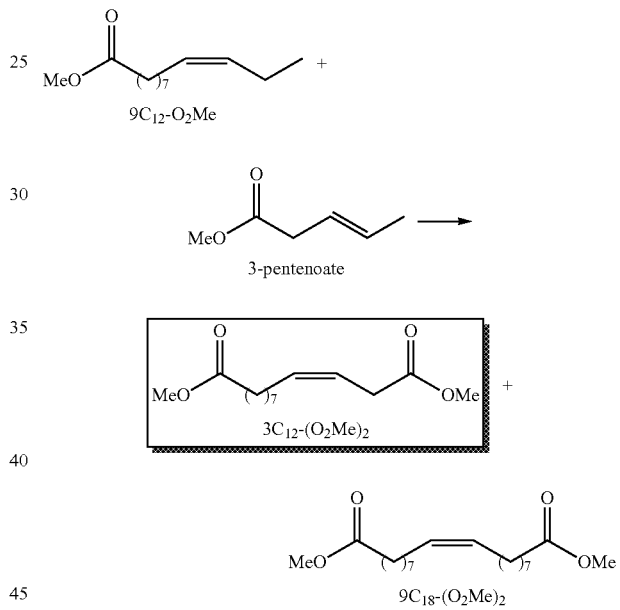

TABLE 4

| Example No. | Equiv of methyl-3-pentenoate | catalyst | catalyst loading (ppm) | Temp (° C.) | GC Area % Product | | | |
|---|---|---|---|---|---|---|---|---|
| | | | | | 30 min | 60 min | 120 min | 240 min |
| 4-1 | 1 | 827 | 1000 | 60 | ND | ND | ND | 27.1 |
| 4-2 | 3 | 827 | 1000 | 60 | ND | ND | ND | 36.4 |
| 4-3 | 5 | 827 | 1000 | 60 | ND | ND | ND | 32.9 |
| 4-4 | 3 | 827 | 100 | 60 | ND | ND | ND | 2.5 |
| 4-5 | 3 | 827 | 250 | 60 | ND | ND | ND | 12.0 |
| 4-6 | 3 | 827 | 500 | 60 | ND | ND | ND | 28.9 |
| 4-7 | 3 | 827 | 250 | 50 | ND | ND | ND | 15.0 |
| 4-8 | 3 | 827 | 250 | 70 | ND | ND | ND | 9.8 |
| 4-9 | 3 | 827 | 100 | 60 | 0.0 | 0.0 | 0.0 | 0.0 |
| 4-10 | 3 | 827 | 50 | 60 | 0.0 | 0.0 | 0.0 | 0.0 |
| 4-11 | 3 | 827 | 25 | 60 | 0.0 | 0.0 | 0.0 | 0.0 |

* ND = no data
[1] No conversion was seen at lower catalyst loadings.

Example 5: Preparation of Methyl 11-Chloro-9-undecenoate from Methyl-9-Dodecenoate and 1,4-Dichloro-2-butene Step 1: Methyl-9-dodecenoate was Prepared as Described in Step 1 of EXAMPLE 1

Step 2: Cross-metathesis of methyl-9-dodecenoate with 1,4-dichloro-2-butene

Methyl 9-dodecenoate and 1,4-dichloro-2-butene were combined and degassed with argon for 30 minutes, then warmed to temperature (see, TABLE 5). Next, a metathesis catalyst (see, TABLE 5) was added to the methyl 9-dodecenoate and 1,4-dichloro-2-butene mixture. The mixture was then allowed to metathesize for the time reported in TABLE 5. GC analysis indicated that the product [$CH_3O_2C(CH_2)_7CH=CHCH_2Cl$] was produced in the GC yield reported in TABLE 5.

Example 6: Preparation of Methyl 12-Acetoxy-9-dodecenoate from Methyl-9-dodecenoate and 3-Buten-1-yl Acetate Step 1: Methyl 9-dodecenoate was Prepared as Described in Step 1 of EXAMPLE 1

Step 2: Cross-Metathesis of methyl 9-dodecenoate with 3-buten-1-yl Acetate

Methyl 9-dodecenoate and 3-buten-1-yl acetate were combined and degassed with argon for 30 minutes, then warmed to temperature (see, TABLE 6). Next, a metathesis catalyst (see, TABLE 6) was added to the methyl 9-dodecenoate and 3-buten-1-yl acetate mixture. The mixture was then allowed to metathesize for the time reported in TABLE 6. GC analysis indicated that the product [$CH_3O_2C(CH_2)_7CH=CH(CH_2)_2CO_2CH_3$] was produced in the GC yield reported in TABLE 6.

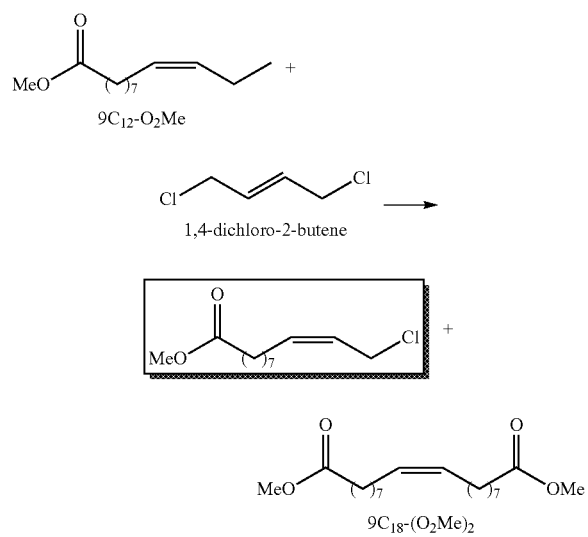

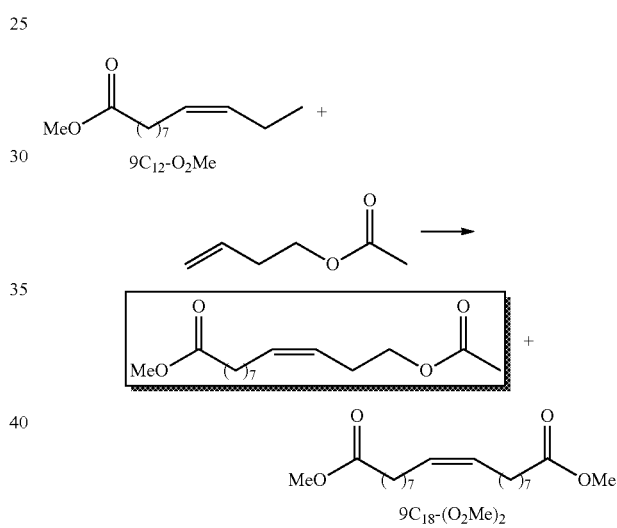

TABLE 5

| Example No. | Equiv of 1,4-dichloro-2-butene | catalyst | catalyst loading (ppm) | Temp (° C.) | GC Area % Product | | | |
|---|---|---|---|---|---|---|---|---|
| | | | | | 30 min | 60 min | 120 min | 240 min |
| 5-1 | 1 | 827 | 1000 | 60 | ND | ND | ND | 60.2 |
| 5-2 | 3 | 827 | 1000 | 60 | ND | ND | ND | 40.4 |
| 5-3 | 5 | 827 | 1000 | 60 | ND | ND | ND | 31.1 |
| 5-4[2] | 2 | 827 | 1000 | 25 (60) | 5.6 | 5.8 | 6.0 | 6.2 |
| 5-5[1] | 2 | 827 | 500 | 25 (60) | 34.6 | 34.5 | 35.0 | 35.1 |
| 5-6[1] | 2 | 827 | 250 | 25 (60) | 8.0 | 8.1 | 8.0 | 8.1 |
| 5-7[1] | 2 | 827 | 100 | 25 (60) | 1.6 | 1.5 | 1.6 | 1.6 |
| 5-8[1] | 2 | 827 | 50 | 25 (60) | 0.0 | 0.2 | 0.2 | 0.2 |

\* ND = no data
[1] 827 was initiated at 60° C., then reaction removed from heat to stir at room temp. Freshly distilled 1,4-dichloro-2-butene was used.
[2] 1,4-dichloro-2-butene used directly from bottle with no distillation.

TABLE 6

| Example No. | Equiv of 3-buten-1-yl acetate | catalyst | catalyst loading (ppm) | Temp (° C.) | GC Area % Product | | | |
|---|---|---|---|---|---|---|---|---|
| | | | | | 30 min | 60 min | 120 min | 240 min |
| 6-1[1] | 3 | 827 | 500 | 25 (60) | 34.5 | 34.2 | 34.1 | 34.4 |
| 6-2 | 3 | 827 | 500 | 60 | 25.9 | 33.4 | 33.4 | 33.3 |
| 6-3 | 3 | 827 | 250 | 60 | 16.2 | 16.1 | 16.0 | 15.8 |
| 6-4 | 3 | 827 | 100 | 60 | 4.6 | 4.6 | 4.6 | 4.7 |
| 6-5 | 3 | 827 | 50 | 60 | 0.9 | 1.1 | 1.2 | 1.2 |
| 6-6 | 3 | 827 | 25 | 60 | 1.0 | 1.1 | 1.1 | 1.1 |

[1]827 was initiated at 60° C., then reaction removed from heat to stir at room temp.

Example 7: Preparation of Methyl 12-Trimethylsiloxy-9-dodecenoate from Methyl 9-dodecenoate and 3-Buten-1-yl trimethylsilyl Ether Step 1: Methyl 9-dodecenoate was Prepared as Described in Step 1 of EXAMPLE 1

Step 2: Cross-Metathesis of Methyl 9-dodecenoate with 3-buten-1-yl Trimethylsilyl Ether Methyl 9-dodecenoate and 3-buten-1-yl trimethylsilyl ether were combined and degassed with argon for 30 minutes, then warmed to temperature (see, TABLE 7). Next, a metathesis catalyst (see, TABLE 7) was added to the methyl 9-dodecenoate and 3-buten-1-yl trimethylsilyl ether mixture. The mixture was then allowed to metathesize for the time reported in TABLE 7. GC analysis indicated that the product [$CH_3O_2C(CH_2)_7CH=CH(CH_2)_2OSi(CH_3)_3$] was produced in the GC yield reported in TABLE 7.

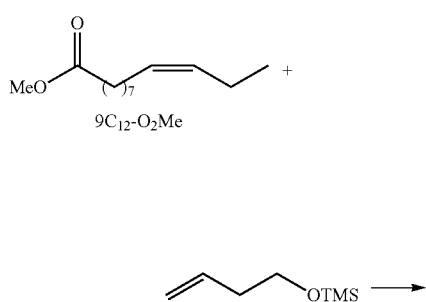

9C$_{12}$-O$_2$Me

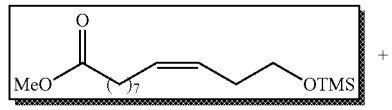

-continued

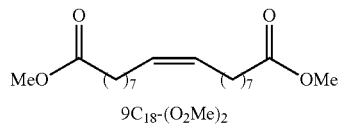

9C$_{18}$-(O$_2$Me)$_2$

TABLE 7

| Example No. | Equiv of 3-buten-1-yl trimethylsilyl ether | catalyst | catalyst loading (ppm) | Temp (° C.) | GC Area % Product | | | |
|---|---|---|---|---|---|---|---|---|
| | | | | | 30 min | 60 min | 120 min | 240 min |
| 7-1[1] | 3 | 827 | 500 | 25 (60) | 19.8 | 20.6 | 20.9 | 21.0 |
| 7-2 | 3 | 827 | 500 | 60 | 17.9 | 17.9 | 18.1 | 15.8 |
| 7-3 | 3 | 827 | 250 | 60 | 7.5 | 8.0 | 8.0 | 8.1 |
| 7-4 | 3 | 827 | 100 | 60 | 2.3 | 2.6 | 2.6 | 2.6 |
| 7-5 | 3 | 827 | 50 | 60 | 0.0 | 0.8 | 0.7 | 0.5 |
| 7-6 | 3 | 827 | 25 | 60 | 0.6 | 0.6 | 0.0 | 0.0 |

[1]827 was initiated at 60° C., then reaction removed from heat to stir at room temp.

Example 8: Preparation of Methyl 12-bromo-9-dodecenoate from Methyl-9-dodecenoate and 1-bromo-3-hexene Step 1: Methyl 9-dodecenoate was Prepared as Described in Step 1 of EXAMPLE 1

Step 2: Cross-Metathesis of Methyl 9-dodecenoate with 1-bromo-3-hexene

Methyl 9-dodecenoate and 1-bromo-3-hexene were combined and degassed with argon for 30 minutes, then warmed to temperature (see, TABLE 8). Next, a metathesis catalyst (see, TABLE 8) was added to the methyl 9-dodecenoate and 1-bromo-3-hexene mixture. The mixture was then allowed to metathesize for the time reported in TABLE 8. GC analysis indicated that the product [$CH_3O_2C(CH_2)_7CH=CH(CH_2)_2Br$] was produced in the GC yield reported in TABLE 8.

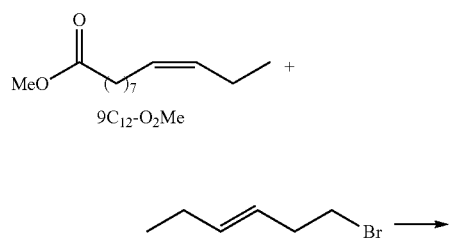

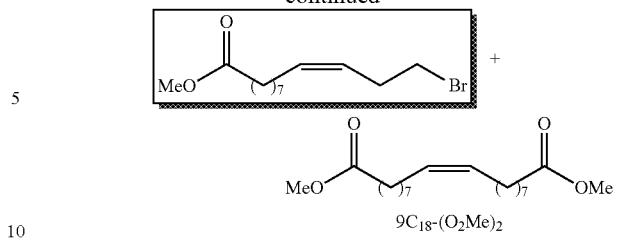

TABLE 8

| Example No. | Equiv of 1-bromo-3-hexene | catalyst | catalyst loading (ppm) | Temp (° C.) | GC Area % Product | | | |
|---|---|---|---|---|---|---|---|---|
| | | | | | 30 min | 60 min | 120 min | 240 min |
| 8-1 | 3 | 627 | 500 | 35 | 11.2 | 11.8 | 12.1 | 12.4 |
| 8-2 | 3 | 627 | 250 | 35 | 6.0 | 6.2 | 6.4 | 6.5 |
| 8-3 | 3 | 627 | 100 | 35 | 1.3 | 1.4 | 1.4 | 1.4 |

Example 9: Preparation of Methyl 11-chloro-9-undecenoate from Methyl-9-dodecenoate and Allyl Chloride Step 1: Methyl 9-dodecenoate was Prepared as Described in Step 1 of EXAMPLE 1

Step 2: Cross-Metathesis of methyl 9-dodecenoate with Allyl Chloride

Methyl 9-dodecenoate and allyl chloride were combined and degassed with argon for 30 minutes, then warmed to temperature (see, TABLE 9). Next, a metathesis catalyst (see, TABLE 9) was added to the methyl 9-dodecenoate and allyl chloride mixture. The mixture was then allowed to metathesize for the time reported in TABLE 9. GC analysis indicated that the product [CH$_3$O$_2$C(CH$_2$)$_7$CH=CHCH$_2$C] was produced in the GC yield reported in TABLE 9.

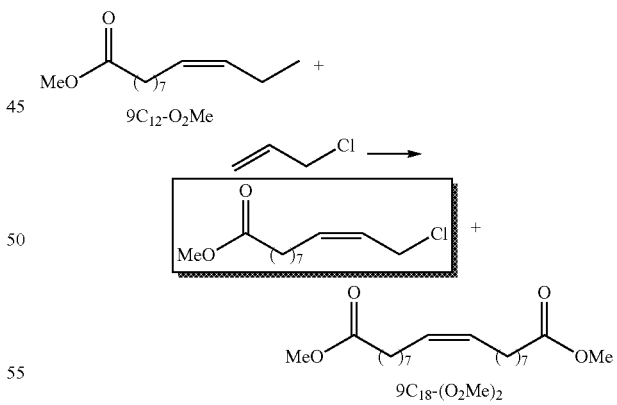

TABLE 9

| Example No. | Equiv of allyl chloride | catalyst | catalyst loading (ppm) | Temp (° C.) | GC Area % Product | | | |
|---|---|---|---|---|---|---|---|---|
| | | | | | 30 min | 60 min | 120 min | 240 min |
| 9-1 | 3 | 627 | 500 | 35 | 15.6 | 15.3 | 14.9 | 15.1 |
| 9-2 | 3 | 627 | 250 | 35 | 5.1 | 5.4 | 5.4 | 5.1 |
| 9-3 | 3 | 627 | 100 | 35 | 0.9 | 1.0 | 0.9 | 0.8 |

TABLE 9-continued

| Example No. | Equiv of allyl chloride | catalyst | catalyst loading (ppm) | Temp (° C.) | GC Area % Product | | | |
|---|---|---|---|---|---|---|---|---|
| | | | | | 30 min | 60 min | 120 min | 240 min |
| 9-4* | 3 | 627 | 500 | 35 | 12.3 | 12.7 | 12.7 | 13.1 |
| 9-5* | 3 | 627 | 250 | 35 | 9.9 | 10.4 | 10.3 | 10.7 |
| 9-6* | 3 | 627 | 100 | 35 | 2.7 | 2.9 | 2.9 | 3.0 |

*Allyl chloride was freshly distilled.

Example 10: Preparation of Methyl 12,12-Diethoxy-9-Dodecenoate from Methyl-9-dodecenoate and 3-butenal Diethyl Acetal Step 1: Methyl 9-dodecenoate was Prepared as Described in Step 1 of EXAMPLE 1

Cross-Metathesis of methyl-9-dedecenoate with 3-butenal diethyl acetal.

Methyl 9-dodecenoate and 3-butenal diethyl acetal were combined and degassed with argon for 30 minutes, then warmed to temperature (see, TABLE 10). Next, a metathesis catalyst (see, TABLE 10) was added to the methyl 9-dodecenoate and 3-butenal diethyl acetal mixture. The mixture was then allowed to metathesize for the time reported in TABLE 10. GC analysis indicated that the product [$CH_3O_2C(CH_2)_7CH=CHCH_2CH(OCH_2CH_3)_2$] was produced in the GC yield reported in TABLE 10.

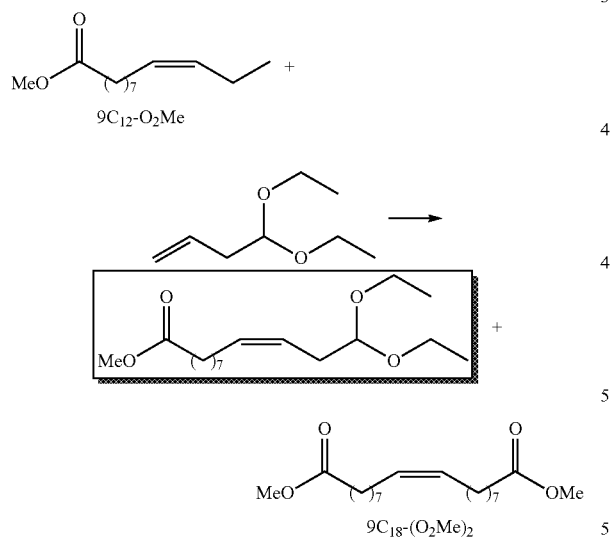

Example 11: Preparation of Methyl 12-tert-Butoxy-9-Dodecenoate from Methyl-9-dodecenoate and 1-tert-butoxybut-3-ene Step 1: Methyl 9-dodecenoate was Prepared as Described in Step 1 of EXAMPLE 1

Step 2: Cross-Metathesis of methyl-9-dodecenoate with 1-tert-butoxybut-3-ene

Methyl 9-dodecenoate and 1-tert-butoxybut-3-ene were combined and degassed with argon for 30 minutes, then warmed to temperature (see, TABLE 11). Next, a metathesis catalyst (see, TABLE 11) was added to the methyl 9-dodecenoate and 1-tert-butoxybut-3-ene mixture. The mixture was then allowed to metathesize for the time reported in TABLE 11. GC analysis indicated that the product [$CH_3O_2C(CH_2)_7CH=CH(CH_2)_2OC(CH_3)_3$] was produced in the GC yield reported in TABLE 11.

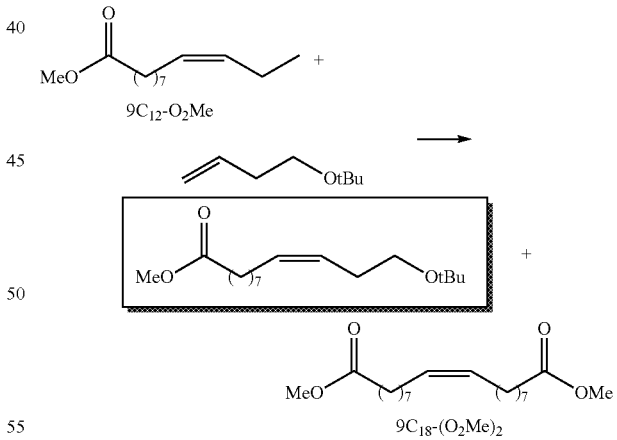

TABLE 10

| Exp# | Equiv of 3-butenal diethyl acetal | Catalyst | catalyst loading (ppm) | Temp (° C.) | GC Area % Product | | | |
|---|---|---|---|---|---|---|---|---|
| | | | | | 30 min | 60 min | 120 min | 240 min |
| 10-1 | 3 | 827 | 500 | 60 | 6.6 | 7.2 | 7.5 | 7.3 |
| 10-2 | 3 | 827 | 250 | 60 | 3.0 | 3.5 | 3.6 | 3.5 |
| 10-3 | 3 | 827 | 100 | 60 | 1.0 | 1.2 | 1.3 | 1.2 |

TABLE 11

| Exp# | Equiv of 1-tert-butoxy but-3-ene | catalyst | catalyst loading (ppm) | Temp (° C.) | GC Area % (Product) | | | |
|---|---|---|---|---|---|---|---|---|
| | | | | | 30 min | 60 min | 120 min | 240 min |
| 11-1 | 3 | 827 | 1000 | 60 | 17.7 | 16.4 | 16.9 | 17.2 |
| 11-2 | 3 | 827 | 500 | 60 | 19.0 | 18.7 | 18.9 | 19.3 |
| 11-3 | 3 | 827 | 250 | 60 | 18.5 | 18.1 | 18.2 | 18.4 |

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims. All patents, patent documents, and publications cited herein are hereby incorporated by reference as if individually incorporated.

What is claimed is:

1. A method comprising:
providing (a) a starting material comprising unsaturated fatty acid triglycerides and (b) short-chain alpha-olefins;
cross-metathesizing the unsaturated fatty acid triglycerides of the starting material and the short-chain alpha-olefins in the presence of a metathesis catalyst to provide cross-metathesis products comprising olefins and ester-functionalized alkenes, wherein the ester-functionalized alkenes comprise unsaturated fatty acid triglycerides;
separating the olefins in the cross-metathesis products and the ester-functionalized alkenes in the cross-metathesis products to provide separated olefins and separated ester-functionalized alkenes, wherein the separated ester-functionalized alkenes comprise unsaturated fatty acid triglycerides; and
transesterifying the separated ester-functionalized alkenes in the presence of an alcohol to provide a transesterified product comprising glycerol and free ester-functionalized alkenes.

2. The method of claim 1, further comprising:
separating spent metathesis catalyst in the cross-metathesis products to provide separated spent metathesis catalyst.

3. The method of claim 1, further comprising:
separating the glycerol in the transesterified product and the free ester-functionalized alkenes in the transesterified product to provide separated glycerol and separated free ester-functionalized alkenes.

4. The method of claim 3, further comprising:
self-metathesizing the separated free-ester functionalized alkenes in the presence of second metathesis catalyst to provide a self-metathesis product comprising diester alkenes.

5. The method of claim 4, further comprising:
hydrogenating the diester alkenes in the self-metathesis product.

6. The method of claim 1, wherein the starting material is a natural oil.

7. The method of claim 6, wherein the natural oil is a plant-based oil or animal fat.

8. The method of claim 7, wherein the plaint-based oil is selected from the group consisting of: canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, castor oil, and mixtures thereof.

9. The method of claim 7, wherein the animal fat is selected from the group consisting of: lard, tallow, chicken fat, fish oil, and mixtures thereof.

10. The method of claim 1, wherein the alcohol is a monohydric alcohol.

11. The method of claim 10, wherein the monohydric alcohol is selected from the group consisting of: methanol, ethanol, propanol, butanol, and mixtures thereof.

12. The method of claim 10, wherein the monohydric alcohol is methanol.

13. The method of claim 1, wherein the short-chain alpha-olefins are selected from the group consisting of: 1-propene, 1-butene, 1-pentene, 1-hexene, 1-heptene, 1-octene, 1-nonene, and mixtures thereof.

* * * * *